US012697351B2

(12) United States Patent
Riedemann et al.

(10) Patent No.: US 12,697,351 B2
(45) Date of Patent: Aug. 4, 2026

(54) METHOD OF TREATING CONDITIONS, REDUCING AN INFLAMMATORY RESPONSE, OR IMPROVING ORGAN FUNCTION IN A SUBJECT HAVING A CORONA VIRUS INFECTION BY ADMINISTERING AN INHIBITOR OF C5a ACTIVITY

(71) Applicant: InflaRx GmbH, Jena (DE)

(72) Inventors: Niels C. Riedemann, Jena (DE); Renfeng Guo, Ann Arbor, MI (US)

(73) Assignee: InflaRx GmbH, Jena (DE)

( * ) Notice: Subject to any disclaimer, the term of this patent is extended or adjusted under 35 U.S.C. 154(b) by 860 days.

(21) Appl. No.: 17/914,685

(22) PCT Filed: Mar. 27, 2020

(86) PCT No.: PCT/EP2020/058878
§ 371 (c)(1),
(2) Date: Sep. 26, 2022

(87) PCT Pub. No.: WO2021/190770
PCT Pub. Date: Sep. 30, 2021

(65) Prior Publication Data

US 2023/0158060 A1 May 25, 2023

(51) Int. Cl.

| | |
|---|---|
| ***A61K 31/713*** | (2006.01) |
| ***A61K 31/7125*** | (2006.01) |
| ***A61P 11/00*** | (2006.01) |
| ***C07K 16/28*** | (2006.01) |

(52) U.S. Cl.
CPC ........ *A61K 31/713* (2013.01); *A61K 31/7125* (2013.01); *A61P 11/00* (2018.01); *C07K 16/2896* (2013.01)

(58) Field of Classification Search
CPC .............. A61K 31/713; A61K 31/7125; A61K 2039/505; A61P 11/00; A61P 31/00; A61P 31/14; A61P 37/00; C07K 16/2896; C07K 16/18; C07K 2317/76; Y02A 50/30
See application file for complete search history.

(56) References Cited

U.S. PATENT DOCUMENTS

| | | | | |
|---|---|---|---|---|
| 4,704,355 | A | 11/1987 | Bernstein | |
| 5,939,598 | A | 8/1999 | Kucherlapati et al. | |
| 6,355,245 | B1 | 3/2002 | Evans et al. | |
| 8,802,096 | B2 * | 8/2014 | Guo | C07K 16/18 530/389.3 |
| 10,376,595 | B2 | 8/2019 | Guo et al. | |
| 11,273,225 | B2 | 3/2022 | Guo et al. | |
| 11,464,868 | B2 | 10/2022 | Guo et al. | |
| 12,180,274 | B2 * | 12/2024 | Riedemann | C07K 16/18 |
| 2003/0118592 | A1 | 6/2003 | Ledbetter et al. | |
| 2003/0133939 | A1 | 7/2003 | Ledbetter et al. | |
| 2004/0110226 | A1 | 6/2004 | Lazar et al. | |
| 2010/0129346 | A1 | 5/2010 | Mackay | |
| 2012/0219566 | A1 | 8/2012 | Medof et al. | |
| 2012/0231008 | A1 | 9/2012 | Guo et al. | |
| 2013/0004514 | A1 | 1/2013 | Zahn et al. | |
| 2017/0137499 | A1 | 5/2017 | Guo et al. | |
| 2017/0349575 | A1 | 12/2017 | Musicki et al. | |
| 2018/0280530 | A1 | 10/2018 | Guo et al. | |
| 2018/0282425 | A1 | 10/2018 | Guo et al. | |
| 2020/0061202 | A1 | 2/2020 | Guo et al. | |
| 2020/0290969 | A1 | 9/2020 | Li et al. | |
| 2021/0046191 | A1 | 2/2021 | Guo et al. | |
| 2023/0279087 | A1 | 9/2023 | Guo et al. | |

FOREIGN PATENT DOCUMENTS

| | | | |
|---|---|---|---|
| CN | 1604909 | A | 4/2005 |
| CN | 1847261 | A | 10/2006 |
| CN | 1997384 | A | 7/2007 |
| CN | 105037541 | A | 11/2015 |
| CN | 105392803 | A | 3/2016 |
| CN | 106132982 | A | 11/2016 |
| CN | 111108118 | A | 5/2020 |
| JP | 2012514465 | A | 6/2012 |
| JP | 2014529997 | A | 11/2014 |
| JP | 2015511965 | A | 4/2015 |
| JP | 2016518331 | A | 6/2016 |
| JP | 2016523829 | A | 8/2016 |
| JP | 2017514791 | A | 6/2017 |
| TW | 201904611 | A | 2/2019 |
| WO | 1991004014 | A1 | 4/1991 |
| WO | 1999000406 | A1 | 1/1999 |

(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*

(Continued)

*Primary Examiner* — Robert S Landsman
(74) *Attorney, Agent, or Firm* — Greenberg Traurig, LLP; Melissa Hunter-Ensor; Leslie Serunian

(57) ABSTRACT

The present invention relates to an inhibitor of C5a activity medical condition caused by or associated with infection with a corona virus. The invention also relates to the use of an inhibitor of C5a activity in the reduction of an inflammatory response in a subject suffering from a corona virus infection. The invention further relates to an inhibitor of C5a activity for use in the improvement of organ function, in particular lung function and/or hepatic function, in a subject suffering from a corona virus infection.

12 Claims, 10 Drawing Sheets

Specification includes a Sequence Listing.

(56) References Cited

FOREIGN PATENT DOCUMENTS

| | | | |
|---|---|---|---|
| WO | 2001015731 | A1 | 3/2001 |
| WO | 2003015819 | A1 | 2/2003 |
| WO | 2003033528 | A1 | 4/2003 |
| WO | 2005079363 | A2 | 9/2005 |
| WO | 2005092366 | A1 | 10/2005 |
| WO | 2006082406 | A2 | 8/2006 |
| WO | 2008009062 | A1 | 1/2008 |
| WO | 2008029167 | A1 | 3/2008 |
| WO | 2010075257 | A1 | 7/2010 |
| WO | 2010079314 | A2 | 7/2010 |
| WO | 2011063980 | A1 | 6/2011 |
| WO | 2011137395 | A1 | 11/2011 |
| WO | 2011163640 | A1 | 12/2011 |
| WO | 2013041730 | A1 | 3/2013 |
| WO | 2013138586 | A1 | 9/2013 |
| WO | 2014160129 | A2 | 10/2014 |
| WO | 2014180961 | A1 | 11/2014 |
| WO | 2015140304 | A1 | 9/2015 |
| WO | 2016044419 | A1 | 3/2016 |
| WO | 2016061066 | A1 | 4/2016 |
| WO | 2016102877 | A1 | 6/2016 |
| WO | 2016209956 | A1 | 12/2016 |
| WO | 2017176620 | A2 | 10/2017 |
| WO | 2017218515 | A1 | 12/2017 |
| WO | 2018175833 | A1 | 9/2018 |
| WO | 2018184739 | A1 | 10/2018 |
| WO | 2018234118 | A1 | 12/2018 |
| WO | 2020051418 | A1 | 3/2020 |
| WO | 2020182384 | A1 | 9/2020 |
| WO | 2020214716 | A1 | 10/2020 |
| WO | 2021188601 | A1 | 9/2021 |
| WO | 2021190770 | A1 | 9/2021 |
| WO | 2021205013 | A1 | 10/2021 |
| WO | 2021211940 | A1 | 10/2021 |

OTHER PUBLICATIONS

Lauffer MC, et al. (2024) Communications Medicine. 4:6. (https://doi.org/10.1038/s43856-023-00419-1).*

Biocompare.com (https://www.biocompare.com/pfu/110447/soids/5067/Antibodies/Complement_C5a—retrieved from the internet Sep. 14, 2025).*

Samaee et al., "Tocilizumab for treatment patients with COVID-19: Recommended medication for novel disease," International Immunopharmacology, 2020, vol. 89, Article No. 107018, pp. 1-7.

Weiss et al., "Rapid mapping of protein functional epitopes by combinatorial alanine scanning," Proceedings of the National Academy of Sciences, 2000, vol. 97, No. 16, pp. 8950-8954.

Beijing Daily, "It only took 10 days! Beijing's first COVID-19 pneumonia treatment drug approved for clinical trial", accessed online Feb. 7, 2025, <https://baijiahao.baidu.com/s?Id=1658405784866908425&wfr=spider&for=p>, (3 pages); English translation accessed online Mar. 20, 2025 <https://www.takefoto.cn/viewnews-2046806.html#go_top>, (2 pages).

Office Action and Search Report received Feb. 13, 2025, in corresponding Chinese application No. 202080099072.X (7 pages).

English translation of Office Action and Search Report received Feb. 13, 2025, in corresponding Chinese application No. 202080099072.X (6 pages).

Allegretti et al., "Targeting C5a: Recent Advances in Drug Discovery," Current Medicinal Chemistry, 2005, vol. 12, No. 2, pp. 217-236.

Almagro et al., "Humanization of antibodies," Frontiers in Bioscience, Jan. 1, 2008, vol. 13, pp. 1619-1633.

Ami et al., "Co-infection of respiratory bacterium with severe acute respiratory syndrome coronavirus induces an exacerbated pneumonia in mice," Microbiology and Immunology, 2008, vol. 52, pp. 118-127.

Anonymous, "No significant treatment effect found for IFX-1 in hidradenitis suppurativa trial," Jun. 7, 2019, retrieved from the Internet on Nov. 12, 2019, <https://www.healio.com/dermatology/skin-care/news/online/{72df4fe7-aaec-41b0-be1f-0179ed471924}/no-significant-treatment-effect-found-for-ifx-1-in-hidradenitis-suppurativa-trial> (2 pages).

Argyropoulou et al., "An Open-Label Trial to Assess the Safety of IFX-1 in Patients with Hidradenitis Suppurativa Not Eligible for Adalimumab," Aug. 4, 2017, poster (1 page).

Bekker et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study," PLoS One, Oct. 21, 2016, vol. 11, No. 10, e0164646, pp. 1-19.

Beinrohr et al., "C1, MBL-MASPs and C1-inhibitor: novel approaches for targeting complement-mediated inflammation," Trends in Molecular Medicine, 2008, vol. 14, No. 12, pp. 511-521.

Biedermann et al., "Regulation of T cell immunity in atopic dermatitis by microbes: the Yin and Yang of cutaneous Inflammation," Frontiers in Immunology, Jul. 13, 2015, vol. 6, Article 353, pp. 1-9.

Binz et al., "Engineering novel binding proteins from nonimmunoglobulin domains," Nature Biotechnology, Oct. 2005, vol. 23, No. 10, pp. 1257-1268.

Bird et al., "Single-Chain Antigen-Binding Proteins," Science, Oct. 21, 1988, vol. 242, pp. 423-426.

Blok et al., "Gene expression profiling of skin and blood in hidradenitis suppurativa," British Journal of Dermatology, 2016, vol. 174, pp. 1392-1394.

Braun-Falco et al., "Pyoderma gangrenosum, acne, and suppurative hidradenitis (PASH)—a new autoinflammatory syndrome distinct from PAPA syndrome," Journal of the American Academy of Dermatology, Mar. 2012, vol. 66, No. 3, pp. 409-415.

Brody et al., "Aptamers as therapeutic and diagnostic agents," Reviews in Molecular Biotechnology, 2000, vol. 74, pp. 5-13.

Buchwald et al., "Long-term, continuous intravenous heparin administration by an implantable infusion pump in ambulatory patients with recurrent venous thrombosis," Surgery, Oct. 1980, vol. 88, No. 4, pp. 507-516.

Cannon, "Analog Design," Chapter 19 in Burger's Medicinal Chemistry and Drug Discovery, 5th Edition, vol. I: Principles and Practice, 1995, pp. 783-802.

Carvelli et al., "Identification of immune checkpoints in COVID-19," Research Square, 2020, pp. 1-30.

Chan et al., "Middle East Respiratory Syndrome Coronavirus: Another Zoonotic Betacoronavirus Causing SARS-Like Disease," Clinical Microbiology Reviews, Apr. 2015, vol. 28, No. 2, pp. 465-522.

Chang et al., "Epidemiologic and Clinical Characteristics of Novel Coronavirus Infections Involving 13 Patients Outside Wuhan, China," JAMA, Mar. 17, 2020, vol. 323, No. 11, pp. 1092-1093.

Che et al., "Nucleocapsid Protein as Early Diagnostic Marker for SARS," Emerging Infectious Diseases, Nov. 2004, vol. 10, No. 11, pp. 1947-1949.

Chen et al., "Clinical and immunologic features in severe and moderate forms of Coronavirus Disease 2019," medRxiv, Feb. 19, 2020, pp. 1-33.

Chen et al., "Enhancement and destruction of antibody function by somatic mutation: unequal occurrence is controlled by V gene combinatorial associations," The EMBO Journal, 1995, vol. 14, No. 12, pp. 2784-2794.

Chen et al., "Epidemiological and clinical characteristics of 99 cases of 2019 novel coronavirus pneumonia in Wuhan, China: a descriptive study," The Lancet, Feb. 15, 2020, vol. 395, pp. 507-513.

Chen et al., "Plasma proteome of severe acute respiratory syndrome analyzed by two-dimensional gel electrophoresis and mass spectrometry," Proceedings of the National Academy of Sciences of the United States of America, Dec. 7, 2004, vol. 101, No. 49, pp. 17039-17044.

ClinicalTrials.gov archive, "History of Changes for Study: NCT03001622, Studying Complement Inhibition in Patients With Moderate to Severe Hidradenitis Suppurativa," Study NCT03001622, Submitted Date: Dec. 20, 2016 (v1), pp. 1-5.

ClinicalTrials.gov archive, "History of Changes for Study: NCT03001622, Studying Complement Inhibition in Patients With

(56) References Cited

OTHER PUBLICATIONS

Moderate to Severe Hidradenitis Suppurativa," Study NCT03001622, Submitted Date: Mar. 20, 2017 (v3), pp. 1-6.
Colman, P. M., "Effects of amino acid sequence changes on antibody-antigen interactions," Research in Immunology, Jan. 1994, vol. 145, No. 1, pp. 33-36.
Cugno et al., "PAPA, PASH and PAPASH Syndromes: Pathophysiology, Presentation and Treatment," American Journal of Clinical Dermatology, Feb. 2017, vol. 18, pp. 555-562.
Cole et al., "Beyond lysis: how complement influences cell fate," Clinical Science, 2003, vol. 104, pp. 455-466.
Cumpelik et al., "Neutrophil microvesicles resolve gout by inhibiting C5a-mediated priming of the inflammasome," Annals of the Rheumatic Diseases, 2016, vol. 75, No. 6, pp. 1236-1245.
Czermak et al., "In Vitro and In Vivo Dependency of Chemokine Generation on C5a and TNF-α," The Journal of Immunology, 1999, vol. 162, pp. 2321-2325.
Czermak et al., "Protective effects of C5a blockade in sepsis," Nature Medicine, Jul. 1999, vol. 5, No. 7, pp. 788-792.
D'Angelo et al., "Many Routes to an Antibody Heavy-Chain CDR3: Necessary, Yet Insufficient, for Specific Binding," Frontiers in Immunology, Mar. 2018, vol. 9, Article 395, pp. 1-13.
Dang et al., "Role of the complement anaphylatoxin C5a-receptor pathway in atopic dermatitis in mice," Molecular Medicine Reports, 2015, vol. 11, pp. 4183-4189.
Deming et al., "Vaccine Efficacy in Senescent Mice Challenged with Recombinant SARS-CoV Bearing Epidemic and Zoonotic Spike Variants," PLoS Medicine, Dec. 2006, vol. 3, No. 12, e525, pp. 2359-2375.
Devyatyarova-Johnson et al., "The Lipopolysaccharide Structures of *Salmonella enterica* Serovar *typhimurium* and Neisseria gonorrhoeaeDetermine the Attachment of Human Mannose-Binding Lectin to Intact Organisms," Infection and Immunity, Jul. 2000, vol. 68, No. 7, pp. 3894-3899.
Dhingra et al., "Attenuated neutrophil axis in atopic dermatitis compared to psoriasis reflects TH17 pathway differences between these diseases," Journal of Allergy and Clinical Immunology, Aug. 2013, vol. 132, No. 2, pp. 1-7.
Drosten et al., "Identification of a Novel Coronavirus in Patients with Severe Acute Respiratory Syndrome," The New England Journal of Medicine, May 15, 2003, vol. 348, No. 20, pp. 1967-1976.
Dunkelberger et al., "Complement and its role in innate and adaptive immune responses," Cell Research, 2010, vol. 20, pp. 34-50.
During et al., "Controlled Release of Dopamine from a Polymeric Brain Implant: In Vivo Characterization," Annals of Neurology, Apr. 1989, vol. 25, No. 4, pp. 351-356.
Fan et al., "Clinical Features of COVID-19-Related Liver Damage," medRxiv, Feb. 28, 2020, pp. 1-21.
Finch et al., "Low-Molecular-Weight Peptidic and Cyclic Antagonists of the Receptor for the Complement Factor C5a," Journal of Medicinal Chemistry, 1999, vol. 42, No. 11, pp. 1965-1974.
Gál et al., "A True Autoactivating Enzyme: Structural Insight into Mannose-Binding Lectin-Associated Serine Protease-2 Activations," The Journal of Biological Chemistry, Sep. 30, 2005, vol. 280, No. 39, pp. 33435-33444.
Gao et al., "Expression in *Escherichia coli* and Purification of Full Length Recombinant Human MASP2," Letters in Biotechnology, Nov. 2011, vol. 22, No. 6, pp. 806-808 and 891. [English Abstract].
Gao et al., "Highly pathogenic coronavirus N protein aggravates lung injury by MASP-2-mediated complement over-activation," medRxiv, Mar. 2020, pp. 1-25.
Garcia et al., "Complement C5 Activation during Influenza A Infection in Mice Contributes to Neutrophil Recruitment and Lung Injury," PLoS One, May 2013, vol. 8, No. 5, e64443, pp. 1-11.
Giamarellos-Bourboulis et al., "Abstract: O03-2 | Complement activation in hidradenitis suppurativa," Experimental Dermatology, 2017, vol. 26, Suppl. 1, pp. 3-38.
Goodson, J. Max, "Dental Applications," Medical Applications of Controlled Release, 1984, vol. II, Chapter 6, pp. 115-138.
Graham et al., "A decade after SARS: strategies for controlling emerging coronaviruses," Nature Reviews Microbiology, Dec. 2013, vol. 11, pp. 836-848.
Graille et al., "CA206: PAPA, PASH, PAPASH, PsAPASH, PASS . . . des syndromes auto-inflammatoires PAS si simples," La Revue de Médecine Interne, 2015, vol. 36, pp. A205-A206.
Gralinski et al., "Complement Activation Contributes to Severe Acute Respiratory Syndrome Coronavirus Pathogenesis," mBio, Sep./Oct. 2018, vol. 9, No. 5, e01753-18, pp. 1-15.
Gueler et al., "Complement 5a Receptor Inhibition Improves Renal Allograft Survival," Journal of the American Society of Nephrology, 2008, vol. 19, pp. 2302-2312.
Guo et al., "Divergent Signaling Pathways in Phagocytic Cells during Sepsis," The Journal of Immunology, 2006, vol. 177, No. 2, pp. 1306-1313.
Guo et al., "IFX-1 blocking the anaphylatoxin C5a—an anti-inflammatory effect in patients with hidradenitis suppurativa," Aug. 29, 2017, poster (1 page).
Guo et al., "Role of C5a in Inflammatory Responses," Annual Review of Immunology, 2005, vol. 23, pp. 821-852.
Harding, J., "Eculizumab," Drugs of the Future, 2004, vol. 29, No. 7, pp. 673-676.
Heap et al., "Analysis of a 17-amino acid residue, virus-neutralizing microantibody," Journal of General Virology, 2005, vol. 86, pp. 1791-1800.
Holliger et al., "'Diabodies': Small bivalent and bispecific antibody fragments," Proceedings of the National Academy of Sciences of the United States of America, Jul. 1993, vol. 90, No. 14, pp. 6444-6448.
Höpken et al., "Inhibition of interleukin-6 synthesis in an animal model of septic shock by anti-C5a monoclonal antibodies," European Journal of Immunology, 1996, vol. 26, pp. 1103-1109.
Howard III et al., "Intracerebral drug delivery in rats with lesion-induced memory deficits," Journal of Neurosurgery, Jul. 1989, vol. 71, pp. 105-112.
Huang et al., "Clinical features of patients infected with 2019 novel coronavirus in Wuhan, China," The Lancet, Feb. 15, 2020, vol. 395, pp. 497-506.
Huber-Lang et al., "Complement-Induced Impairment of Innate Immunity During Sepsis," The Journal of Immunology, 2002, vol. 169, No. 6, pp. 3223-3231.
Huber-Lang et al., "Protective effects of anti-C5a peptide antibodies in experimental sepsis," The FASEB Journal, Jan. 19, 2001, vol. 15, No. 3, pp. 568-570.
Huber-Lang et al., "Role of C5a in Multiorgan Failure During Sepsis," The Journal of Immunology, 2001, vol. 166, pp. 1193-1199.
Huston et al., "Protein engineering of antibody binding sites: Recovery of specific activity in an anti-digoxin single-chain Fv analogue produced in *Escherichia coli,*" Proceedings of the National Academy of Sciences of the United States of America, Aug. 1988, vol. 85, pp. 5879-5883.
Hycult Biotech Catalog, "Complement and Collectins," 2020-2021, Uden, The Netherlands, pp. 1-8.
Hyzewicz et al., "Low-Intensity Training and the C5a Complement Antagonist NOX-D21 Rescue the mdx Phenotype through Modulation of Inflammation," The American Journal of Pathology, May 2017, vol. 187, No. 5, pp. 1147-1161.
Imagawa et al., "Consequences of cell membrane attack by complement: Release of arachidonate and formation of inflammatory derivatives," Proceedings of the National Academy of Sciences of the United States of America, Nov. 1983, vol. 80, pp. 6647-6651.
InflaRx, "InflaRx initiates exploratory Phase II trial with IFX-1, a first-in-class anti-complement C5a antibody, in patients with Hidradenitis Suppurativa," Jan. 4, 2017, pp. 1-2.
InflaRx, "InflaRx Reports Additional Analysis of the SHINE Phase IIb Results for IFX-1 in Hidradenitis Suppurativa," Jul. 18, 2019, pp. 1-9.
InflaRx "InflaRx Reports Positive Results from the Open Label Extension Part of the SHINE Study for IFX-1 in Hidradenitis Suppurativa," Nov. 6, 2019, pp. 1-8.

(56) References Cited

OTHER PUBLICATIONS

Ip et al., "Mannose-Binding Lectin in Severe Acute Respiratory Syndrome Coronavirus Infection," The Journal of Infectious Diseases, May 15, 2005, vol. 191, pp. 1697-1704.
Jayne et al., "Randomized Trial of C5a Receptor Inhibitor Avacopan in ANCA-Associated Vasculitis," Journal of the American Society of Nephrology, 2017, vol. 28, pp. 2756-2767.
Jemec, "Medical treatment of hidradenitis suppurativa," Expert Opinion on Pharmacotherapy, 2004, vol. 5, No. 8, pp. 1767-1770.
Jemec et al., "The prevalence of hidradenitis suppurativa and its potential precursor lesions," Journal of the American Academy of Dermatology, Aug. 1996, vol. 35, No. 2, Pt. 1, pp. 191-194.
Jorizzo et al., "Low-dose weekly methotrexate for unusual neutrophilic vascular reactions: Cutaneous polyarteritis hodosa and Behcet's disease," Journal of the American Academy of Dermatology, Jun. 1991, vol. 24, No. 6, Pt. 1, pp. 973-978.
Kaplan, M., "Eculizumab," Current Opinion in Investigational Drugs, 2002, vol. 3, No. 7, pp. 1017-1023.
Kaplan, Mariana J., "Role of neutrophils in systemic autoimmune diseases," Arthritis Research & Therapy, 2013, vol. 15, Article No. 219, pp. 1-9.
Keseroglu et al., "A Case of Subcorneal Pustular Dermatosis Successfully Treated with Acitretin," Archives of Inflammation, Oct. 27, 2016, vol. 1, No. 2, pp. 1-3.
Khameneh et al., "C5a Regulates IL-1β Production and Leukocyte Recruitment in a Murine Model of Monosodium Urate Crystal-Induced Peritonitis," Frontiers in Pharmacology, Jan. 23, 2017, vol. 8, Article 10, pp. 1-11.
Kimball et al., "Assessing the validity, responsiveness and meaningfulness of the Hidradenitis Suppurativa Clinical Response (HiSCR) as the clinical endpoint for hidradenitis suppurativa treatment," British Journal of Dermatology, 2014, vol. 171, No. 6, pp. 1434-1442.
Klos et al., "International Union of Basic and Clinical Pharmacology. [corrected]. LXXXVII. Complement Peptide C5a, C4a, and C3a Receptors," Pharmacological Reviews, Jan. 2013, vol. 65, pp. 500-543.
Klos et al., "The role of the anaphylatoxins in health and disease," Molecular Immunology, 2009, vol. 46, pp. 2753-2766.
Kurzen et al., "What causes hidradenitis suppurativa?" Experimental Dermatology, 2008, vol. 17, No. 5, pp. 455-456.
Kussie et al., "A Single Engineered Amino Acid Substitution Changes Antibody Fine Specificity," Journal of Immunology, 1994, vol. 152, pp. 146-152.
Langer et al., "Chemical and Physical Structure of Polymers as Carriers for Controlled Release of Bioactive Agents: A Review," Journal of Macromolecular Science, Reviews in Macromolecular Chemistry and Physics, 1983, vol. 23, No. 1, pp. 61-126.
Langer, Robert, "New Methods of Drug Delivery," Science, Sep. 28, 1990, vol. 249, pp. 1527-1533.
Lee et al., "A Major Outbreak of Severe Acute Respiratory Syndrome in Hong Kong, " The New England Journal of Medicine, May 15, 2003, vol. 348, No. 20, pp. 1986-1994.
Levy et al., "Inhibition of Calcification of Bioprosthetic Heart Valves by Local Controlled-Release Diphosphonate," Science, Apr. 12, 1985, vol. 228, pp. 190-192.
Li et al., "Metformin reduces diabetes-related inflammatory molecules in human vitreous and retinal vascular endothelial cells," Investigative Ophthalmology & Visual Science, Sep. 2016, vol. 57, p. 6346; abstract submitted for the 2016 Annual Meeting of the Association for Research in Vision and Opthamology (ARVO).
Li et al., "Neuroprotective effects of argatroban and C5a receptor antagonist (PMX53) following intracerebral haemorrhage," Clinical and Experimental Immunology, 2014, vol. 175, No. 2, pp. 285-295.
Lima et al., "Keratinocytes and neutrophils are important sources of proinflammatory molecules in hidradenitis suppurativa," British Journal of Dermatology, 2016, vol. 174, pp. 514-521.
Liu et al., "Neutrophil-to-Lymphocyte Ratio Predicts Severe Illness Patients with 2019 Novel Coronavirus in the Early Stage," medRxiv, Feb. 12, 2020, pp. 1-14.
Liu et al., "Study on interaction between SARS-CoV N and MAP19," Chinese Journal of Cellular and Molecular Immunology, 2009, vol. 25, No. 9, pp. 777-779. [English Abstract].
Ma et al., "Incidence, clinical characteristics and prognostic factor of patients with COVID-19: a systematic review and meta-analysis," medRxiv, Mar. 20, 2020, pp. 1-51.
March et al., "Potent Cyclic Antagonists of the Complement C5a Receptor on Human Polymorphonuclear Leukocytes. Relationships between Structures and Activity," Molecular Pharmacology, 2004, vol. 65, No. 4, pp. 868-879.
Markiewski et al., "Modulation of the anti-tumor immune response by complement," Nature Immunology, Nov. 2008, vol. 9, No. 11, pp. 1225-1235.
Marzano et al., "Association of Pyoderma Gangrenosum, Acne, and Suppurative Hidradenitis (PASH) Shares Genetic and Cytokine Profiles With Other Autoinflammatory Diseases," Medicine, Dec. 2014, vol. 93, No. 27, e187, pp. 1-11.
Marzano et al., "Hidradenitis suppurativa, neutrophilic dermatoses and autoinflammation: what's the link?" British Journal of Dermatology, 2016, vol. 174, pp. 482-483.
Merle et al., "Complement System Part I—Molecular Mechanisms of Activation and Regulation," Frontiers in Immunology, Jun. 2, 2015, vol. 6, Article 262, pp. 1-30.
Morgan et al., "Complement, a target for therapy in inflammatory and degenerative diseases," Nature Reviews Drug Discovery, Dec. 2015, vol. 14, pp. 857-877.
Navarini et al., "Neutrophilic dermatoses and autoinflammatory diseases with skin involvement-innate immune disorders," Seminars in Immopathology, 2016, vol. 38, pp. 45-56.
Németh et al., "Neutrophils in animal models of autoimmune disease," Seminars in Immunology, Apr. 2016, vol. 28, No. 2, pp. 174-186.
Nunez-Cruz et al., "Genetic and Pharmacologic Inhibition of Complement Impairs Endothelial Cell Function and Ablates Ovarian Cancer Neovascularization," Neoplasia, Nov. 2012, vol. 14, No. 11, pp. 994-1004.
Okroj et al., "Functional Analyses of Complement Convertases Using C3 and C5-Depleted Sera," PLoS One, Oct. 2012, vol. 7, No. 10, e47245, pp. 1-13.
Oppermann et al., "Probing the Human Receptor for C5a Anaphylatoxin with Site-Directed Antibodies: Identification of a Potential Ligand Binding Site on the NH2-Terminal Domain," The Journal of Immunology, Oct. 1993, vol. 151, No. 7, pp. 3785-3794.
Pang et al., "Serum Proteomic Fingerprints of Adult Patients with Severe Acute Respiratory Syndrome," Clinical Chemistry, 2006, vol. 52, No. 3, pp. 421-429.
Pawaria et al., "Complement Component C5a Permits the Coexistence of Pathogenic Th17 Cells and Type 1 IFN in Lupus," The Journal of Immunology, 2014, vol. 193, No. 7, pp. 3288-3295.
Petersen et al., "An assay for the mannan-binding lectin pathway of complement activation," Journal of Immunological Methods, 2001, vol. 257, pp. 107-116.
Petitclerc et al., "Pathologic Leukocyte Infiltration of the Rabbit Aorta Confers a Vasomotor Effect to Chemotactic Peptides Through Cyclooxygenase-Derived Metabolites," The Journal of Immunology, May 1996, vol. 156, No. 9, pp. 3426-3434.
Piche-Nicholas et al., "Changes in complementarity-determining regions significantly alter IgG binding to the neonatal Fc receptor (FcRn) and pharmacokinetics," MABS, 2018, vol. 10, No. 1, pp. 81-94.
Prat et al., "Neutrophilic dermatoses as systemic diseases," Clinics in Dermatology, 2014, vol. 32, No. 3, pp. 376-388.
Proctor et al., "Transdermal Pharmacology of Small Molecule Cyclic C5a Antagonists," Advances in Experimental Medicine and Biology, 2006, vol. 586, pp. 329-345.
Qiu et al., "Small antibody mimetics comprising two complementarity-determining regions and a framework region for tumor targeting," Nature Biotechnology, 2007, vol. 25, No. 8, pp. 921-929.
Rawal et al., "Activation of Complement Component C5: Comparison of C5 Convertases of the Lectin Pathway and the Classical Pathway of Complement," The Journal of Biological Chemistry, Mar. 21, 2008, vol. 283, No. 12, pp. 7853-7863.

(56) References Cited

OTHER PUBLICATIONS

RCSB Protein 4UU9: Crystal structure of the human c5a in complex with MEDI7814 a neutralising antibody; retrieved from the Internet on May 26, 2023.

Ren et al., "The use of proteomics in the discovery of serum biomarkers from patients with severe acute respiratory syndrome," Proteomics, 2004, vol. 4, No. 11, pp. 3477-3484.

Revuz J., "Hidradenitis suppurativa," Journal of the European Academy of Dermatology and Venereology, 2009, vol. 23, No. 9, pp. 985-998.

Ricardo et al., "Preclinical Evaluation of RA101495, a Potent Cyclic Peptide Inhibitor of C5 for the Treatment of Paroxysmal Nocturnal Hemoglobinuria," Blood, 2015, vol. 126, No. 23, p. 939.

Ricklin et al., "The renaissance of complement therapeutics," Nature Reviews: Nephrology, Jan. 2018, vol. 14, pp. 26-47.

Riedemann et al., "Controlling the anaphylatoxin C5a in diseases requires a specifically targeted inhibition," Clinical Immunology, 2017, vol. 180, pp. 25-32.

Riedemann et al., "Expression and Function of the C5a Receptor in Rat Alveolar Epithelial Cells," The Journal of Immunology, 2002, vol. 168, pp. 1919-1925.

Riedemann et al., "Increased C5a receptor expression in sepsis," The Journal of Clinical Investigation, Jul. 2002, vol. 110, No. 1, pp. 101-108.

Riedemann et al., "Regulatory Role of C5a on Macrophage Migration Inhibitory Factor Release from Neutrophils," The Journal of Immunology, 2004, vol. 173, pp. 1355-1359.

Rittirsch et al., "Functional roles for C5a receptors in sepsis," Nature Medicine, May 2008, vol. 14, No. 5, pp. 551-557.

Rittirsch et al., "Harmful molecular mechanisms in sepsis," Nature Reviews Immunology, Oct. 2008, vol. 8, pp. 776-787.

Rota et al., "Characterization of a Novel Coronavirus Associated with Severe Acute Respiratory Syndrome," Science, May 30, 2003, vol. 300, pp. 1394-1399.

Rudikoff et al., "Single amino acid substitution altering antigen-binding specificity," Proceedings of the National Academy of Sciences of the United States of America, Mar. 1982, vol. 79, pp. 1979-1983.

Sánchez-Galán et al., "Leukotriene B4 enhances the activity of nuclear factor-kB pathway through BLT1 and BLT2 receptors in atherosclerosis," Cardiovascular Research, 2009, vol. 81, pp. 216-225.

Sarma et al., "Complement in lung disease," Autoimmunity, Aug. 2006, vol. 39, No. 5, pp. 387-394.

Saudek et al., "A Preliminary Trial of the Programmable Implantable Medication System for Insulin Delivery," The New England Journal of Medicine, Aug. 31, 1989, vol. 321, No. 9, pp. 574-579.

Schatz-Jakobsen et al., "Structural and functional characterization of human and murine C5a anaphylatoxins," Acta Crystallographica Section D Biological Crystallography, Jun. 2014, vol. 70, Pt. 6, pp. 1704-1717.

Schwaeble et al., "Targeting of mannan-binding lectin-associated serine protease-2 confers protection from myocardial and gastrointestinal ischemia/reperfusion injury," Proceedings of the National Academy of Sciences of the United States of America, May 3, 2011, vol. 108, No. 18, pp. 7523-7528.

Sefton, Michael V., "Implantable Pumps," CRC Critical Reviews in Biomedical Engineering, 1987, vol. 14, No. 3, pp. 201-240.

Slade et al., "Hidradenitis suppurativa: pathogenesis and management," British Journal of Plastic Surgery, 2003, vol. 56, No. 5, pp. 451-461.

Smith, Kristen, "If at first you don't succeed . . . ," Jul. 2019; retrieved from the Internet on Nov. 12, 2019 <https://www.ddn-news.com/index.php?newsarticle=13478> (2 pages).

Song et al., "C5a receptor1 inhibition alleviates influenza virus-induced acute lung injury," International Immunopharmacology, 2018, vol. 59, pp. 12-20.

Souza et al., "APT070 (Mirococept), a membrane-localised complement inhibitor, inhibits inflammatory responses that follow intestinal ischaemia and reperfusion injury," British Journal of Pharmacology, 2005, vol. 145, No. 8, pp. 1027-1034.

Strainic et al., "Absent C3a and C5a receptor signaling into CD4+ T cells enables auto-inductive TGF-β1 signaling and induction of Foxp3+ T regulatory cells," Nature Immunology, Feb. 2013, vol. 14, No. 2, pp. 162-171.

Strieter et al., "Cytokine-induced Neutrophil-derived Interleukin-8," American Journal of Pathology, Aug. 1992, vol. 141, No. 2, pp. 397-407.

Sun et al., "Inhibition of Complement Activation Alleviates Acute Lung Injury Induced by Highly Pathogenic Avian Influenza H5N1 Virus Infection," American Journal of Respiratory Cell and Molecular Biology, Aug. 2013, vol. 49, No. 2, pp. 221-230.

Surjit et al., "The Severe Acute Respiratory Syndrome Coronavirus Nucleocapsid Protein Is Phosphorylated and Localizes in the Cytoplasm by 14-3-3-Mediated Translocation," Journal of Virology, Sep. 2005, vol. 79, No. 17, pp. 11476-11486.

Tagami, "Recent topics in sterile pustular dermatoses," Japanese Journal of Inflammation, 1986, vol. 6, No. 1, pp. 5-14. [English Abstract].

Takahashi et al., "The mannose-binding lectin: a prototypic pattern recognition molecule," Current Opinion in Immunology, 2006, vol. 18, pp. 16-23.

Tang et al., "Abnormal coagulation parameters are associated with poor prognosis in patients with novel coronavirus pneumonia," Journal of Thrombosis and Haemostasis, 2020, vol. 18, pp. 844-847.

Tang et al., "Anticoagulant treatment is associated with decreased mortality in severe coronavirus disease 2019 patients with coagulopathy," Journal of Thrombosis and Haemostasis, 2020, vol. 18, pp. 1094-1099.

Taylor, Phil, "InflaRx flatlines after skin disease drug flops in midstage trial," pharmaphorum, Jun. 6, 2019; retrieved from the Internet on Nov. 12, 2019 <https://pharmaphorum.com/news/inflarx-flatlines-skin-disease-drug-midstage-trial/> (2 pages).

Ternowitz et al., "Methotrexate Inhibits the Human C5a-Induced Skin Response in Patients with Psoriasis," The Journal of Investigative Dermatology, Aug. 1987, vol. 89, No. 2, pp. 192-196.

Tesar et al., "Avacopan in the treatment of ANCA-associated vasculitis," Expert Opinion on Investigational Drugs, 2018, vol. 27, No. 5, pp. 491-496.

Treat et al., "Liposome Encapsulated Doxorubicin Preliminary Results of Phase I and Phase II Trials," Liposomes in the Therapy of Infectious Diseases and Cancer, Lopez-Berestein and Fidler (eds.), 1989, pp. 353-365.

Altschul et al., "Basic Local Alignment Search Tool," Journal of Molecular Biology, 1990, vol. 215, pp. 403-410.

Altschul et al., "Gapped BLAST and PSI-BLAST: a new generation of protein database search programs," Nucleic Acids Research, 1997, vol. 25, No. 17, pp. 3389-3402.

Brudno et al., "Glocal alignment: finding rearrangements during alignment," Bioinformatics, 2003, vol. 19, Suppl. 1, pp. i54-i62.

Bryson et al., "Prediction of Immunogenicity of Therapeutic Proteins: Validity of Computational Tools," Biodrugs, 2010, vol. 24, Article No. 1, pp. 1-8.

Guo et al., "C5a, a Therapeutic Target in Sepsis," Recent Patents on Anti-Infective Drug Discovery, 2006, vol. 1, No. 1, pp. 57-65.

Holgate et al., "Circumventing immunogenicity in the development of therapeutic antibodies," IDrugs, 2009, vol. 12, No. 4, pp. 233-237.

Hu et al., "Large-scale mammalian cell culture," Current Opinion in Biotechnology, 1997, vol. 8, pp. 148-153.

Karlin et al., "Applications and statistics for multiple high-scoring segments in molecular sequences," Proceedings of the National Academy of Sciences of the United States of America, Jun. 1993, vol. 90, pp. 5873-5877.

Klos et al., "Detection of native human complement components C3 and C5 and their primary activation peptides C3a and C5a (anaphylatoxic peptides) by ELISAs with monoclonal antibodies," Journal of Immunological Methods, 1988, vol. 111, pp. 241-252.

Larkin et al., "Clustal Wand Clustal X version 2.0," Bioinformatics, 2007, vol. 23, No. 21, pp. 2947-2948.

(56) References Cited

OTHER PUBLICATIONS

Perry et al., "New Approaches to Prediction of Immune Responses to Therapeutic Proteins during Preclinical Development," Drugs in R & D, 2008, vol. 9, No. 6, pp. 385-396.
Strainic et al., "Absence of signaling into CD4+ cells via C3aR and C5aR enables autoinductive TGF-β1 signaling and induction of Foxp3+ regulatory T cells," Nature Immunology, Feb. 2013, vol. 14, No. 2, pp. 162-171.
Thompson et al., "Clustal W: improving the sensitivity of progressive multiple sequence alignment through sequence weighting, position-specific gap penalties and weight matrix choice," Nucleic Acids Research, 1994, vol. 22, No. 22, pp. 4673-4680.
Ward, Peter A., "Functions of C5a receptors," Journal of Molecular Medicine, Apr. 2009, vol. 87, No. 4, pp. 375-378.
Xu et al., "Interleukin-17 and its expanding biological functions," Cellular & Molecular Immunology, 2010, vol. 7, pp. 164-174.
Office Action dated Oct. 3, 2023 in corresponding Japanese Patent Application No. 2022-558062 (7 pages).
English translation of the Office Action dated Oct. 3, 2023 in corresponding Japanese Patent Application No. 2022-558062 (7 pages).
Tzanetakou et al., "Safety and Efficacy of Anakinra in Severe Hidradenitis Suppurativa: A Randomized Clinical Trial," JAMA Dermatology, 2016, vol. 152, No. 1, pp. 52-59.
UniProtKB P01031: CO5_Human; retrieved from the Internet on May 26, 2023 (13 pages).
UniProtKB P05231: IL6_Human; retrieved from the Internet on May 26, 2023 (12 pages).
USBiological Life Sciences Certificate of Analysis for Antibody Clone No. 7H110 (Mouse Anti-Human CD88 Antibody), Date of Manufacture: May 17, 2017 (1 page).
Verdolini et al., "Metformin for the treatment of hidradenitis suppurativa: a little help along the way," Journal of the European Academy of Dermatology and Venereology, 2013, vol. 27, No. 9, pp. 1101-1108.
Wallis, Russell, "Interactions between mannose-binding lectin and MASPs during complement activation by the ectin pathway," Immunobiology, 2007, vol. 212, pp. 289-299.
Wang et al., "Clinical Characteristics of 138 Hospitalized Patients With 2019 Novel Coronavirus-Infected Pneumonia in Wuhan, China," JAMA, Mar. 17, 2020, vol. 323, No. 11, pp. 1061-1069.
Wang et al., "Consecutive false-negative rRT-PCR test results for SARS-CoV-2 in patients after clinical recovery from COVID-19," Journal of Medical Virology, 2020, vol. 92, pp. 2887-2890.
Ward et al., "Binding activities of a repertoire of single immunoglobulin variable domains secreted from *Escherichia coli,*" Nature, Oct. 12, 1989, vol. 341, pp. 544-546.
Ward, Peter A., "Functions of C5a receptors," Journal of Molecular Medicine, Apr. 2009, vol. 87, pp. 375-378.
Werfel et al., "C5a receptors are detectable on mast cells in normal human skin and in psoriatic plaques but not in weal and flare reactions or in urticaria pigmentosa by immunohistochemistry," Archives of Dermatological Research, 1997, vol. 289, pp. 83-86.
Wills-Karp, Marsha, "Complement Activation Pathways: A Bridge between Innate and Adaptive Immune Responses in Asthma," Proceedings of the American Thoracic Society, 2007, vol. 4, pp. 247-251.
Wollina et al., "Acne inversa (Hidradenitis suppurativa): A review with a focus on pathogenesis and treatment," Indian Dermatology Online Journal, Jan.-Mar. 2013, vol. 4, No. 1, pp. 2-11.
World Health Organization Multicentre Collaborative Network for Severe Acute Respiratory Syndrome (SARS) Diagnosis,"A multicentre collaboration to investigate the cause of severe acute respiratory syndrome," The Lancet, May 17, 2003, vol. 361, pp. 1730-1733.
Xu et al., "Complement C5a regulates IL-17 by affecting the crosstalk between DC and γδ T cells in CLP-induced sepsis," European Journal of Immunology, 2010, vol. 40, No. 4, pp. 1079-1088.
Yasui et al., "Prior Immunization with Severe Acute Respiratory Syndrome (SARS)-Associated Coronavirus (SARS-CoV) Nucleocapsid Protein Causes Severe Pneumonia in Mice Infected with SARS-CoV," The Journal of Immunology, 2008, vol. 181, pp. 6337-6348.
Yu et al., "Measures for diagnosing and treating infections by a novel coronavirus responsible for a pneumonia outbreak originating in Wuhan, China," Microbes and Infection, 2020, vol. 22, pp. 74-79.
Zhang et al., "Antibody Responses Against SARS Coronavirus Are Correlated With Disease Outcome of Infected Individuals," Journal of Medical Virology, 2006, vol. 78, pp. 1-8.
Zhang et al., "Clinical characteristics of 82 death cases with COVID-19," medRxiv, Feb. 27, 2020, pp. 1-30.
Zhou et al., "A Single Asparagine-Linked Glycosylation Site of the Severe Acute Respiratory Syndrome Coronavirus Spike Glycoprotein Facilitates Inhibition by Mannose-Binding Lectin through Multiple Mechanisms," Journal of Virology, Sep. 2010, vol. 84, No. 17, pp. 8753-8764.
Zhou et al., "Active Replication of Middle East Respiratory Syndrome Coronavirus and Aberrant Induction of Inflammatory Cytokines and Chemokines in Human Macrophages: Implications for Pathogenesis," The Journal of Infectious Diseases, May 2014, vol. 209, pp. 1331-1342.
Zhou et al., "A pneumonia outbreak associated with a new coronavirus of probable bat origin," Nature, Mar. 12, 2020, vol. 579, pp. 270-273.
Zhou et al., "Clinical course and risk factors for mortality of adult inpatients with COVID-19 in Wuhan, China: a retrospective cohort study," The Lancet, Mar. 28, 2020, vol. 395, pp. 1054-1062.
International Preliminary Report on Patentability dated Sep. 22, 2022 in corresponding International Patent Application No. PCT/EP2020/058878 (9 pages).
Office Action dated May 5, 2023 in corresponding Brazilian Patent Application No. BR112022019090-5 (9 pages).
English translation of the Office Action dated May 5, 2023 in corresponding Brazilian Patent Application No. BR112022019090-5 (8 pages).
Yadav et al., "Fifty Years of Research in ARDS: Is Acute Respiratory Distress Syndrome a Preventable Disease?," American Journal of Respiratory and Critical Care Medicine, Mar. 2017, vol. 195, No. 6, pp. 725-736.
Annane et al., "Intravenous ravulizumab in mechanically ventilated patients hospitalised with severe COVID-19: a phase 3, multicentre, open-label, randomised controlled trial," The Lancet: Respiratory Medicine, Dec. 2023, vol. 11, No. 12, pp. 1051-1063.
Anonymous, "Emergency Use Authorization (EUA) for Vilobelimab (IFX-1) Center for Drug Evaluation and Research (CDER) Review," Feb. 1, 2023, 105 pages, Retrieved from the Internet on Dec. 5, 2023; URL: <https://www.gohibic.com/>.
Mourvillier et al., "LB1529. Randomized, Controlled Phase 3 Study of anti-C5a Vilobelimab's Effect on Mortality in Critically Ill COVID-19 Patients: A Therapy for Viral Pneumonia," Open Forum Infectious Diseases, Dec. 2022, vol. 9, Suppl. 2, p. S925.
Carvelli et al., "Association of COVID-19 inflammation with activation of the C5a-C5aR1 axis," Nature, Dec. 3, 2020, vol. 588, pp. 146-150.
Jiang et al., "Blockade of the C5a-C5aR axis alleviates lung damage in hDPP4-transgenic mice infected with MERS-CoV," Emerging Microbes & Infections, 2018, vol. 7, Article No. 77, pp. 1-12.
Sun et al., "Treatment With Anti-C5a Antibody Improves the Outcome of H7N9 Virus Infection in African Green Monkeys," Clinical Infectious Diseases, Feb. 15, 2015, vol. 60, No. 4, pp. 586-595.
Vlaar et al., "Anti-C5a antibody IFX-1 (vilobelimab) treatment versus best supportive care for patients with severe COVID-19 (PANAMO): an exploratory, open-label, phase 2 randomised controlled trial," The Lancet Rheumatology, Dec. 2020, vol. 2, pp. e764-e773.
Wang et al., "The role of C5a in acute lung injury induced by highly pathogenic viral infections," Emerging Microbes & Infections, 2015, vol. 4, No. 1, pp. 1-7.
International Search Report and Written Opinion mailed Jan. 21, 2021 in corresponding International PCT Patent Application No. PCT/EP2020/058878 (13 pages).

(56) References Cited

OTHER PUBLICATIONS

Dang et al., "Epitope mapping of monoclonal antibodies: a comprehensive comparison of different technologies," mAbs, 2023, vol. 15, No. 1, pp. 1-12.
Office Action dated Oct. 13, 2025, in corresponding European Patent Application No. 20716729.7 (9 pages).

* cited by examiner

Patient #1

Patient #2

6 Days before 11 Days after 20 Days after

2 Days before 3 Days after 12 Days after

Days before or after the 1st dose of anti-C5a antibody

METHOD OF TREATING CONDITIONS, REDUCING AN INFLAMMATORY RESPONSE, OR IMPROVING ORGAN FUNCTION IN A SUBJECT HAVING A CORONA VIRUS INFECTION BY ADMINISTERING AN INHIBITOR OF C5a ACTIVITY

CROSS-REFERENCE TO RELATED APPLICATIONS

This application is the U.S. National Stage Application, pursuant to 35 U.S.C. § 371 of PCT International Application No. PCT/EP2020/058878, filed Mar. 27, 2020, designating the United States and published in English, the entire contents of which are incorporated herein by reference in its entirety.

The present invention relates to an inhibitor of C5a activity medical condition caused by or associated with infection with a corona virus, wherein the medical condition is preferably (i) pneumonia, and/or (ii) fever. The invention also relates to the use of an inhibitor of C5a activity in the reduction of an inflammatory response in a subject suffering from a corona virus infection. The invention further relates to an inhibitor of C5a activity for use in the improvement of organ function, in particular lung function and/or hepatic function, in a subject suffering from a corona virus infection.

SEQUENCE LISTING

This application contains a Sequence Listing which has been submitted electronically in ASCII format and is hereby incorporated by reference in its entirety. The Sequence Listing ASCII file, created on Jan. 28, 2026, is named 180399-010500_Amended_SL 2026.txt and is 15,639 bytes in size.

BACKGROUND OF THE INVENTION

C5a

C5a is cleaved from C5 upon complement activation. Among the complement activation products, C5a is one of the most potent inflammatory peptides, with a broad spectrum of functions (Guo R F, and Ward P A. 2005. Annu. Rev. Immunol. 23:821-852). C5a is a glycoprotein present in the blood of healthy humans with a molecular weight of 11.2 kDa. The polypeptide portion of C5a contains 74 amino acids, accounting for a molecular weight of 8.2 kDa while the carbohydrate portion accounts for approximately 3 kDa. C5a exerts its effects through the high-affinity C5a receptors (C5aR and C5L2) (Ward P A. 2009. J. Mol. Med. 87 (4): 375-378). C5aR belongs to the rhodopsin-type family of G-protein-coupled receptors with seven transmembrane segments; C5L2 is similar but is not G-protein-coupled. It is currently believed that C5a exerts its biological functions primarily through C5a-C5aR interaction, as few biological responses have been found for C5a-C5L2 interaction. C5aR is widely expressed on myeloid cells including neutrophils, eosinophils, basophils, and monocytes, and non-myeloid cells in many organs, especially in the lung and liver, indicative of the importance of C5a/C5aR signaling. C5a has a variety of biological functions (Guo and Ward, 2005, supra). C5a is a strong chemoattractant for neutrophils and also has chemotactic activity for monocytes and macrophages. C5a causes an oxidative burst (02 consumption) in neutrophils and enhances phagocytosis and release of granular enzymes. C5a has also been found to be a vasodilator.

C5a has been shown to be involved in modulation of cytokine expression from various cell types, to enhance expression of adhesion molecules on neutrophils. It is found that C5a becomes highly detrimental when it is overly produced in the disease settings, as it is a strong inducer and enhancer for inflammatory responses functioning in the up-stream of the inflammatory reaction chain. High doses of C5a can lead to nonspecific chemotactic "desensitization" for neutrophils, thereby causing broad dysfunction (Huber-Lang M et al. 2001. J. Immunol. 166 (2): 1193-1199).

C5a has been reported to exert numerous pro-inflammatory responses. For example, C5a stimulates the synthesis and release from human leukocytes of pro-inflammatory cytokines such as TNF-α, IL-1B, IL-6, IL-8, and macrophage migration inhibitory factor (MIF) (Hopken U et al. 1996. Eur J Immunol 26 (5): 1103-1109; Riedemann N C et al. 2004. J Immunol 173 (2): 1355-1359; Strieter R M et al. 1992. Am J Pathol 141 (2): 397-407). C5a produces a strong synergistic effect with LPS in production of TNF-α, macrophage inflammatory protein (MIP)-2, cytokine-induced neutrophil chemoattractant (CINC)-1, and IL-1ß in alveolar epithelial cells (Riedemann N C et al. 2002. J. Immunol. 168 (4): 1919-1925; Rittirsch D et al. 2008. Nat Rev Immunol 8 (10): 776-787).

Blockade of C5a has also been proven to be protective in experimental models of sepsis and in many other models of inflammation such as ischemia/reperfusion injury, renal disease, graft rejection, malaria, rheumatoid arthritis, infectious bowel disease, inflammatory lung disease, lupus-like autoimmune diseases, neurodegenerative disease, etc. in various species as partially reviewed under Klos A. et al (Klos A. et al. 2009. Mol Immunol 46 (14): 2753-2766) and Allegretti M. et al (Allegretti M et al. 2005. Curr Med Chem 12 (2): 217-236). Moreover, it has been recently discovered that blockade of C5a has shown a strong therapeutic benefit in a tumor model in mice (Markiewski M M et al. 2008. Nat Immunol 9 (11): 1225-1235).

Corona Virus Infection

Different corona virus outbreaks occurred in the last decades worldwide of which in particular three types of virus resulted in diseases with high mortality rates. The Severe Acute Respiratory Syndrome (SARS), the Middle East Respiratory Syndrome (MERS) and lately Coronavirus disease 2019 (COVID-19). The corona virus responsible for these outbreaks where SARS-CoV, MERS-CoV and SARS-CoV-2, respectively.

An outbreak of coronavirus disease 2019 (COVID-19) caused by the 2019 novel coronavirus, also known as severe acute respiratory syndrome coronavirus 2 (SARS-CoV-2), was first identified in Wuhan, Hubei Province, China in December 2019, and has since become a serious public health threat [Chen et al. 2020; medRxiv, 2020: p. 2020.02.16.20023903; Chen et al [2] 2020, The Lancet, 2020. 395 (10223): p. 507-513; Yu et al 2020, Microbes and Infection, 2020. 22 (2): p. 74-79]. The case fatality rate, as of Mar. 23, 2020, is 4.02% in China, which accounts for both the 4.66% fatality rate in the Hubei province and the 0.89% fatality rate outside the Hubei province. The much lower fatality rate outside the Hubei province is believed to be mainly attributable to improved medical attention including early diagnosis and timely and improved medical care [Zhao et al, medRxiv, 2020: p. 2020.03.17.20037572]. There is a sustained transmission in countries outside of China. As COVID-19 continues to spread, the demand for various levels of medical care will surge. Therefore, to effectively reduce the fatality rate, prevention of common (mild) viral pneumonia development to a severe form and severe pneumonia development into a critically ill condition or ARDS should be a focus of medical treatment.

COVID-19 could present with features of long non-symptomatic latency which might be a main contributing factor to a relatively high transmissibility compared to the other previously occurring deadly coronavirus infections, severe acute respiratory syndrome (SARS) and Middle East respiratory syndrome (MERS). COVID-19 patients typically present with flu-like symptoms such as fever or signs of lower respiratory tract illness including dry cough and shortness of breath [Chen et al [2] supra; Chang et al JAMA, 2020; Wang et al. AMA, 2020; Xiao et al Journal of Medical Virology, 2020]. The incubation time prior to symptoms is estimated to be somewhere between 2 to 14 days after virus exposure according to an analysis from the Center for Disease Control and Prevention (CDC) of the United States. With the progression of disease into a severe form, it often affects multiple organs' functions including the lung, heart, liver, and coagulation system among others [Liu et al medRxiv, 2020: p. 2020.02.10.20021584; Fan et al. medRxiv, 2020: p. 2020.02.26.20026971; Tang et al Journal of Thrombosis and Haemostasis, 2020.]. As such, death is typically caused by respiratory failure and multiple organ dysfunctions similar to other viral pneumonia-induced sepsis [Zhang et al medRxiv, 2020: p. 2020.02.26.20028191]. Sepsis and ARDS mostly occur in the second week upon disease onset; the battle for life often takes place in the third week of severe illness [Zhou et al The Lancet, 2020].

Accumulating data indicates that older age, underlying health conditions (e.g. cardiovascular issues) and compromised immune systems are the important risk factors for the potential of developing a more severe form of disease onset and worse outcomes [Huang et al The Lancet, 2020. 395 (10223): p. 497-506]. The top three comorbidities alongside COVID-19 that are associated with a high death rate are hypertension, diabetes and coronary heart disease [Zhou et al supra]. There is in an urgent need to develop a safe and effective treatment strategy for COVID-19 patients, especially for the ones that have the above-mentioned risk factors or comorbidities.

COVID-19 has become a serious health threat to mankind, especially to elders. COVID-19 can be characterized by a dual play of viral inflammation and immune-mediated injury. Based on the herein disclosed preclinical as well as clinical findings, we propose a pathogenic "complement storm" event occurring in the progression of corona virus infection, in particular COVID-19. Blockade by anti-C5a therapy offers an efficacious therapeutic effect in animal models and a preliminary testing in COVID-19 patients. Anti-C5a approach is a viable strategy in battling COVID-19 in patients with progressing/worsening mild forms as well as severe forms of the disease.

TECHNICAL PROBLEMS UNDERLYING THE PRESENT INVENTION

One of the problems underlying the invention was the provision of therapeutic approaches for the treatment of pneumonia caused by the novel SARS-CoV2 virus.

So far it has not been studied whether an anti-C5a treatment would be effective in the treatment of pneumonia caused by corona virus, let alone the high mortality strains SARS-CoV, MERS-CoV and SARS-CoV-2.

The inventors of the instant application have applied IFX-1, a highly potent neutralizing mAb against human C5a to explore the therapeutic potential of complement inhibition in the treatment of H7N9 virus-induced severe pneumonia. To our knowledge, this is the first time that an anti-C5a treatment of pneumonia and associated symptoms in a subject suffering from corona virus infection has been studied.

The data disclosed in the experimental section below demonstrate that excessive complement activation occurs in the infection with various corona virus types, including SARS-CoV, MERS-CoV and SARS-CoV-2.

The present inventors have found that anti-C5a treatment in SARS-CoV-2 infected human patients substantially attenuated the main symptoms of COVID-19, i.e. reduced fever, improved lymphocyte count, reduced CRP levels and improved organ function in particular lung and liver function as seen by the normalization of blood oxygenation and ALT/AST levels. All these effects were seen with fast resolution upon application of anti-C5a treatment.

In addition the inventors disclose a multitude of experiments that provide mechanistic insight on how infection with different corona virus strains result in massive complement activation.

These results suggest that complement inhibition, in particular C5a inhibition, is a highly promising strategy for a treatment of corona virus caused disease, in particular corona virus caused respiratory syndromes.

The above overview does not necessarily describe all advantages associated with and problems solved by the present invention.

SUMMARY OF THE INVENTION

In a first aspect the present invention relates to an inhibitor of C5a activity for use in the treatment of a medical condition caused by or associated with infection with a corona virus, wherein the medical condition is preferably (i) pneumonia, and/or (ii) fever.

In a second aspect the present invention relates to an inhibitor of C5a activity for use in the reduction of an inflammatory response in a subject suffering from a corona virus infection.

In a third aspect the present invention relates to an inhibitor of C5a activity for use in the improvement of organ function, in particular lung function and/or hepatic function, in a subject suffering from a corona virus infection.

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Several documents (for example: patents, patent applications, scientific publications, manufacturer's specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

Sequences: All sequences referred to herein are disclosed in the attached sequence listing that, with its whole content and disclosure, is a part of this specification.

In the context of the present invention, C5a particularly refers to human C5a. Human C5a is a 74 amino acid peptide with the following amino acid sequence:

```
                                        (SEQ ID NO: 1)
TLQKKIEEIA AKYKHSVVKK CCYDGACVNN DETCEQRAAR
ISLGPRCIKA FTECCVVASQ LRANISHKDM QLGR
```

The amino acid sequence of human C5 can be found under the accession number UniProtKB P01031 (CO5_HUMAN).

As used herein, the term "inhibitor of C5a activity" refers to any compound that in any way reduces the activity of C5a. This activity reduction can be achieved by directly or indirectly lowering the concentration of C5a, or by reducing the activity of C5a, or by preventing C5a from exerting its effects on one or more of its receptors (e.g. on C5aR or C5L2), or by reducing the concentration or activity of one or more receptors of C5a.

In the context of the present invention, the expression "C5a receptor" refers to any potential C5a binding ligand on the cell surface, especially to any receptor protein to which C5a may bind and elicit a reaction on said receptor (e.g. activation or inhibition of the receptor). The term "C5a receptor" particularly encompasses the two receptors C5aR and C5L2. Alternative names for C5aR are C5aR1 and CD88. An alternative name for C5L2 is C5aR2.

Certain embodiments of the present invention refer to an inhibitor of C5a that interferes with a C5a receptor (e.g. by binding to a C5a receptor, or by blocking expression of a C5a receptor). In these contexts, the term "a C5a receptor" can refer to (i) C5aR or to (ii) C5L2 or to (iii) both C5aR and C5L2. This means that some inhibitors of C5a interfere with only one of the C5a receptors (i.e. either C5aR or C5L2), while other inhibitors of C5a interfere with both C5a receptors (i.e. both C5aR and C5L2).

In the context of the present invention, the expression "protein ligand" refers to any molecule composed of amino acids linked by peptide bonds, irrespective of the total size of the molecule, and that is capable of specifically binding to another molecule. Accordingly, the expression "protein ligand" comprises oligopeptides (≤100 amino acids) and polypeptides (>100 amino acids). The expression "protein ligand" also comprises cyclic peptides, irrespective of their size. The expression "protein ligand" particularly encompasses antibodies, antigen-binding fragments of antibodies, antibody-like proteins, and peptidomimetics.

As used herein, a first compound (e.g. a protein ligand or nucleic acid aptamer) is considered to "bind" to a second compound (e.g. a target protein), if it has a dissociation constant $K_d$ to said second compound of 1 mM or less, preferably 100 μM or less, preferably 50 μM or less, preferably 30 μM or less, preferably 20 μM or less, preferably 10 UM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

The term "binding" according to the invention preferably relates to a specific binding. "Specific binding" means that a compound (e.g. a protein ligand or nucleic acid aptamer) binds stronger to a target such as an epitope for which it is specific compared to the binding to another target. A compound binds stronger to a first target compared to a second target, if it binds to the first target with a dissociation constant ($K_d$) which is lower than the dissociation constant for the second target. Preferably the dissociation constant ($K_d$) for the target to which the compound binds specifically is more than 10-fold, preferably more than 20-fold, more preferably more than 50-fold, even more preferably more than 100-fold, 200-fold, 500-fold or 1000-fold lower than the dissociation constant ($K_d$) for the target to which the compound does not bind specifically.

As used herein, the term "$K_d$" (usually measured in "mol/L", sometimes abbreviated as "M") is intended to refer to the dissociation equilibrium constant of the particular interaction between a compound (e.g. a protein ligand) and a target molecule.

Methods for determining binding affinities of compounds, i.e. for determining the dissociation constant $K_d$, are known to a person of ordinary skill in the art and can be selected for instance from the following methods known in the art: Surface Plasmon Resonance (SPR) based technology, Bio-layer interferometry (BLI), enzyme-linked immunosorbent assay (ELISA), flow cytometry, isothermal titration calorimetry (ITC), analytical ultracentrifugation, radioimmunoassay (RIA or IRMA) and enhanced chemiluminescence (ECL). Typically, the dissociation constant $K_d$ is determined at 20° C., 25° C., 30° C., or 37° C. If not specifically indicated otherwise, the $K_d$ values recited herein are determined at 20° C. by ELISA.

An "epitope", also known as antigenic determinant, is the part of a macromolecule that is recognized by the immune system, specifically by antibodies, B cells, or T cells. As used herein, an "epitope" is the part of a macromolecule capable of binding to a compound (e.g. an antibody or antigen-binding fragment thereof) as described herein. In this context, the term "binding" preferably relates to a specific binding. Epitopes usually consist of chemically active surface groupings of molecules such as amino acids or sugar side chains and usually have specific three-dimensional structural characteristics, as well as specific charge characteristics. Conformational and non-conformational epitopes can be distinguished in that the binding to the former but not the latter is lost in the presence of denaturing solvents.

A "paratope" is the part of an antibody that binds to the epitope. In the context of the present invention, a "paratope" is the part of a compound (e.g. a protein ligand) as described herein that binds to the epitope.

The term "antibody" typically refers to a glycoprotein comprising at least two heavy (H) chains and two light (L) chains inter-connected by disulfide bonds, or an antigen-binding portion thereof. The term "antibody" also includes all recombinant forms of antibodies, in particular of the antibodies described herein, e.g. antibodies expressed in prokaryotes, unglycosylated antibodies, antibodies expressed in eukaryotes (e.g. CHO cells), glycosylated antibodies, and any antigen-binding antibody fragments and derivatives as described below. Each heavy chain is comprised of a heavy chain variable region (abbreviated herein as VH or $V_H$) and a heavy chain constant region. Each light chain is comprised of a light chain variable region (abbreviated herein as VL or $V_L$) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) $F(ab')_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341:544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. A further example is a binding-domain immunoglobulin fusion protein comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those skilled in the art, and the fragments are screened for utility in the same manner as are intact antibodies. Further examples of "antigen-binding fragments" are so-called microantibodies, which are derived from single CDRs. For example, Heap et al., 2005, describe a 17 amino acid residue microantibody derived from the heavy chain CDR3 of an antibody directed against the gp120 envelope glycoprotein of HIV-1 (Heap C. J. et al. (2005) Analysis of a 17-amino acid residue, virus-neutralizing microantibody. J. Gen. Virol. 86:1791-1800). Other examples include small antibody mimetics comprising two or more CDR regions that are fused to each other, preferably by cognate framework regions. Such a small antibody mimetic comprising $V_H$ CDR1 and $V_L$ CDR3 linked by the cognate $V_H$ FR2 has been described by Qiu et al., 2007 (Qiu X.-Q. et al. (2007) *Small antibody mimetics comprising two complementary-determining regions and a framework region for tumor targeting*. Nature biotechnology 25 (8): 921-929).

Thus, the term "antibody or antigen-binding fragment thereof", as used herein, refers to immunoglobulin molecules and immunologically active portions of immunoglobulin molecules, i.e. molecules that contain an antigen-binding site that immunospecifically binds an antigen. Also comprised are immunoglobulin-like proteins that are selected through techniques including, for example, phage display to specifically bind to a target molecule or target epitope. The immunoglobulin molecules of the invention can be of any type (e.g., IgG, IgE, IgM, IgD, IgA and IgY), class (e.g., IgG1, IgG2, preferably IgG2a and IgG2b, IgG3, IgG4, IgAQ1 and IgA2) or subclass of immunoglobulin molecule.

Antibodies and antigen-binding fragments thereof usable in the invention may be from any animal origin including birds and mammals. Preferably, the antibodies or fragments are from human, chimpanzee, rodent (e.g. mouse, rat, guinea pig, or rabbit), chicken, turkey, pig, sheep, goat, camel, cow, horse, donkey, cat, or dog origin. It is particularly preferred that the antibodies are of human or murine origin. Antibodies for use in the invention also include chimeric molecules in which an antibody constant region derived from one species, preferably human, is combined with the antigen-binding site derived from another species, e.g. mouse. Moreover, antibodies of the invention include humanized molecules in which the antigen-binding sites of an antibody derived from a non-human species (e.g. from mouse) are combined with constant and framework regions of human origin.

As exemplified herein, antibodies of the invention can be obtained directly from hybridomas which express the antibody, or can be cloned and recombinantly expressed in a host cell (e.g., a CHO cell, or a lymphocytic cell). Further examples of host cells are microorganisms, such as *E. coli*, and fungi, such as yeast. Alternatively, they can be produced recombinantly in a transgenic non-human animal or plant.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another species or class. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human is less likely to elicit an immune response from a human subject when the antibodies are injected than would the constant region from a non-human source. However, the definition is not limited to this particular example.

The term "humanized antibody" refers to a molecule having an antigen-binding site that is substantially derived from an immunoglobulin from a non-human species, wherein the remaining immunoglobulin structure of the molecule is based upon the structure and/or sequence of a human immunoglobulin. The antigen-binding site may either comprise complete variable domains fused onto constant domains or only the complementarity determining regions (CDR) grafted onto appropriate framework regions in the variable domains. Antigen-binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

Different methods for humanizing antibodies are known to the skilled person, as reviewed by Almagro & Fransson, 2008, Frontiers in Bioscience, 13:1619-1633, the content of which is herein incorporated by reference in its entirety. The review article by Almagro & Fransson is briefly summarized in US 2012/0231008 A1 which is the national stage entry of international patent application WO 2011/063980 A1. The contents of US 2012/0231008 A1 and WO 2011/063980 A1 are herein incorporated by reference in their entirety.

As used herein, "human antibodies" include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). Human antibodies of the invention include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g. mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g. from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "transfectoma", as used herein, includes recombinant eukaryotic host cells expressing an antibody, such as CHO cells, NS/0 cells, HEK293 cells, HEK293T cells, plant cells, or fungi, including yeast cells.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

Thus, "antibodies and antigen-binding fragments thereof" suitable for use in the present invention include, but are not limited to, polyclonal, monoclonal, monovalent, bispecific, heteroconjugate, multispecific, recombinant, heterologous, heterohybrid, chimeric, humanized (in particular CDR-grafted), deimmunized, or human antibodies, Fab fragments, Fab' fragments, $F(ab')_2$ fragments, fragments produced by a Fab expression library, Fd, Fv, disulfide-linked Fvs (dsFv), single chain antibodies (e.g. scFv), diabodies or tetrabodies (Holliger P. et al. (1993) Proc. Natl. Acad. Sci. U.S.A. 90 (14), 6444-6448), nanobodies (also known as single domain antibodies), anti-idiotypic (anti-Id) antibodies (including, e.g., anti-Id antibodies to antibodies described herein), and epitope-binding fragments of any of the above.

The antibodies described herein are preferably isolated. An "isolated antibody" as used herein, is intended to refer to an antibody which is substantially free of other antibodies having different antigenic specificities (e.g., an isolated antibody that specifically binds to C5a is substantially free of antibodies that specifically bind antigens other than C5a). An isolated antibody that specifically binds to an epitope, isoform or variant of human C5a may, however, have cross-reactivity to other related antigens, e.g. from other species (e.g. C5a species homologs, such as rat C5a). Moreover, an isolated antibody may be substantially free of other cellular material and/or chemicals. In one embodiment of the invention, a combination of "isolated" monoclonal antibodies relates to antibodies having different specificities and being combined in a well-defined composition.

The term "naturally occurring", as used herein, as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, the term "nucleic acid aptamer" refers to a nucleic acid molecule that has been engineered through repeated rounds of in vitro selection or SELEX (systematic evolution of ligands by exponential enrichment) to bind to a target molecule (for a review see: Brody E. N. and Gold L. (2000), Aptamers as therapeutic and diagnostic agents. J. Biotechnol. 74 (1): 5-13). The nucleic acid aptamer may be a DNA or RNA molecule. The aptamers may contain modifications, e.g. modified nucleotides such as 2'-fluorine-substituted pyrimidines, and/or may comprise one or more nucleotides with L-ribose units (or L-deoxyribose) instead of the standard D-ribose units (or D-deoxyribose units).

As used herein, the term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, affilins, affimers, affitins, alphabodies, anticalins, avimers, DARPins (designed ankyrin repeat proteins), fynomers, Kunitz domain peptides, and monobodies (for review see: Binz H. K. et al. (2005) Engineering novel binding proteins from nonimmunoglobulin domains. Nat. Biotechnol. 23 (10): 1257-1268). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins. Antibody-like proteins are sometimes referred to as "peptide aptamers" or as "antibody mimetics".

As used herein, a "peptidomimetic" is a small protein-like chain designed to mimic a peptide. Peptidomimetics typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of non-natural amino acids).

In the context of the present invention, the term "small molecule" refers to a molecule with a molecular weight of 2 kDa or less, preferably with a molecular weight of 1 kDa or less. The term "small molecule" particularly refers to molecules that are neither oligopeptides nor oligonucleotides.

In the context of the present invention, the general expression "wherein A competes with B for binding to C", (e.g. in the expression "wherein said antibody or antigen-binding fragment thereof competes with one of the antibodies indicated under (a) for binding to C5a") is used to define the binding properties of the compound listed in position A. Said compound A binds to C and compound B also binds to C but compound A and compound B cannot bind to C at the same time; i.e. A and B bind to the same epitope (or at least to overlapping epitopes) on C. Such competition in binding can be determined by competitive ELISA or by Surface Plasmon Resonance (SPR) based technology or by any of the other techniques listed above in the context of the determination of binding affinities. If not explicitly stated otherwise, the competing binding properties of a compound are determined by ELISA at 20° C. using equimolar concentrations of the two competing compounds.

IFX-1 (alternative name: CaCP29; InflaRx GmbH, Germany) is an antibody specifically binding to C5a. The CDR sequences and FR sequences of IFX-1 are disclosed in WO 2015/140304 A1 (Table 3), the content of which is hereby incorporated by reference in its entirety. It comprises the variable heavy chain sequence according to SEQ ID NO: 34 and the variable light chain sequence according to SEQ ID NO: 359

INab708 (InflaRx GmbH, Germany) is another antibody specifically binding to C5a. The CDR sequences and FR sequences of INab708 are also disclosed in WO 2015/140304 A1 (Table 3), the content of which is incorporated by reference in its entirety. It comprises the variable heavy chain sequence according to SEQ ID NO: 36 and the variable light chain sequence according to SEQ ID NO: 37.

MEDI-7814 (MedImmune) is a recombinant humanized anti-C5a antibody. The crystal structure of the human C5a in complex with MEDI-7814 is available in the RCSB Protein Data Bank under 4UU9 (DOI: 10.2210/pdb4uu9/pdb).

ALXN-1007 (Alexion) is a humanized anti-C5a antibody.

NOX-D21 (Noxxon) is a PEGylated mixed L-RNA/DNA-aptamer (SPIEGELMER™) with the sequence 40 kDaPEG-aminohexyl-GCG AUG (dU)GG UGG UGA AGG GUU GUU GGG (dU)GU CGA CGC A(dC)G C (SEQ ID NO: 34). NOX-D21 targets C5a (Hyzewicz J, Tanihata J, Kuraoka M, Nitahara-Kasahara Y, Beylier T, Ruegg U T, Vater A, and Takeda S. 2017. *Low-Intensity Training and the C5a Complement Antagonist NOX-D21 Rescue the mdx Phenotype through Modulation of Inflammation.* Am. J. Pathol., 187 (5): 1147-1161; electronically published ahead of print: Mar. 18, 2017).

Eculizumab (Alternative names: SOLIRIS™, 5G1-1; h5G1.1; Alexion Pharmaceuticals) is a recombinant humanized monoclonal IgG2/4κ antibody produced by murine myeloma cell culture and purified by standard bioprocess technology. Eculizumab specifically binds to human C5. Eculizumab contains human constant regions from human IgG2 sequences and human IgG4 sequences and murine complementarity-determining regions grafted onto the human framework light- and heavy-chain variable regions. Eculizumab is composed of two 448 amino acid heavy chains and two 214 amino acid light chains and has a molecular weight of approximately 148 kDa. The heavy chain and light chain of eculizumab are disclosed, for example, in WO 2016/061066 A1 as SEQ ID NO: 1 and SEQ ID NO: 34, respectively. Nucleic acids that encode the heavy and light chains of eculizumab are disclosed, for example, in U.S. Pat. No. 6,355,245.

ALXN1210 (Alternative name: BNJ441; Alexion Pharmaceuticals) is an anti-C5 antibody. The heavy and light chains of ALXN1210 are disclosed in WO 2016/209956 A1 as SEQ ID NOs: 14 and 11, respectively.

ALXN5500 (Alexion) is a humanized anti-C5 antibody. It is a next-generation eculizumab candidate.

LFG316 (Alternative name: Tesidolumab, NOV-4; Morphosys, Novartis) is an anti-C5 antibody.

COVERSIN™ (alternative names: Nomacompan, EV 576; PAS-COVERSIN; rEV 576; Tissue targeted COVERSIN™—Akari; Akari Therapeutics, Evolutec) is a recombinant protein molecule (16.7 kDa) derived from a salivary molecule from the *Ornithodros moubata* tick where it assists the parasite to feed without provoking a host immunological response. The amino acid sequence of the EV576 protein (i.e. COVERSIN™) as well as its coding nucleotide sequence are shown in FIG. 2 of WO 2008/029167. COVERSIN™ binds to C5.

RA101495 (Ra Pharma) is a macrocyclic synthetic peptide inhibitor of C5 (Ricardo A, Arata M, DeMarco S, Dhamnaskar K, Hammer R, Fridkis-Hareli M, Rajagopal V, Seyb K, Tang G-Q, Tobe S and Treco D. 2015. *Preclinical*

*Evaluation of RA101495, a Potent Cyclic Peptide Inhibitor of C5 for the Treatment of Paroxysmal Nocturnal Hemoglobinuria*. Blood 126:939).

ZIMURA® (Alternative names: Avacincaptad pegol, Anti-C5 aptamer; ARC-187; ARC-1905; Avacincaptad pegol sodium; OphthoTech Corporation, Archemix Corporation) is a pegylated RNA aptamer that inhibits complement factor C5. The nucleotide sequence of ARC1905 (i.e. ZIMURAR) is shown, for example, in WO 2005/079363 A2 as SEQ ID NO: 67, and its structure is shown in FIG. 22 of WO 2005/079363 A2.

AMY-201 (Amyndas Pharmaceuticals) is an engineered form of Factor H that directly links the regulatory and surface-recognition domains; thus, it is a sort of mini-FH molecule.

Mirococept (alternative names: APT070 and APT 070C; originator: Adprotech; developer: Inflazyme Pharmaceuticals) consists of the first three short consensus domains of human complement receptor 1, manufactured in recombinant bacteria and modified with a membrane-targeting amphiphilic peptide based on the naturally occurring membrane-bound myristoyl-electrostatic switch peptide (Souza D G, Esser D, Bradford R, Vieira A T, and Teixeira M M. 2005. *APT070 (Mirococept), a membrane-localised complement inhibitor, inhibits inflammatory responses that follow intestinal ischaemia and reperfusion injury*. Br J Pharmacol 145 (8): 1027-1034).

BikacioMab (Novelmed) is an $F(ab)_2$ fragment of an anti-factor Bb antibody termed NM001. Antibody NM001 is produced by hybridoma cell line 1D3 deposited under ATCC accession number PTA-8543.

Lampalizumab (alternative names: Anti-factor D Fab; FCFD4514S; RG7417; TNX-234; originator: Tanox, Developer: Genentech) is a humanized anti-Factor D Fab fragment that inhibits Factor D and the alternative complement pathway, through binding to an exosite on factor D.

ALN-CC5 (Alnylam) is an RNAi therapeutic targeting human, primate and rodent C5. Exemplary iRNA compositions targeting the C5 gene are described in WO 2016/044419.

Avacopan (also known by the name CCX168; Chemocentryx) is a small molecule (MW=581.66 g/mol) that has a structure according to formula I:

I

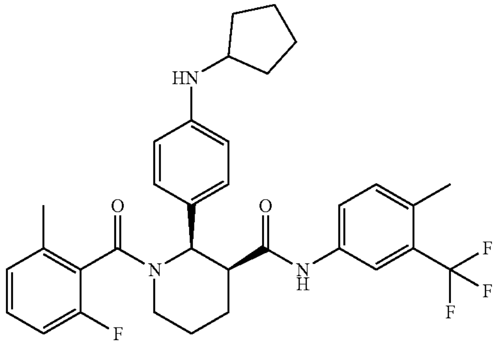

The IUPAC/Chemical name of avacopan is (2R,3S)-2-[4-(cyclopentylamino)phenyl]-1-(2-fluoro-6-methylbenzoyl)-N-[4-methyl-3-(trifluoromethyl)phenyl]piperidine-3-carboxamide. Avacopan is a selective inhibitor of C5aR. In the context of the present invention, the term "avacopan" refers to the compound according to formula I as well as to physiologically tolerable salts thereof.

Compounds similar to Avacopan that are also suitable for practicing the present invention are disclosed in international patent applications WO 2010/075257 A1 and WO 2011/163640 A1, the contents of which are herein incorporated by reference in their entirety. Thus, in some embodiments the inhibitor of C5a activity is a compound having the formula II

II

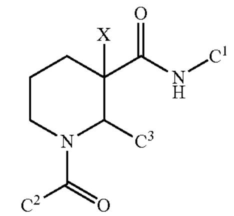

and pharmaceutically acceptable salts, hydrates and rotomers thereof; wherein $C^1$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^1$ substituents;

$C^2$ is selected from the group consisting of aryl and heteroaryl, wherein the heteroaryl group has from 1-3 heteroatoms as ring members selected from N, O and S; and wherein said aryl and heteroaryl groups are optionally substituted with from 1 to 3 $R^2$ substituents; 20

$C^3$ is selected from the group consisting of $C_{1-8}$ alkyl or heteroalkyl, $C_{3-8}$ cycloalkyl, $C_{3-8}$ cycloalkyl-$C_{1-4}$ alkyl, aryl, aryl-$C_{1-4}$ alkyl, heteroaryl, heteroaryl-$C_{1-4}$ alkyl, heterocycloalkyl or heterocycloalkyl-$C_{1-4}$ alkyl, wherein the heterocycloalkyl group or portion has from 1-3 heteroatoms selected from N, O and S, and wherein the heteroaryl group has from 1-3 heteroatoms as ring members selected from N, O and S, and each $C^3$ is optionally substituted with from 1-3 $R^3$ substituents;

each $R^1$ is independently selected from the group consisting of halogen, —CN, —$R^c$, —$CO_2R^a$, —$CONR^aR^b$, —$C(O)R^a$, —$OC(O)NR^aR^b$, —$NR^bC(O)R^a$, —$NR^bC(O)_2R^c$, —$NR^a$—$C(O)NR^aR^b$, —$NR^aC(O)NR^aR^b$, —$NR^aR^b$, —$OR^a$, and —$S(O)_2NR^aR^b$; wherein each $R^a$ and $R^b$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each Reis independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and cyclic portions of $R^a$, $R^b$ and $R^c$ are optionally further substituted with from one to three halogen, hydroxy, methyl, amino, alkylamino and dialkylamino groups; and optionally when two $R^1$ substituents are on adjacent atoms, are combined to form a fused five or six-membered carbocyclic or heterocyclic ring;

each $R^2$ is independently selected from the group consisting of halogen, —CN, —$NO_2$, —$R^f$, —$CO_2R^d$, —$CONR^dR^e$, —$C(O)R^d$, —$OC(O)NR^dR^e$, —$NR^eC(O)R^d$, —$NR^eC(O)_2R^f$, —$NR^eC(O)NR_4R^e$, —$NR^dC(O)NR^dR^e$, —$NR^dR^e$, —$OR_4$, and —$S(O)_2NR^dR^e$; wherein each $R^d$ and $R^e$ is independently selected from hydrogen, $C_{1-8}$ alkyl, and $C_{1-8}$ haloalkyl, or when attached to the same nitrogen atom can be combined with the nitrogen atom to form a five or six-membered ring having from 0 to 2 additional heteroatoms as ring members selected from N, O or S, and is optionally substituted with one or two oxo; each R is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl, and wherein the aliphatic and cyclic portions of $R^d$, $R^e$ and $R^f$ are optionally further substituted with from one to three halogen, hydroxy, methyl, amino, alkylamino and dialkylamino groups, and optionally when two $R^2$ groups are on adjacent atoms, they are combined to form a five- or six-membered ring;

each $R^3$ is independently selected from the group consisting of halogen, —CN, —$R^i$, —$CO_2R^g$, —$CONR^gR^h$, —$C(O)R^g$, —$C(O)R^i$, —$OC(O)NR^gR^h$, —$NR^hC(O)R^g$, —$NR^hCO_2R^i$, —$NR^gC(O)NR^gR^h$, —$NR^gR^h$, —$OR^g$, —$OR^j$, —$S(O)_2NR^gR^h$, —$X^4$—$R^j$, —NH—$X^4$—$R^j$, —O—$X^4$—$R^j$, —$X^4$—$NR^gR^h$, —$X^4$—$NHR^j$, —$X^4$—$CONR^gR^h$, —$X^4$—$NR^hC(O)R^g$, —$X^4$—$CO_2R^g$, —O—$X^4$—$CO_2R^g$, —NH—$X^4$—$CO_2R^g$, —$X^4$—$NR^hCO_2R^i$, —O—$X^4$—$NR^hCO_2R^i$, —$NHR^j$ and —$NHCH_2R^j$, wherein $X^4$ is a $C_{1-4}$ alkylene; each $R^g$ and $R^h$ is independently selected from hydrogen, $C_{1-8}$ alkyl or heteroalkyl, $C_{3-6}$ cycloalkyl and $C_{1-8}$ haloalkyl, or when attached to the same nitrogen atom can be combined with the nitrogen atom to form a four-, five- or six-membered ring having from 0 to 2 additional heteroatoms as ring members selected from N, O or S and is optionally substituted with one or two oxo; each $R^i$ is independently selected from the group consisting of $C_{1-8}$ alkyl or heteroalkyl, $C_{1-8}$ haloalkyl, $C_{3-6}$ cycloalkyl, heterocycloalkyl, aryl and heteroaryl; and each $R^j$ is selected from the group consisting of $C_{3-6}$ cycloalkyl, imidazolyl, pyrimidinyl, pyrrolinyl, piperidinyl, morpholinyl, tetrahydrofuranyl, tetrahydropyranyl, and S,S-dioxo-tetrahydrothiopyranyl, and wherein the aliphatic and cyclic portions of $R^g$, $R^h$, $R^i$ and $R^j$ are optionally further substituted with from one to three halogen, methyl, $CF_3$, hydroxy, $C_{1-4}$ alkoxy, $C_{1-4}$ alkoxy-$C_{1-4}$ alkyl, —C(O)O—$C_{1-8}$ alkyl, amino, alkylamino and dialkylamino groups, and optionally when two $R^3$ groups are on adjacent atoms, they are combined to form a five- or six-membered ring; and X is hydrogen or $CH_3$.

Compounds that are similar to Avacopan but have an improved solubility profile are disclosed in WO 2017/176620 A2, the content of which is herein incorporated by reference in its entirety. Thus, in some other embodiments the inhibitor of C5a activity is a compound of the following formula III:

III

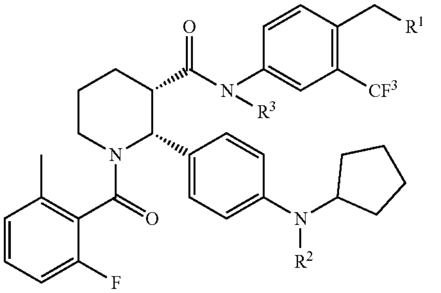

or a pharmaceutically acceptable salt thereof, wherein:

$R^1$ is selected from the group consisting of H, —O—$CH_2$—O—$P(O)OR^aOR^b$, —O—C(O)—$C_{1-6}$ alkylene-$L^2$-$X^1$, O—$P(O)OR^aOR^b$, and —O—C(O)-$A^1$-($C_{1-3}$ alkylene)$_n$-$C_{4-7}$ heterocyclyl wherein the $C_{4-7}$ heterocyclyl is optionally substituted with 1 to 6 $R^c$ groups;

$A^1$ is selected from the group consisting of $C_{6-10}$ aryl, $C_{3-10}$ cycloalkyl, $C_{5-10}$ heteroaryl and $C_{5-10}$ heterocyclyl, each of which is optionally substituted with 1 to 5 $R^x$ which can be the same or different;

n=0 or 1;

$L^2$ is independently selected from the group consisting of a bond, —O—C(O)—$C_{1-6}$ alkylene-, and —$NR^d$—C(O)—$C_{1-6}$ alkylene-;

$X^1$ is independently selected from the group consisting of —$NR^eR^f$, —$P(O)OR^aOR^b$, —O—$P(O)OR^aOR^b$, and —$CO_2H$;

$R^2$ is selected from the group consisting of H, -$L^3$-$C_{1-6}$ alkylene-$L^4$-$X^2$, -$L^3$-($C_{1-6}$ alkylene)$_m$-$A^2$-$X^2$, —$P(O)OR^aOC(O)$—$C_{1-6}$ alkyl, —$P(O)OR^aNR^gR^h$ and —$P(O)OR^aOR^b$;

$L^3$ is independently selected from the group consisting of —C(O)—O—, and —C(O)—;

$L^4$ is independently selected from the group consisting of a bond, —O—C(O)—$C_{2-6}$ alkenylene-, —O—C(O)—$C_{1-6}$ alkylene-, and —$NR^d$—C(O)—$C_{1-6}$ alkylene-wherein the $C_{1-6}$ alkylene in —$NR^d$—C(O)—$C_{1-6}$ alkylene- and —O—C(O)—$C_{1-6}$ alkylene- is optionally substituted with $NR^eR^f$, $X^2$ is independently selected from the group consisting of —$NR^kR^l$, —$P(O)OR^aOR^b$, —O—$P(O)OR^aOR^b$, and —$CO_2H$;

m=0 or 1;

$A^2$ is selected from the group consisting of $C_{6-10}$ aryl, $C_{3-10}$ cycloalkyl, $C_{5-10}$ heteroaryl and $C_{5-10}$ heterocyclyl, each of which is optionally substituted with 1 to 5 $R^x$ which can be the same or different;

$R^3$ is H or -$L^5$-$P(O)OR^aOR^b$ wherein L5 is independently selected from the group consisting of a bond and —$CH_2$—O—;

each $R^x$ is independently selected from the group consisting of halogen, $C_{1-6}$ alkyl, $C_{1-6}$ haloalkyl, $C_{1-6}$ heteroalkyl, CN, $NR^yR^z$, $SR^y$ and $OR^y$;

each $R^e$ is independently selected from the group consisting of halogen, $C_{1-6}$ alkyl, $C_{1-6}$ haloalkyl, $C_{1-6}$ heteroalkyl, CN, $NR^yR^z$, $SR^y$ and $OR^y$;

each $R^a$, $R^b$, $R^d$, $R^e$, $R^f$, $R^g$, $R^k$, $R^l$, $R^y$ and $R^z$ is independently selected from the group consisting of H and $C_{1-6}$ alkyl;

each $R^h$ is independently selected from the group consisting of H and $C_{1-6}$ alkyl wherein the $C_{1-6}$ alkyl is optionally substituted with 1 to 5 substituents independently selected from $CO_2H$, $NR^iR^j$, $C_{6-10}$ aryl, $C_{3-10}$ cycloalkyl, $C_{5-10}$ heteroaryl and $C_{5-10}$ heterocyclyl, wherein each $R^i$ and $R^j$ is independently H or $C_{1-6}$ alkyl;

wherein two of $R^1$, $R^2$ and $R^3$ are H, and one of $R^1$, $R^2$ and $R^3$ is other than H.

PMX-53 is a potent antagonist of C5aR (CD88). It is a circular peptide composed of six amino acids, with the following sequence: Ac-Phe-cyclo (Orn-Pro-D-Cha-Trp-Arg) with a lactam bridge between Orn-2 and Arg-6. Since PMX-53 contains at least one D-amino acid (i.e. D-Cha), it is not included the enclosed sequence listing of this application. PMX-53 is commercially available by bio-techne GmbH (Wiesbaden-Nordenstadt, Germany), Cat. No. 5473.

Compounds similar to PMX-53 that are also suitable for practicing the present invention are disclosed in international patent applications WO 99/00406 A1, WO 03/033528 A1, and WO 2008/009062 A1, which are herein incorporated by reference in their entirety. Thus, in some embodiments the inhibitor of C5a activity is a cyclic peptide or peptidomimetic compound of the formula IV

IV

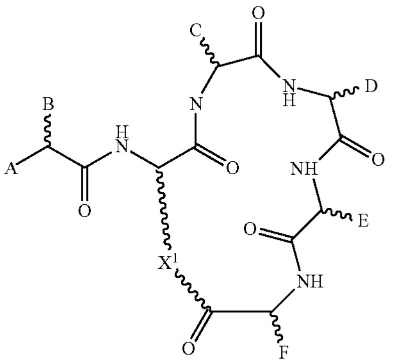

where A is H, alkyl, aryl, $NH_2$, NH-alkyl, N (alkyl) 2, NH-aryl, NH-acyl, NH-benzoyl, $NHSO_3$, $NHSO_2$-alkyl, $NHSO_2$-aryl, OH, O-alkyl, or O-aryl;

B is an alkyl, aryl, phenyl, benzyl, naphthyl or indole group, or the side chain of a D- or L-amino acid, but is not the side chain of glycine, D-phenylalanine, L-homophenylalanine, L-tryptophan, L-homotryptophan, L-tyrosine, or L-homotyrosine;

C is the side chain of a D-, L- or homo-amino acid, but is not the side chain of isoleucine, phenylalanine, or cyclohexylalanine;

D is the side chain of a neutral D-amino acid, but is not the side chain of glycine or D-alanine, a bulky planar side chain, or a bulky charged side chain;

E is a bulky substituent, but is not the side chain of D-tryptophan, L-N-methyltryptophan, L-homophenylalanine, L-2-naphthyl L-tetrahydroisoquinoline, L-cyclohexylalanine, D-leucinc, L-fluorenylalanine, or L-histidine;

F is the side chain of L-arginine, L-homoarginine, L-citrulline, or L-canavanine, or a bioisostere thereof; and $X^1$ is $-(CH_2)_nNH-$ or $(CH_2)_nS-$, where n is an integer of from 1 to 4; $-(CH_2)_2O-$; $-(CH_2)_3O$; $-(CH_2)_3-$; $-(CH_2)_4-$, $-CH_2-COCHRNH-$: or $-CH_2-CHCOCHRNH-$, where R is the side chain of any common or uncommon amino acid.

In this context, the term "common amino acid" refers to the twenty proteinogenic amino acids that are defined by the standard genetic code. The term "uncommon amino acid" includes, but is not restricted to, D-amino acids, homo-amino acids, N-alkyl amino acids, dehydroamino acids, aromatic amino acids other than phenylalanine, tyrosine and tryptophan, ortho-, meta- or para-aminobenzoic acid, ornithine, citrulline, canavanine, norleucinc, δ-glutamic acid, aminobutyric acid, L-fluorenylalanine, L-3-benzothienylalanine, and α,α-disubstituted amino acids.

Specific antagonists of C5aR (CD88) suitable for practicing the present invention include PMX95, PMX218, PMX200, PMX273, PMX205, and PMX201, as disclosed in WO 2008/009062 A1.

Clone S5/1 is a monoclonal antibody recognizing the human receptor for C5a (CD88). Clone S5/1 was raised against a synthetic peptide comprising the N-terminal domain of the C5aR (Met1-Asn31). The antibody has been shown to inhibit the binding of C5a to its receptor. It is commercially available via Hycult Biotech (Uden, The Netherlands), Cat. No. HM2094.

Clone 7H110 is a monoclonal mouse antibody recognizing the human receptor for C5a (CD88). It is commercially available via Biomol GmbH (Hamburg, Germany); Cat. No. C2439-60N.

As used herein, a "patient" means any mammal or bird who may benefit from a treatment with the compound described herein (i.e. with an inhibitor of C5a activity described herein). Preferably, a "patient" is selected from the group consisting of laboratory animals (e.g. mouse or rat), domestic animals (including e.g. guinea pig, rabbit, chicken, turkey, pig, sheep, goat, camel, cow, horse, donkey, cat, or dog), or primates including chimpanzees and human beings. It is particularly preferred that the "patient" is a human being.

As used herein, "treat", "treating" or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, "prevent", "preventing", "prevention", or "prophylaxis" of a disease or disorder means preventing that a disorder occurs in a subject.

An "effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Pharmaceutically acceptable" means approved by a regulatory agency of the Federal or a state government or listed in the U.S. Pharmacopeia or other generally recognized pharmacopeia for use in animals, and more particularly in humans.

EMBODIMENTS OF THE INVENTION

The present invention will now be further described. In the following passages different aspects of the invention are defined in more detail. Each aspect defined below may be combined with any other aspect or aspects unless clearly indicated to the contrary. In particular, any feature indicated as being preferred or advantageous may be combined with any other feature or features indicated as being preferred or advantageous.

In a first aspect the present invention relates to inhibitor of C5a activity for use in the treatment of a medical condition caused by or associated with infection with a corona virus, wherein the medical condition is preferably (i) pneumonia, and/or (ii) fever.

In a second aspect the present invention relates to an inhibitor of C5a activity for use in the reduction of an inflammatory response in a subject suffering from a corona virus infection.

In a third aspect the present invention relates to an inhibitor of C5a activity for use in the improvement of organ function, in particular lung function and/or hepatic function, in a subject suffering from a corona virus infection.

The inhibitor of C5a activity for use according to any one of claims 1 to 3, wherein the corona virus is selected from the group comprising SARS-CoV, MERS-CoV and SARS-CoV-2.

A Coronavirus is: a type of common virus that infects humans, typically leading to an upper respiratory infection (URI.) Seven different types of human coronavirus have been identified. Most people will be infected with at least one type of coronavirus in their lifetime. The viruses are spread through the air by coughing and sneezing, close personal contact, touching an object or surface contaminated with the virus and rarely, by fecal contamination. The illness caused by most coronaviruses usually lasts a short time and is characterized by runny nose, sore throat, feeling unwell, cough, and fever.

Non-limiting examples of human coronaviruses that have been reported to cause severe symptoms include the MERS-CoV (the beta coronavirus that causes Middle East Respiratory Syndrome, or MERS), SARS-CoV (the beta coronavirus that causes severe acute respiratory syndrome, or SARS, and the new 2019 Novel Coronavirus (2019-nCoV) outbreak that began in Wuhan, China.

In a preferred embodiment of the first to third aspect of the invention the subject suffers from SARS, MERS or COVID-19, in particular COVID-19.

In a preferred embodiment of the first to third aspect of the invention the treatment results in one or more of the following:

reduction of C-reactive protein;
reduction of fever;
increase of lymphocyte counts in blood;
reducing ALT/AST; and/or
increasing oxygen index ($PaO_2/FiO_2$).

C-reactive protein is usually in a range of 0-5 mg/L in healthy humans. Patients with a corona virus infection (e.g. COVID-19) have about 50 mg/L (see Chen et al. The Lancet 2020 oi.org/10.1016/S0140-6736). Thus, a reduction in C-reactive protein is attained if it is reduced to less than 40 mg/L, preferably to less than 30 mg/L, more preferably to less than 10 mg/L, more preferably to less than 5 mg/L.

Lymphocyte count in blood is usually in a range of 1.1 to $3.2\times10^9$/L in healthy humans. Patients with a mild corona virus infection (e.g. COVID-19) are in the range of 0.6 to $1.2\times10^9$/L, with a median of $0.9\times10^9$/L, whereas a more severe (e.g. COVID-19) infection results in a range of 0.5 to $0.9\times10^9$/L with a median of $0.8\times10^9$/L (see Wang et al. JAMA doi: 10.1001/jama.2020.1585). Thus, an increase in lymphocyte counts in blood is attained, if the lymphocytes count in the respective patient is increased by at least 20%, preferably at least 50%, more preferably at least 100%. In absolute terms, the C5a inhibitor for use of the present invention increases lymphocyte counts of a patient to at least $1.0\times10^9$/L, more preferably at least $1.3\times10^9$/L.

Alanine amino transferase (ALT) is usually in a range of 9-50 U/L in healthy humans. Patients with a mild corona virus infection (e.g. COVID-19) are in the range of 15-36 U/L with a median of 23 U/L whereas a more severe (e.g. COVID-19) infection results in a range of 19-57 U/L with a median of 35 U/L (see Wang et al. JAMA doi: 10.1001/jama.2020.1585). Thus, a reduction in ALT is attained, if ALT in the respective patient is reduced by at least 20%, preferably at least 50%, more preferably at least 100%.

Aspartate aminotransferase (AST) is usually in a range of 15-40 U/L in healthy humans. Patients with a mild corona virus infection (e.g. COVID-19) are in the range of 21-38 U/L with a median of 29 U/L whereas a more severe (e.g. COVID-19) infection results in a range of 30-70 U/L with a median of 52 U/L (see Wang et al. JAMA doi: 10.1001/jama.2020.1585). Thus, a reduction in AST is attained, if AST in the respective patient is reduced by at least 20%, preferably at least 50%, more preferably at least 100%.

The oxygen index $PaO_2/FiO_2$ is in healthy patient in the range of 400-500 mm Hg. Patients with a corona virus infection (e.g. COVID-19) are in a range of 103-234 mm Hg with a median of 136 mm Hg. Thus, an increase in oxygen index $PaO_2/FiO_2$ is attained, if the oxygen index $PaO_2/FiO_2$ in the respective patient is increased by at least 20%, preferably at least 50%, more preferably at least 100%. In absolute terms, the C5a inhibitor for use of the present invention increases the oxygen index $PaO_2/FiO_2$ of a patient to at least 250 mm Hg, more preferably at least 300 mm Hg.

In some embodiments of any aspect of the present invention, the inhibitor of C5a activity:

lowers the concentration of C5 (for example, by inhibiting formation and/or activity of C3 convertase; by inhibiting formation and/or activity of C5 convertase; by inhibiting the transcription of the C5 gene; by blocking translation of the C5 mRNA; by increasing degradation of the C5 mRNA; by increasing degradation of the C5 protein; or by prevention secretion of C5 from the liver);

inhibits the cleavage of C5 into C5a and C5b (for example, by inhibiting the C5 convertase or by binding to a cleavage site on C5 thereby blocking cleavage);

lowers the concentration of C5a (for example, by increasing degradation of the C5a protein);

inhibits the binding between C5a and a C5a receptor (for example by binding to C5a or by binding to a C5a receptor);

lowers the concentration of a C5a receptor (for example, by inhibiting transcription of a C5a receptor gene; by blocking translation of a C5a receptor mRNA; by increasing degradation of a C5a receptor mRNA; by increasing degradation of a C5a receptor protein); and/or inhibits the activity of a C5a receptor.

In some embodiments of any aspect of the present invention, the inhibitor of C5a activity is selected from the group consisting of a protein ligand (as defined above); an oligonucleotide; and a small molecule (as defined above). Oligonucleotides acting as inhibitors of C5a activity can achieve their inhibitory effect for example by binding to nucleic acid molecules (thereby inhibiting transcription and/or translation) or by binding to proteins (e.g. when the oligonucleotides are nucleic acid aptamers).

In some embodiments of any aspect of the present invention, the inhibitor of C5a activity is a protein ligand that specifically binds to C5 protein, or to C5a protein, or to a C5a receptor protein. In further embodiments, the protein ligand is selected from the group consisting of (i) antibodies (e.g. anti-C5 antibodies, anti-C5a antibodies, anti-C5aR antibodies, or anti-C5L2 antibodies),
(ii) antigen-binding fragments of antibodies,
(iii) antibody-like proteins,
(iv) inhibitory variants of C5a,
(v) inhibitory variants of a C5a receptor (e.g. decoy receptors),
(vi) proteins acting on the complement pathway (e.g. COVERSIN™); and
(vii) peptides (e.g. RA101495 (Ra Pharma, Cambridge, MA); PMX-53 (bio-techne GmbH (Wiesbaden-Nordenstadt, Germany)).

In some embodiments of any aspect of the present invention, the inhibitor of C5a activity is a protein ligand or an oligonucleotide, preferably a protein ligand, that specifically binds to a conformational epitope formed by amino acid sequences NDETCEQRA (SEQ ID NO: 2) and SHKDMQL (SEQ ID NO: 3) of human C5a. Binding to the conformational formed by the amino acid sequences according to SEQ ID NOs: 2 and 3 means that the protein ligand or oligonucleotide binds to at least one amino acid within the amino acid sequence according to SEQ ID NO: 2 and to at least one amino acid within the amino acid sequence according to SEQ ID NO: 3. SEQ ID NO: 2 corresponds to amino acids 30-38 of human C5a. SEQ ID NO: 3 corresponds to amino acids 66-72 of human C5a.

In some embodiments of any aspect of the present invention the protein ligand or oligonucleotide, preferably the protein ligand, binds to at least one amino acid within the amino acid sequence according to DETCEQR (SEQ ID NO: 4). SEQ ID NO: 4 corresponds to amino acids 31-37 of human C5a.

In some embodiments of any aspect of the present invention the protein ligand or oligonucleotide, preferably the protein ligand, binds to at least one amino acid within the amino acid sequence according to HKDMQ (SEQ ID NO: 5), more preferably to at least one amino acid within the amino acid sequence KDM. SEQ ID NO: 5 corresponds to amino acids 67-71 of human C5a; the sequence KDM corresponds to amino acids 68-70 of human C5a.

In some embodiments of any aspect of the present invention the protein ligand or oligonucleotide, preferably the protein ligand, binds to at least one amino acid within the amino acid sequence DETCEQR (SEQ ID NO: 4) and to at least one amino acid within the amino acid sequence HKDMQ (SEQ ID NO: 5).

In some embodiments of any aspect of the present invention the protein ligand or oligonucleotide, preferably the protein ligand, binds to at least one amino acid within the amino acid sequence DETCEQR (SEQ ID NO: 4) and to at least one amino acid within the amino acid sequence KDM.

In some embodiments of any aspect of the present invention the two sequences forming the conformational epitope of C5a (e.g. sequence pairs according to SEQ ID NO: 2 and 3; SEQ ID NO: 4 and 5; or SEQ ID NO: 4 and sequence KDM) are separated by 1-50 contiguous amino acids that do not participate in binding to the binding moiety of the invention. In the following, such amino acids that do not participate in binding to the binding moiety of the invention will be referred to as "non-binding amino acids". The two sequences forming the conformational epitope are preferably separated by 6-45 contiguous non-binding amino acids, more preferably by 12-40 contiguous non-binding amino acids, more preferably by 18-35 contiguous non-binding amino acids, more preferably by 24-30 contiguous non-binding amino acids, more preferably by 25-29 contiguous non-binding amino acids, even more preferably by 26-28 contiguous non-binding amino acids, and most preferably by 27 contiguous non-binding amino acids.

In some embodiments of any aspect of the present invention the protein ligand or oligonucleotide, preferably the protein ligand, specifically binding to a conformational epitope of C5a has a binding constant to human C5a with a $K_d$ value of 10 nM or less, preferably 9 nM or less, more preferably 8 nM or less, more preferably 7 nM or less, more preferably 6 nM or less, more preferably 5 nM or less, more preferably 4 nM or less, more preferably 3 nM or less, more preferably 2 nM or less, and even more preferably 1 nM or less. In some embodiments of any aspect of the present invention the dissociation constant $K_d$ between the binding moiety and human C5a is between 1 μM (picomolar) and 5 nM (nanomolar), more preferably between 2 μM and 4 nM, more preferably between 5 μM and 3 nM, more preferably between 10 μM and 2 nM, more preferably between 50 μM and 1 nM, more preferably between 100 μM and 900 μM, more preferably between 200 μM and 800 μM, more preferably between 300 μM and 700 μM, and even more preferably between 400 μM and 600 μM.

In some embodiments of any aspect of the present invention the protein ligand or oligonucleotide, preferably the protein ligand, specifically binding to C5a exhibits at least 75% blocking activity, preferably at least 80% blocking activity, more preferably at least 85% blocking activity, more preferably at least 90% blocking activity, more preferably at least 95% blocking activity for biological effects induced by one molecule C5a, particularly human C5a. These particular blocking activities refer to those embodiments, wherein the binding moiety comprises a single paratope binding to C5a, preferably human C5a. In embodiments, wherein the binding moiety comprises two or more C5a-specific paratopes, said blocking activities of at least 75%, preferably at least 80%, more preferably at least 85%, etc. are achieved when one binding-moiety molecule is contacted with a number of C5a molecules equal to the number of C5a-specific paratopes present in the binding moiety. In other words, when the paratopes of a binding moiety described herein and C5a are present in equimolar concentrations, the binding moiety exhibits at least 75% blocking activity, preferably at least 80% blocking activity, more preferably at least 85% blocking activity, more preferably at least 90% blocking activity, and more preferably at least 95% blocking activity for biological effects induced by C5a. A preferred biological effect to be blocked is C5a-induced lysozyme release from human whole blood cells. Assays for determining this C5a-induced lysozyme release and its blocking are described, for example, in WO 2011/063980 A1 and in the corresponding US national stage application US 2012/0231008 A1.

In some embodiments of any aspect of the present invention the protein ligand is an antibody or an antigen-binding fragment thereof, wherein said antibody or antigen-binding fragment thereof comprises (i) a heavy chain CDR3 sequence as set forth in SEQ ID NO: 6; or
(ii) a heavy chain CDR3 sequence as set forth in SEQ ID NO: 7;

wherein the heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In some embodiments of any aspect of the present invention the protein ligand is an antibody or an antigen-binding fragment thereof, wherein said antibody or antigen-binding fragment thereof comprises (iii) a light chain CDR3 sequence as set forth in SEQ ID NO: 8; or (iv) a light chain CDR3 sequence as set forth in SEQ ID NO: 9;

wherein the light chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In some embodiments of any aspect of the present invention the protein ligand is an antibody or an antigen-binding fragment thereof, wherein said antibody or antigen-binding fragment thereof comprises (i) a heavy chain CDR3 sequence as set forth in SEQ ID NO: 6 and a light chain CDR3 sequence as set forth in SEQ ID NO: 8; or (ii) a heavy chain CDR3 sequence as set forth in SEQ ID NO: 7 and a light chain CDR3 sequence as set forth in SEQ ID NO: 9;

wherein the heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions; and wherein the light chain CDR3 sequence optionally comprises 1, 2, or 3 amino acid exchanges, preferably conservative amino acid exchanges, 1, 2, or 3 amino acid deletions, and/or 1, 2, or 3 amino acid additions.

In some embodiments of any aspect of the present invention the protein ligand is an antibody or an antigen-binding fragment thereof, wherein said antibody or antigen-binding fragment thereof comprises at least one of the following sequences:

(v) a heavy chain CDR2 sequence according to SEQ ID NO: 10;

(vi) a heavy chain CDR2 sequence according to SEQ ID NO: 11;

(vii) a light chain CDR2 sequence according to SEQ ID NO: 12;

(viii) a light chain CDR2 sequence according to SEQ ID NO: 13;

(ix) a heavy chain CDR1 sequence according to SEQ ID NO: 14;

(x) a heavy chain CDR1 sequence according to SEQ ID NO: 15;

(xi) a light chain CDR1 sequence according to SEQ ID NO: 16; or (xii) a light chain CDR1 sequence according to SEQ ID NO: 17;

wherein the heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions;

wherein the light chain CDR2 sequence optionally comprises 1, 2, or 3 amino acid exchanges, preferably conservative amino acid exchanges, 1, 2, or 3 amino acid deletions, and/or 1, 2, or 3 amino acid additions;

wherein the heavy chain CDR1 sequence optionally comprises 1, 2 or 3 amino acid exchanges, preferably conservative amino acid exchanges, 1, 2, or 3 amino acid deletions, and/or 1, 2, or 3 amino acid additions; and wherein the light chain CDR1 sequence optionally comprises 1, 2, or 3 amino acid exchanges, preferably conservative amino acid exchanges, 1, 2, or 3 amino acid deletions, and/or 1, 2, or 3 amino acid additions.

In particular embodiments, the total number of these optional changes recited above in each one of the amino acid sequences according to SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 14, SEQ ID NO: 15, SEQ ID NO: 16, and SEQ ID NO: 17, i.e. the total number of exchanges, deletions and additions in each sequence, is 1 or 2.

In particular embodiments the total number of exchanges, deletions, and additions added up for all CDRs present in an antibody or antigen-binding fragment thereof is between 1 and 5 (e.g. 1, 2, 3, 4, or 5).

In some embodiments of any aspect of the present invention the protein ligand is an antibody or an antigen-binding fragment thereof, comprises one of the sets A to H of heavy chain CDR3, heavy chain CDR2, and heavy chain CDR1 sequences as listed below in Table 1, wherein each heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions;

wherein each heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions; and wherein each heavy chain CDR1 sequence optionally comprises 1, 2, or 3 amino acid exchanges, preferably conservative amino acid exchanges, 1, 2, or 3 amino acid deletions, and/or 1, 2, or 3 amino acid additions:

TABLE 1

Sets of heavy chain CDR sequences suitable for use in the antibodies or fragments thereof of the present invention

| Symbol of heavy chain set | CDR3 sequence | CDR2 sequence | CDR1 sequence |
|---|---|---|---|
| A | SEQ ID NO: 6 | SEQ ID NO: 10 | SEQ ID NO: 14 |
| B | SEQ ID NO: 6 | SEQ ID NO: 10 | SEQ ID NO: 15 |
| C | SEQ ID NO: 6 | SEQ ID NO: 11 | SEQ ID NO: 14 |
| D | SEQ ID NO: 6 | SEQ ID NO: 11 | SEQ ID NO: 15 |
| E | SEQ ID NO: 7 | SEQ ID NO: 10 | SEQ ID NO: 14 |
| F | SEQ ID NO: 7 | SEQ ID NO: 10 | SEQ ID NO: 15 |
| G | SEQ ID NO: 7 | SEQ ID NO: 11 | SEQ ID NO: 14 |
| H | SEQ ID NO: 7 | SEQ ID NO: 11 | SEQ ID NO: 15 |

In some embodiments of any aspect of the present invention the protein ligand is an antibody or an antigen-binding fragment thereof, comprises one of the following sets I to IV of light chain CDR3, light chain CDR2, and light chain CDR1 sequences as listed in Table 2, wherein each light chain CDR3 sequence optionally comprises 1, 2, or 3 amino acid exchanges, preferably conservative amino acid exchanges, 1, 2, or 3 amino acid deletions, and/or 1, 2, or 3 amino acid additions;

wherein each light chain CDR2 sequence optionally comprises 1, 2, or 3 amino acid exchanges, preferably conservative amino acid exchanges, 1, 2, or 3 amino acid deletions, and/or 1, 2, or 3 amino acid additions; and wherein each light chain CDR1 sequence optionally comprises 1, 2, or 3 amino acid exchanges, preferably conservative amino acid exchanges, 1, 2, or 3 amino acid deletions, and/or 1, 2, or 3 amino acid additions.

TABLE 2

Sets of light chain CDR sequences suitable for use in the antibodies or fragments thereof of the present invention Since the CDR2 light chain sequence of antibody IFX-1 (SEQ ID NO: 12) is identical to the CDR2 light chain sequence of antibody INab708 (SEQ ID NO: 13), sets including SEQ ID NO: 13 would be redundant to sets including SEQ ID NO: 12. Therefore, the table only lists four sets of light chain CDR sequences.

| Number of light chain set | CDR3 sequence | CDR2 sequence | CDR1 sequence |
|---|---|---|---|
| I | SEQ ID NO: 8 | SEQ ID NO: 12 | SEQ ID NO: 16 |
| II | SEQ ID NO: 8 | SEQ ID NO: 12 | SEQ ID NO: 17 |
| III | SEQ ID NO: 9 | SEQ ID NO: 12 | SEQ ID NO: 16 |
| IV | SEQ ID NO: 9 | SEQ ID NO: 12 | SEQ ID NO: 17 |

In some embodiments of any aspect of the present invention the protein ligand is an antibody or an antigen-binding fragment thereof, comprises one of the heavy CDR sets A-H listed above in Table 1 and one of the light chain CDR sets I-IV listed above in Table 2, i.e. one of the following combinations of sets: A-I, A-II, A-III, A-IV, B-I, B-II, B-III, B-IV, C-I, C-II, C-III, C-IV, D-I, D-II, D-III, D-IV, E-I, E-II, E-III, E-IV, F-I, F-II, F-III, F-IV, G-I, G-II, G-III, G-IV, H-I, H-II, H-III, or H-IV (wherein the combinations A-I and H-IV are especially preferred), wherein each heavy chain CDR3 sequence optionally comprises 1, 2, or 3 amino acid exchanges, preferably conservative amino acid exchanges, 1, 2, or 3 amino acid deletions, and/or 1, 2, or 3 amino acid additions;

wherein each heavy chain CDR2 sequence optionally comprises 1, 2, or 3 amino acid exchanges, preferably conservative amino acid exchanges, 1, 2, or 3 amino acid deletions, and/or 1, 2, or 3 amino acid additions;

wherein each heavy chain CDR1 sequence optionally comprises 1, 2, or 3 amino acid exchanges, preferably conservative amino acid exchanges, 1, 2, or 3 amino acid deletions and/or 1, 2, or 3 amino acid additions;

wherein each light chain CDR3 sequence optionally comprises 1, 2, or 3 amino acid exchanges, in particular conservative amino acid exchanges, 1, 2, or 3 amino acid deletions, and/or 1, 2, or 3 amino acid additions;

wherein each light chain CDR2 sequence optionally comprises 1, 2, or 3 amino acid exchanges, preferably conservative amino acid exchanges, 1, 2, or 3 amino acid deletions, and/or 1, 2, or 3 amino acid additions; and wherein each light chain CDR1 sequence optionally comprises 1, 2, or 3 amino acid exchanges, preferably conservative amino acid exchanges, 1, 2, or 3 amino acid deletions and/or 1, 2, or 3 amino acid additions.

In some embodiments of any aspect of the present invention the protein ligand is an antibody or an antigen-binding fragment thereof, comprises a VH domain that comprises, essentially consists of or consists of (i) the VH domain of IFX-1 or (ii) the VH domain of INab708.

The FR1, CDR1, FR2, CDR2, FR3, CDR3, and FR4 sequences defining the VH domains of IFX-1 and INab708 are shown below in Table 3.

In some embodiments of any aspect of the present invention the protein ligand is an antibody or an antigen-binding fragment thereof, comprises a VL domain that comprises, essentially consists of or consists of (i) the VL domain of IFX-1 or (ii) the VL domain of INab708.

The FR1, CDR1, FR2, CDR2, FR3, CDR3, and FR4 sequences defining the VL domains of IFX-1 and INab708 are shown below in Table 3.

TABLE 3

CDR and FR sequences of antibodies IFX-1 and INab708 (Chothia classification mode)

| IFX-1: | INab708: |
|---|---|
| Heavy Chain: | Heavy Chain: |
| FR1: QVQLQQSGPQLVRPGTSVKIS (= SEQ ID NO: 18) | FR1: VQLLESGAELMKPGASVKIS (SEQ ID NO: 26) |
| CDR1: CKASGYSFTTFWMD (= SEQ ID NO: 14) | CDR1: CKATGNTFSGYWIE (= SEQ ID NO: 15) |
| FR2: WVKQRPGQGLEWIGR (SEQ ID NO: 19) | FR2: WVKQRPGHGLEWIGE (SEQ ID NO: 27) |
| CDR2: IDPSDSESRLDQ (= SEQ ID NO: 10) | CDR2: ILPGSGSTNYNE (= SEQ ID NO: 11) |
| FR3: RFKDRATLTVDKSSSTV YMQLSSPTSEDSAVYY (SEQ ID NO: 20) | FR3: KFKGKATLTADTSSNTA YMQLSSLTSEDSAVYY (SEQ ID NO: 28) |
| CDR3: CARGNDGYYGFAY (= SEQ ID NO: 6) | CDR3: CTRRGLYDGSSYFAY (= SEQ ID NO: 7) |
| FR4: WGQGTLVTVSS (SEQ ID NO: 21) | FR4: WGQGTLVTVSA (SEQ ID NO: 29) |
| Light Chain: | Light Chain: |
| FR1: DIVLTQSPASLAVSLGQRATIS (SEQ ID NO: 22) | FR1: DIVLTQSPASLAVSLGQRATIS (SEQ ID NO: 30) |
| CDR1: CKASQSVDYDGDSYMK (= SEQ ID NO: 16) | CDR1: CKASQSVDYDGDSYMN (= SEQ ID NO: 17) |
| FR2: WYQQKPGQPPKLL (SEQ ID NO: 23) | FR2: WYQQKPGQPPKLL (SEQ ID NO: 31) |
| CDR2: IYAASNL (= SEQ ID NO: 12) | CDR2: IYAASNL (= SEQ ID NO: 13) |
| FR3: QSGIPARFSGSGSGT ADFTLNIHPVEEEDATYY (SEQ ID NO: 24) | FR3: GSGIPARFSGSGSGTDFT LNIHPVEEEVAATYY (SEQ ID NO: 32) |
| CDR3: CQQSNEDPYT (= SEQ ID NO: 8) | CDR3: CQQNNEDPLT (= SEQ ID NO: 9) |
| FR4: FGGGTKLEIK (SEQ ID NO: 25) | FR4: FGAGTLLELK (SEQ ID NO: 33) |

In some embodiments the antibody for use in the present invention or the antigen-binding fragment thereof, comprises:

(i) a variable heavy chain with the amino acid sequence according to SEQ ID NO: 34 and a variable light chain sequence with the amino acid sequence according to SEQ ID NO: 35 or variants with at least 90%, at least 93% or at least 95% amino acid sequence identity with SEQ ID NO: 34 and 35 which comprise the amino acid sequences according SEQ ID NO: 6, 8, 10, 12, 14 and 16 of the light and heavy chain CDR1 to CDR3 or variants thereof as specified above;

(ii) a variable heavy chain sequence with the amino acid sequence of SEQ ID NO: 36 and the variable light chain sequence with the amino acid sequence according to SEQ ID NO: 37 or variants with at least 90% amino acid sequence identity with SEQ ID NO: 36 and 37 which comprise the amino acid sequences according SEQ ID NO: 7, 9, 11, 13, 15 and 17 of the light and heavy chain CDR1 to CDR3 or variants thereof as specified above.

In the above aspect the CDRs have no or minimal variations, i.e. 1, 2, or 3 amino acids as outlined above and the majority of the amino acid modifications are in the framework regions.

In some embodiments of any aspect of the present invention, the inhibitor of C5a activity is an oligonucleotide that specifically binds to C5, or to C5a, or to a C5a receptor. In further embodiments, the oligonucleotide is a nucleic acid aptamer. The nucleic acid aptamer may be selected from the group consisting of DNA-aptamers, D-RNA aptamers, and L-RNA aptamers (e.g., SPIEGELMERS™).

In some embodiments of any aspect of the present invention, the inhibitor of C5a activity reduces expression of C5 protein or a C5a receptor protein. In further embodiments, said inhibitor of C5a activity that reduces expression of C5 protein or a C5a receptor protein is an oligonucleotide selected from the group consisting of antisense DNA, antisense RNA, siRNA, and miRNA.

In some embodiments of any aspect of the present invention, the C5a receptor is C5aR and/or C5L2. In preferred embodiments of any aspect of the present invention, the C5a receptor is C5aR (also known as CD88 or C5aR1).

In some embodiments of any aspect of the present invention, the inhibitor of C5a activity is selected from the group consisting of:

(a) IFX-1, INab708, MEDI-7814, ALXN-1007, or NOX-D21, or an antigen-binding fragment thereof;
(b) an antibody or an antigen-binding fragment thereof, wherein said antibody or antigen-binding fragment thereof competes with one of the antibodies indicated under (a) for binding to C5a;
(c) Eculizumab, ALXN1210, ALXN5500, or LFG316, or an antigen-binding fragment thereof;
(d) an antibody or an antigen-binding fragment thereof, wherein said antibody or antigen-binding fragment thereof competes with one of the antibodies indicated under (c) for binding to C5;
(e) COVERSIN™ or RA101495;
(f) an antibody or an antigen-binding fragment thereof or protein or macrocyclic peptide wherein said antibody or antigen-binding fragment thereof or macrocyclic peptide competes with one of the or protein or peptides indicated under (e) for binding to C5;
(g) ZIMURA®;
(h) an antibody or an antigen-binding fragment thereof or an aptamer, wherein said antibody or antigen-binding fragment thereof or aptamer competes with ZIMURAR for binding to C5;
(i) AMY-201 or Mirococept;
(j) an antibody or an antigen-binding fragment thereof or a protein wherein said antibody or antigen-binding fragment thereof or protein competes with one of the proteins indicated under (i) for binding to C3b;
(k) Bikaciomab;
(l) an antibody or an antigen-binding fragment thereof, wherein said antibody or antigen-binding fragment thereof competes with Bikaciomab for binding to Factor B;
(m) Lampalizumab;
(n) an antibody or an antigen-binding fragment thereof, wherein said antibody or antigen-binding fragment thereof competes with Lampalizumab for binding to Factor D;
(o) ALN-CC5;
(p) Avacopan or a compound according to formula II or III or PMX-53 or a compound according to formula IV;
(q) an antibody or an antigen-binding fragment thereof, wherein said antibody or antigen-binding fragment thereof competes with avacopan or PMX-53 for binding to C5aR;
(r) clone S5/1 or clone 7H110, or an antigen-binding fragment thereof; and
(s) an antibody or an antigen-binding fragment thereof, wherein said antibody or antigen-binding fragment thereof competes with one of the antibodies indicated under (r) for binding to C5aR.

Pharmaceutical Compositions and Modes of Administration

In the practice of any aspect of the present invention, a compound (e.g. an inhibitor of C5a activity described herein) or a pharmaceutical composition comprising the compound may be administered to a patient by any route established in the art which provides a sufficient level of the compound in the patient. It can be administered systemically or locally. Such administration may be parenterally, transmucosally, e.g., orally, nasally, rectally, intravaginally, sublingually, submucosally, transdermally, or by inhalation. Preferably, administration is parenteral, e.g., via intravenous or intraperitoneal injection, and also including, but is not limited to, intra-arterial, intramuscular, intradermal and subcutaneous administration. If the compound described herein (e.g. an inhibitor of C5a activity described herein) or a pharmaceutical composition comprising the compound is administered locally, it can be injected directly into the organ or tissue to be treated.

Pharmaceutical compositions adapted for oral administration may be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient for a prolonged period of time. Pharmaceutical compositions adapted for topical administration may be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. Pharmaceutical compositions may also be administered via the nasal cavity to the lungs.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use. Extemporaneous injection solutions and suspensions may be prepared from sterile powders, granules and tablets.

In a preferred embodiment, a compound described herein (e.g. an inhibitor of C5a activity described herein) is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients may be mixed prior to administration.

In another embodiment, for example, a compound (e.g. an inhibitor of C5a activity described herein) or a pharmaceutical composition comprising the compound can be delivered in a controlled-release system. For example, the compound may be administered using intravenous infusion, an implantable osmotic pump, a transdermal patch, liposomes, or other modes of administration. In one embodiment, a pump may be used (see Sefton (1987) *CRC Crit. Ref. Biomed. Eng.* 14:201; Buchwald et al. (1980) *Surgery* 88:507; Saudek et al. (1989) *N. Eng. J. Med.* 321:574). In another embodiment, the compound can be delivered in a vesicle, in particular a liposome (see Langer (1990) *Science* 249:1527-1533; Treat et al. (1989) in Liposomes in the Therapy of Infectious Disease and Cancer, Lopez-Berestein and Fidler (eds.), Liss, N.Y., 353-365; WO 91/04014; U.S. Pat. No. 4,704,355). In another embodiment, polymeric materials can be used (see Medical Applications of Controlled Release (1974) Langer and Wise (eds.), CRC Press: Boca Raton, Fla.; Controlled Drug Bioavailability, Drug Product Design and Performance, (1984) Smolen and Ball (eds.), Wiley: N.Y.; Ranger and Peppas (1953) J. Macromol. Sci. Rev. Macromol. Chem. 23:61; see also Levy et al. (1985) *Science* 228:190; During et al. (1989) *Ann. Neurol.* 25:351; Howard et al. (1989) *J. Neurosurg.* 71:105).

In yet another embodiment, a controlled release system can be placed in proximity of the therapeutic target, i.e., the target cells, tissue or organ, thus requiring only a fraction of the systemic dose (see, e.g., Goodson (1984) 115-138 in Medical Applications of Controlled Release, vol. 2). Other controlled release systems are discussed in the review by Langer (1990*, Science* 249:1527-1533).

In a specific embodiment, it may be desirable to administer a compound described herein (e.g. an inhibitor of C5a activity described herein) or a pharmaceutical composition comprising the compound locally to the area in need of treatment. This may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers.

Selection of the preferred effective dose will be determined by a skilled artisan based upon considering several factors which will be known to one of ordinary skill in the art. Such factors include the particular form of the pharmaceutical composition, e.g. polypeptide or vector, and its pharmacokinetic parameters such as bioavailability, metabolism, half-life, etc., which will have been established during the usual development procedures typically employed in obtaining regulatory approval for a pharmaceutical compound. Further factors in considering the dose include the condition or disease to be prevented and or treated or the benefit to be achieved in a normal individual, the body mass of the patient, the route of administration, whether administration is acute or chronic, concomitant medications, and other factors well known to affect the efficacy of administered pharmaceutical agents. Thus the precise dosage should be decided according to the judgment of the practitioner and each patient's circumstances, e.g., depending upon the condition and the immune status of the individual patient, according to standard clinical techniques.

Preferred dosage for the inhibitor of C5a activity of the present invention, in particular for IFX-1, is a dosage of 200 mg to 500 mg per day, preferably 250 mg to 350 mg per day, more preferably 300 mg per day. The dosages are preferably applied once daily, more preferably with a dosage regimen that administers the inhibitor of C5a activity, in particular IFX-1, at day 1, day 2, day 3, day 5, day 7, day 9, day 11 and day 13.

Preferably the inhibitor of C5a activity, in particular IFX-1, is administered by parenteral application, more preferably intravenous administration.

(A) Lysates from 293T cells transfected with GFP-N and GFP-vector were subjected to immunoprecipitation with Flag-tagged full-length (FL) MASP-2 or truncated mutants (CUB1-EGF-CUB2 and CCP1-CCP2-SP) conjugated to agarose beads in the presence of 2 mM $CaCl_2$) or 1 mM EDTA. Immunoblotting was performed with the anti-GFP and anti-Flag antibodies. IgG beads and Flag beads incubated were used as a negative control. (B) Lysates from 293T cells transfected with Flag-N or Flag-vector were mixed with human serum (HS) and mouse serum (MS) and subjected to immunoprecipitation with anti-Flag agarose beads. The adsorbates were probed with anti-Flag and anti-MASP-2 antibodies. Purified recombinant MASP-2 was loaded as a marker. (C) Lysates from 293T cells transfected with full-length GFP-N and its mutants Δ321-323 and Δ116-124 were subjected to immunoprecipitation with MASP-2-Flag-conjugated agarose beads in the presence of 2 mM CaCl2 and analyzed by immunoblotting with anti-GFP and anti-Flag antibodies. (D) Lysates from 293T cells expressing GFP-MERS-CoV N and its truncated mutant Δ104-112 were subjected to immunoprecipitation with MASP-2-Flag conjugated agarose beads in the presence of 2 mM $CaCl_2$), and analyzed as mentioned above. (E) Lysates from 293T cells expressing HA-tagged N of SARS-CoV-2 were subjected to immunoprecipitation with MASP-2-Flag-conjugated agarose beads in the presence of 2 mM $CaCl_2$), the adsorbates were probed with anti-HA and anti-Flag antibodies.

Figure 2:
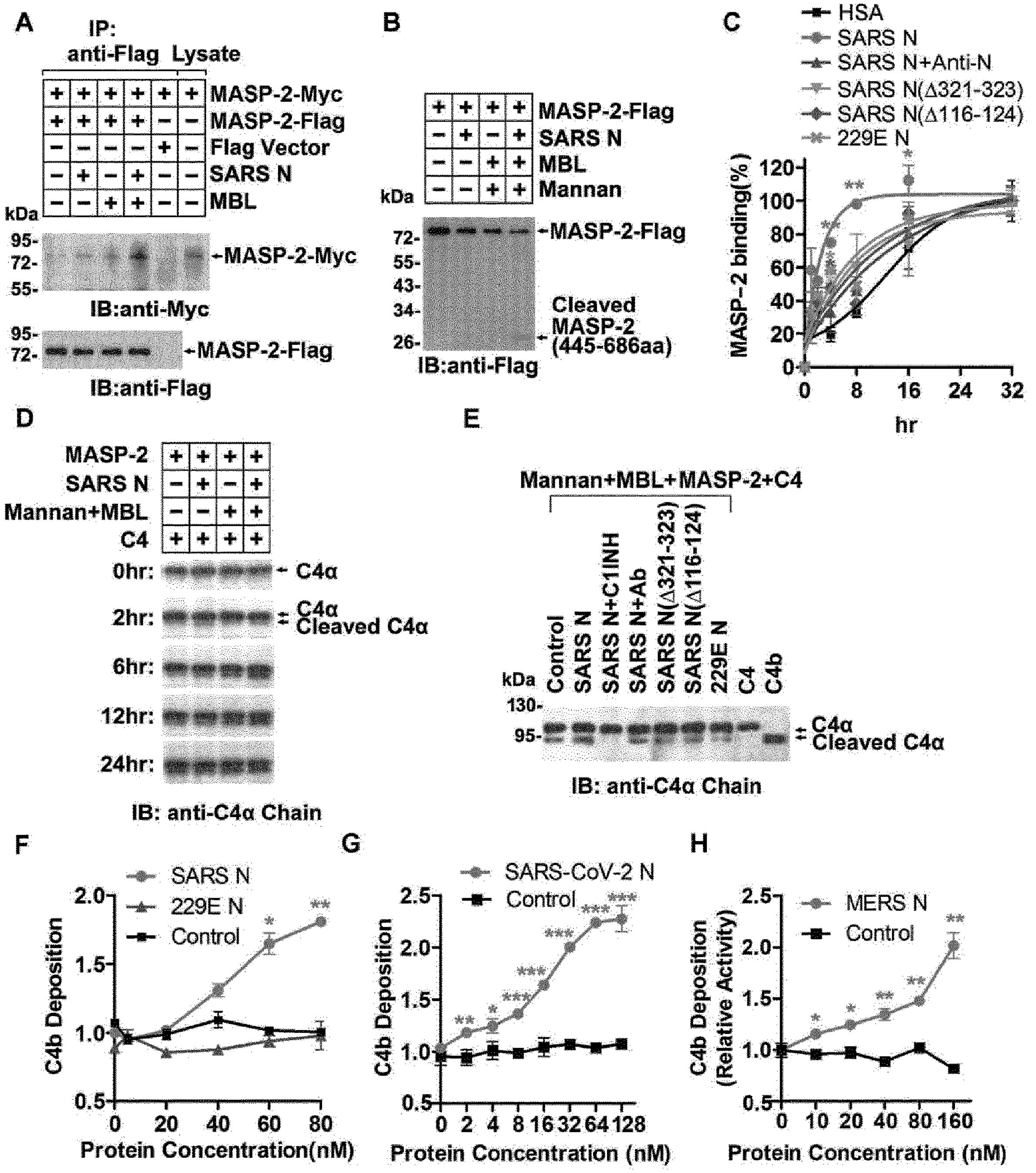

FIG. 2. The nucleocapsid proteins induce MASP-2 autoactivation and C4 cleavage.

(A) Lysates from cells expressing MASP-2-Myc were mixed with purified N or MBL and subjected to immunoprecipitation with MASP-2-Flag-conjugated agarose beads in the presence of 2 mM $CaCl_2$). Immunoblotting was performed with an anti-Myc antibody. (B) Purified MASP-2-Flag was incubated with/without N, MBL, and mannan at 37° C. for 12 hr. Cleaved MASP-2 was probed with anti-Flag antibody. (C) Purified MASP-2 and N proteins with/without anti-N monoclonal antibody were incubated with pre-conjugated MBL in mannan-coated plates at 4° C. Binding of MASP-2 was detected with an anti-MASP-2 antibody. *$P<0.05$ and **$P<0.01$ vs. HSA by unpaired two-tailed Student's t-test. (D) C4 was incubated with MASP-2, MBL, mannan, N protein, and HSA at 37° C. for 1 hr, 6 hr, 12 hr, and 24 hr. C4 and a cleaved truncated C4 fragment were detected with anti-C4α chain antibody. (E) C4 was incubated with MASP-2, MBL, mannan, N proteins, C1INH, or MASP-2 monoclonal antibody at 37° C. for 1 hr. C4 and the cleaved C4 were detected with C4α-chain antibody. (F-H) C4b deposition in relation to the concentration of N proteins of SARS-CoV, HCoV-229E, SARS-CoV-2, and MERS-CoV.

Figure 3:
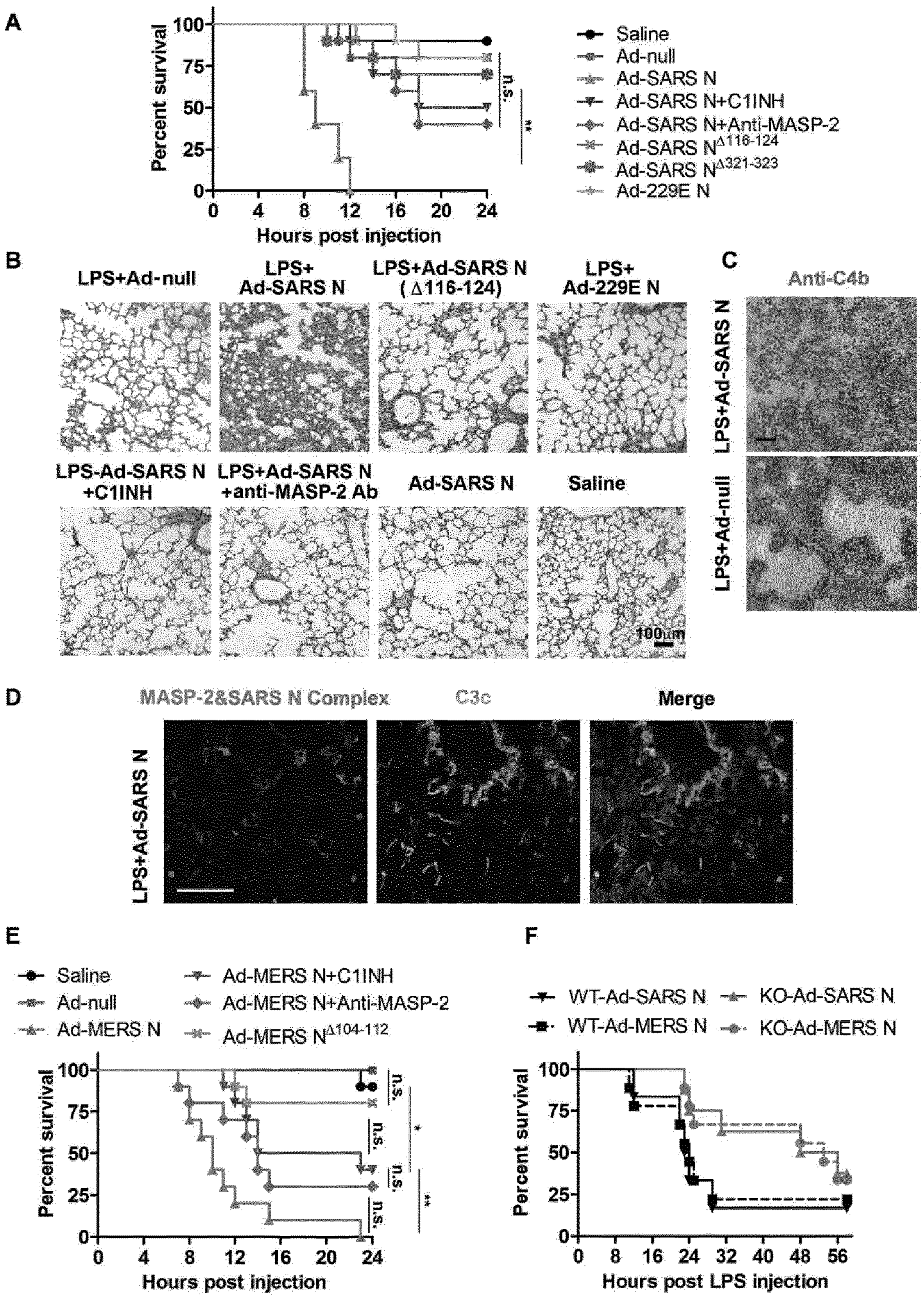

FIG. 3. N proteins potentiate LPS-induced pneumonia in vivo (A) BALB/c mice (10/group) were infected with $1\times10^9$ PFU Ad-SARS N/Ad-null or a saline control via the tail vein, and LPS (5 mg/kg) was given via the tail vein on the 6th day. Anti-MASP-2 antibody (200 μg/kg) or C1INH (4 mg/kg) was injected via the tail vein 30 min before LPS injection. The mortality of mice was noted, *$P<0.05$ and **$P<0.01$ by Gehan-Breslow-Wilcoxon test. Lung paraffin sections were analyzed by HE staining (B). Mice were infected with $1\times10^8$ PFU Ad-SARS N/Ad-null via the tail vein, and LPS (5 mg/kg) was given by nasal drip and via the tail vein on the 6th day. Mice were sacrificed 6 hr after LPS challenge. Frozen lung sections were stained with anti-C4b antibody (C). SARS-CoV N and MASP-2 complex formation in frozen lung sections was measured by in situ PLA, as indicated by the red signals. Deposited C3 fragments were stained with FITC-labeled anti-C3c antibodies (green), scale bar=50 μm (D). (E) Mice were pre-infected with $1\times10^9$ PFU Ad-MERS N/Ad-null and treated with LPS, antibody or CHINH as mentioned above, the survived mice were observed. (F) $Masp2^{-/-}$ and $Masp2^{+/+}$ C57BL/6N mice were infected N-expressing adenovirus and injected with LPS as mentioned above, the survived mice were observed.

Figure 4:
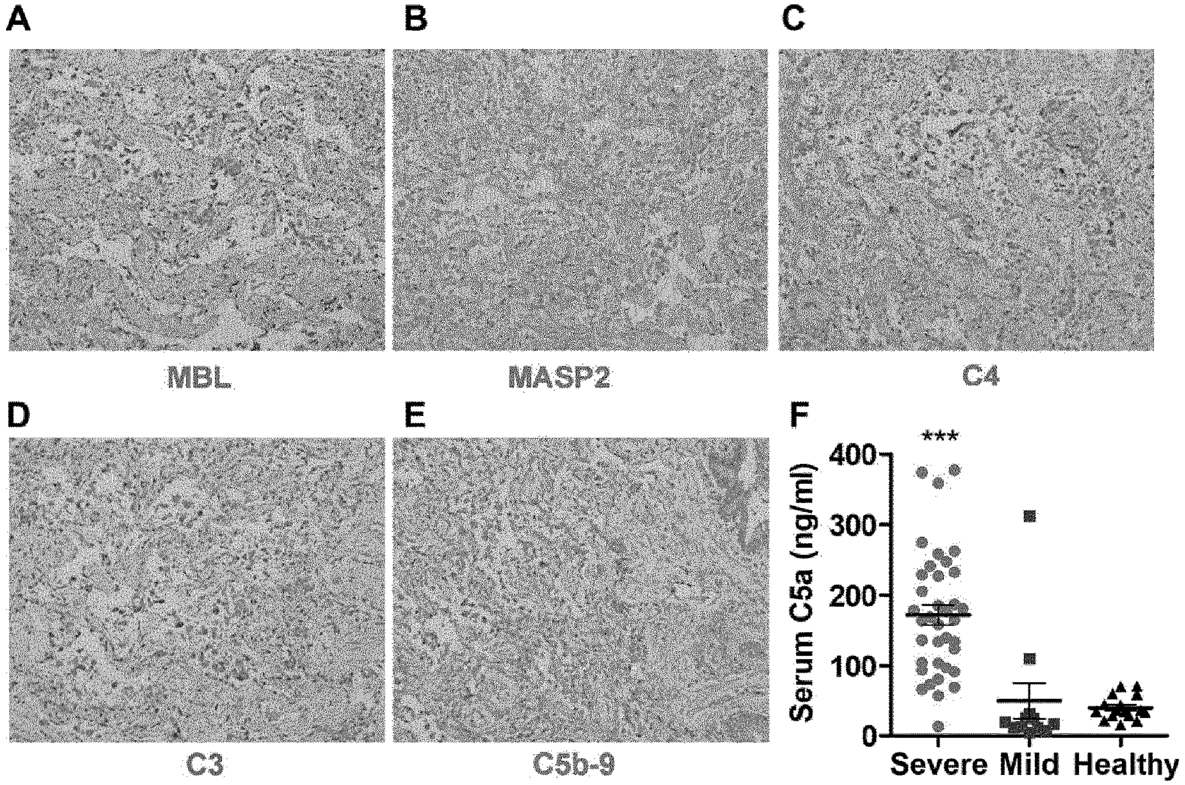

FIG. 4. Complements activation in COVID-19 patients (A-E) Paraformaldehyde-fixed lung tissues from postmortem autopsy was used for paraffin tissue sections and immunohistochemical staining with anti-MBL, anti-MASP-2, anti-C4α chain, anti C3 or C5b-9. Microphotography was carried out by Olympus BX52 microscope under a 10× objective. (F) Serum C5a from healthy people, mild or severe COVID-19 patients were analyzed by ELISA.

Figure 5:
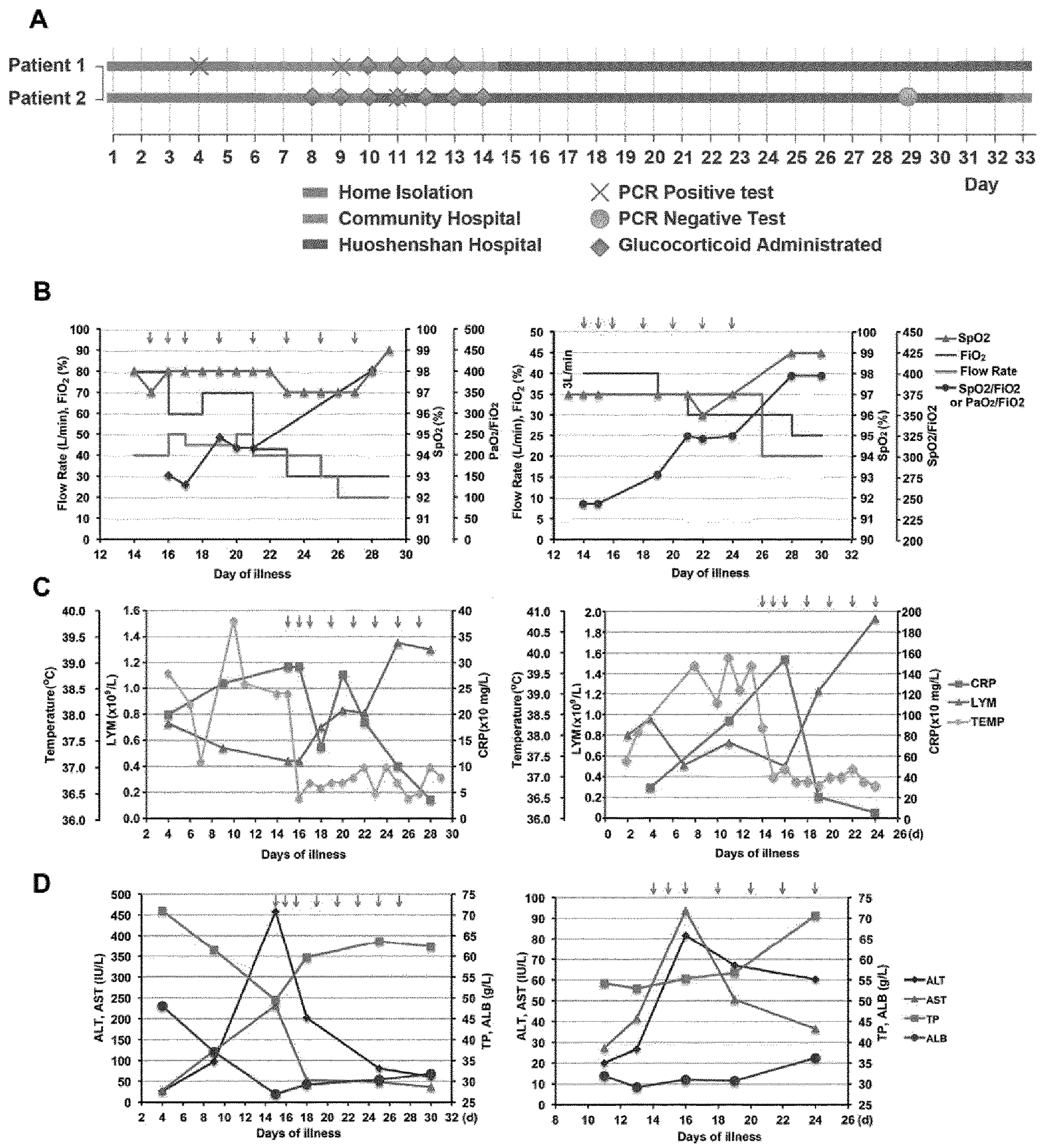

FIG. 5. Treatment of COVID-19 patients with anti-C5a antibody (A) Timeline of illness onset, SARS-CoV-2 RNA detection and hospitalization of the two patients. (B) Flow rate, fraction of inspiration ($FiO_2$) of high-flow nasal oxygen, percutaneous oxygen saturation ($SpO_2$) and oxygenation index ($PaO_2/FiO_2$) or $SpO_2/FiO_2$ in patient #1 (Left) and Patient #2 (Right). (C) Body temperature (TEMP), C reactive protein (CRP) level and blood lymphocyte number (LYM) changes in patient #1 (left) and patient #2). (D) Hepatic function changes in patient #1 (Left) and patient #2 (right). ALT: alanine aminotransferase AST: aspartate aminotransferase; TP: total protein; ALB: albumin.

Figure 6:
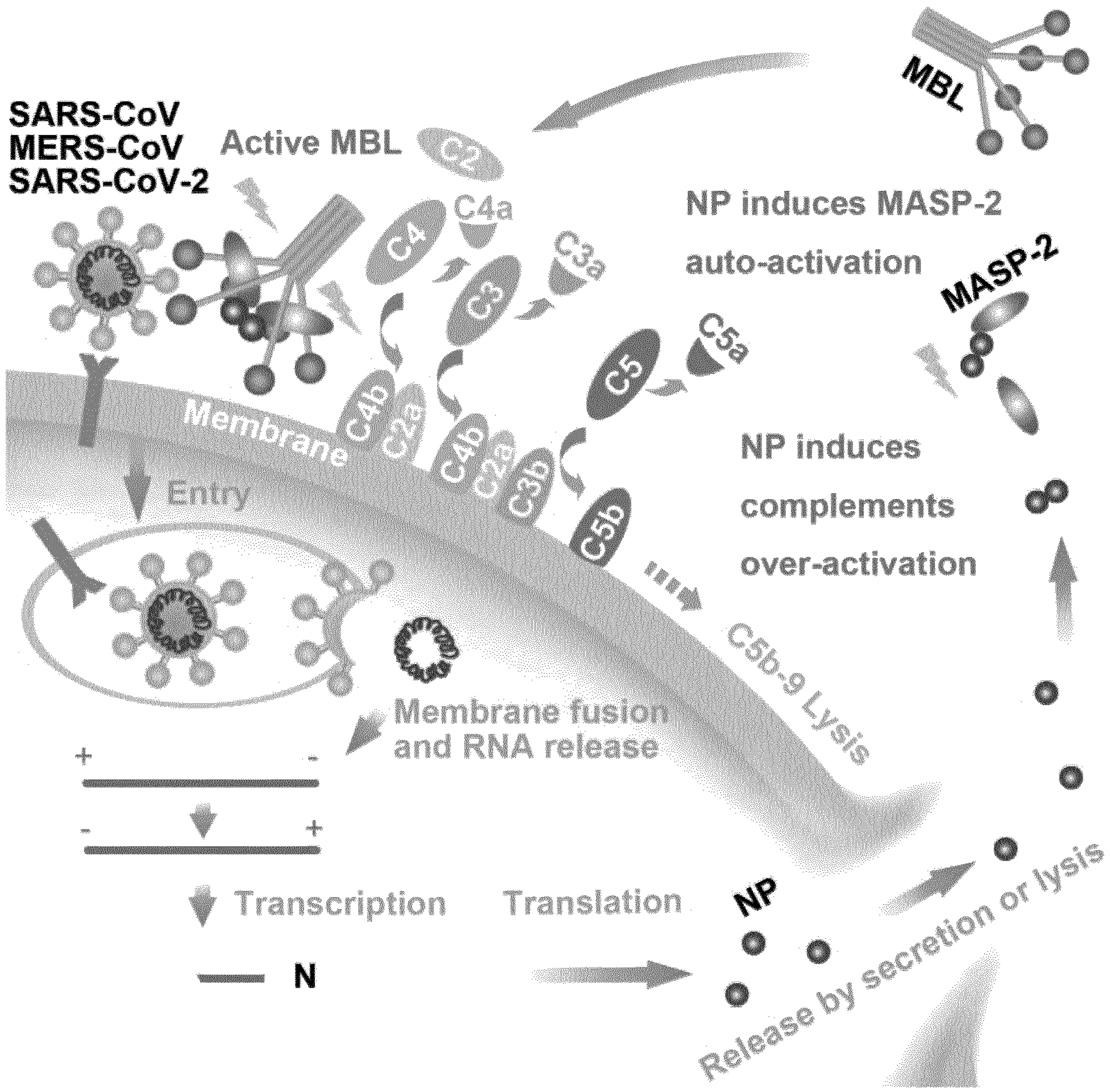

FIG. 6. Schematic representation of MBL pathway overactivated by N protein of SARS/MERS-CoV or SARS-CoV-2

(A) Virus binds to cell surface and S protein actives MBL. (B) Virus enters cells and expresses viral proteins including N protein. (C) N proteins release after cells lysis by virus replication and immune system attack. (D) The extracellular soluble N protein dimmers interact with MASP-2, induce MASP-2 auto-activation and binding to MBL. (E) The accelerated activation of MASP-2 induces complements cascades over-activation downstream of MBL pathway, and promotes cell lysis and N protein releases by secretion or complement mediated cytotoxicity, which may result in uncontrolled tissue damage and inflammation.

Figure 7:
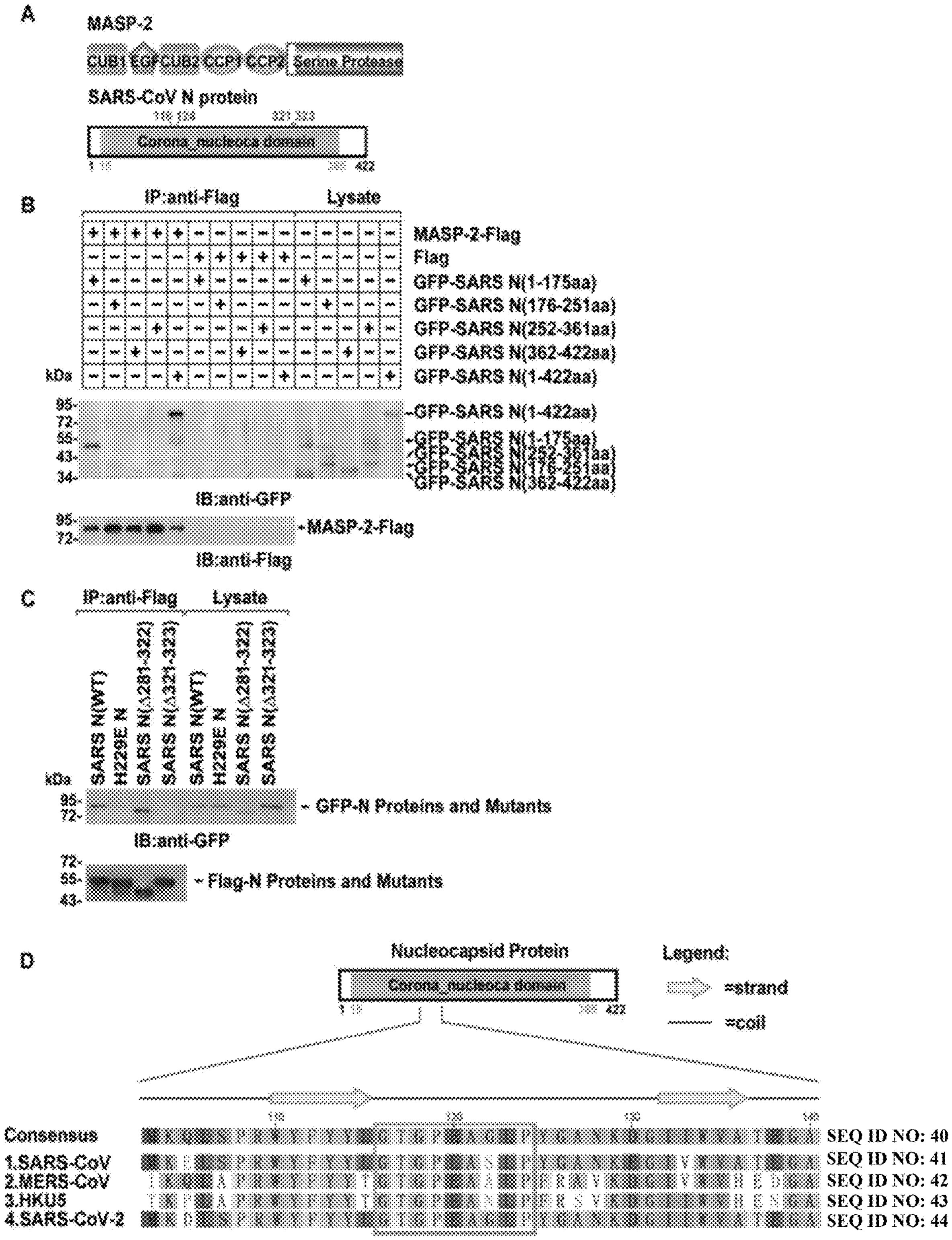

FIG. 7. Identifying key motif of N protein involved in the interaction with MASP-2.

(A) Domains and mutants of MASP-2 and SARS-CoV N protein. (B) Lysates from 293T cells transfected with full-length GFP-N(1-422) and its truncated mutants 1-176, 176-251, 252-361, and 362-422 were subjected to immunoprecipitation with MASP-2-Flag-conjugated agarose beads in the presence of 2 mM $CaCl_2$) and analyzed by immunoblotting with anti-GFP and anti-Flag antibodies. Flag beads incubated with lysates from cells transfected with Flag-vector (pCDNA3-Flag) were used as a negative control. (C) Immunoprecipitation analysis of N protein dimerization.

Lysates from 293T cells expressing Flag-tagged SARS-CoV N, HCoV-229E N, or mutants of SARS-CoV N (Δ281-322, Δ321-323) were incubated with anti-Flag agarose beads, and the N-conjugated agarose beads were balanced and subjected to immunoprecipitation with lysates from 293T cells expressing corresponding GFP-tagged N protein and analyzed by immunoblotting with anti-GFP. (D) Comparison of the SARS-CoV N, MERS-CoV N, HKU5-CoV N, SARS-CoV-2 N and Bat-SARS like-CoV N sequences. The secondary structure elements are defined based on an ESPript algorithm. Lines indicate coils, and arrows represent β strands. In FIG. 7D, SEQ ID NOs: for the amino acid sequences shown are as follows: Consensus (SEQ ID NO: 40); SARS-CoV (SEQ ID NO: 41); MERS-CoV (SEQ ID NO: 42); HKU5 (SEQ ID NO: 43); and SARS-CoV-2 (SEQ ID NO: 44).

FIG. 8.

The N proteins of SARS-CoV and MERS-CoV accelerate the complement lectin pathway cascade. (A) The C4 cleavage rate mentioned in FIG. 2D was calculated from the formula truncated C4/(truncated C4+remaining C4)×100% after densitometric analysis and plotting. The data are presented as the mean±S.D. of three tests. *P<0.05 and P<0.01 by unpaired two-tailed Student's t-test. (B) The densitometric analysis of the C4 cleavage rate mentioned in FIG. 2**E. (C) C4 was incubated with MASP-2, MBL, mannan, MERS-CoV N protein, or mutant N protein at 37° C. for 1 hr or 2 hr. C4 and cleaved C4 fragment were measured with an anti-C4α chain antibody. (D) Activated C3 deposition in C1q depleted serum diluted in Ca—Mg (LP+AP) or Mg-EGTA buffer (AP only) in relation to N protein concentration. (E) Activated C3 deposition in relation to N protein concentration. (F) C5b-9 deposition in relation to N protein concentration. (G) Opsonocytophagic test of mouse macrophage in serum in the presence or absence of SARS-CoV nucleocapsid protein. HSA was used as a negative control. The points represent the mean values from two repeated experiments. Error bars, mean±S.D. *P<0.05 and **P<0.01 by unpaired two-tailed Student's t-test.

FIG. 9.

The SARS-CoV nucleocapsid protein accelerates the complement lectin pathway cascade in vivo. (A) Mice were infected three times (day 1, 2, 3) with $1\times10^8$ PFU Ad-N/Ad-null via the tail vein, and LPS (5 mg/kg) was given by nasal drip and via the tail vein on the 6th day. Mice were sacrificed 6 hr after LPS challenge. SARS-CoV N and MASP-2 complex formation in frozen lung sections was measured by in situ PLA using goat anti-MASP-2 antibody, mouse anti-N antibody, and the corresponding secondary reagents, as indicated by the red signals. Deposited C3c fragments were stained with FITC-labeled anti-C3c antibodies (green). Nuclei (blue) were counterstained with DAPI. LPS+Ad-null was the negative control mice of LPS+Ad-N shown in FIG. 3D. (B) A diagram for mouse Masp2 gene knockout. To create a Masp2 knockout mouse model (C57BL/6N) by CRISPR/Cas-mediated genome engineering, Exon 9 to exon 11 of the mouse Masp2 gene were selected as target sites.

FIG. 10

Chest computer tomography of the two patients. The most severe planars were shown. CT scan for patient #1 showed that severe pneumonia occurred in a different lung area compared to 6 day before anti-C5a administration.

EXAMPLES

Abstract

An excessive immune response contributes to SARS-CoV, MERS-CoV and SARS-CoV-2 pathogenesis and lethality, but the mechanism remains unclear. In this study, the N proteins of SARS-CoV, MERS-CoV and SARS-CoV-2 were found to bind to MASP-2, the key serine protease in the lectin pathway of complement activation, resulting in a constitutive complement activation, and aggravation of inflammatory lung injury. Either blocking the N protein-MASP-2 interaction or suppressing complement activation can significantly alleviate N protein-induced complement hyper-activation and lung injury in vitro and in vivo. Complement hyper-activation was also observed in COVID-19 patients, and promising suppressive effect was observed when the deteriorating patients were treated with anti-C5a monoclonal antibody. Complement suppression may represent a common therapeutic approach for pneumonia induced by these highly pathogenic beta-coronaviruses. The lectin pathway of complement activation is a target for the treatment of highly pathogenic coronavirus induced pneumonia.

Introduction

Severe acute respiratory syndrome (SARS), that was initially reported in Guangdong, China, in November 2002, is a highly contagious and deadly respiratory disease (1, 2). Severe acute respiratory syndrome coronavirus (SARS-CoV), was identified as the novel etiological agent of this disease. Nearly a decade after the SARS outbreak, a new zoonotic coronavirus, Middle East respiratory syndrome coronavirus (MERS-CoV), was identified as the etiological agent of Middle East respiratory syndrome (3). Recently, a new coronavirus, SARS-CoV-2 was first discovered in Wuhan, China and spread rapidly to other provinces in China and all over the world. As of 18 Mar. 2020, SARS-CoV-2 has infected more than 180,000 people with a fatality rate of 3.9%. Infection of the virus caused severe atypical pneumonia similar to SARS-CoV infection (4). Although the pathogenesis of these diseases are being aggressively investigated, it is still not well understood why the viral infections lead to respiratory failure with a high fatality rate (5). The SARS-CoV nucleocapsid (N) protein is a 46-kDa viral RNA-binding protein sharing only 20-30% homology with the N proteins of other known coronaviruses (6), whereas N proteins of the highly pathogenic coronaviruses are more similar, including SARS-CoV-2 (91%) and MERS-CoV (51%) by BLASTP (5, 7) (8). The N protein is one of the most abundant viral structural proteins in patient sera samples during SARS-CoV infection (9). Potentially N protein plays a role in the virus pathogenesis as the pre-administration of N protein, but not other viral proteins, via recombinant vaccinia virus (10) or Venezuelan equine encephalitis virus replicon particles (11) resulted in severe pneumonia in aged mice challenged with SARS-CoV.

The complement system functions as an immune surveillance system that rapidly responds to infection. Activation of the complement system resulted in pathogen elimination, inflammatory regulation adaptive immune responses. But dysregulated complement activation has been implicated in the development of acute lung diseases induced by highly pathogenic viruses (12, 13). The complement system can be activated via the classical pathway (CP), the lectin pathway (LP), or the alternative pathway (AP) (14). In the LP, mannan-binding lectin (MBL) (or ficolins) binds to carbohydrate arrays of mannan and N-acetylglucosamine residues on the surfaces of the viruses or the surfaces of virus-infected cells, resulting in the activation of MBL-associated serine protease-2 (MASP-2), the only known MBL-associated protease that can directly initiate the complement cascade (15, 16). MBL binds to SARS-CoV-infected cells in a dose-dependent, calcium-dependent, and mannan-inhibitable fashion in vitro, enhancing the deposition of complement C4 on SARS-CoV (17). The N-linked glycosylation site N330 on the SARS-CoV spike(S) protein is critical for the specific interactions with MBL (18). Although higher levels of activated complement C3 and C4 fragments were found in SARS patients, indicating activation of complement pathways (19, 20), the mechanism of SARS-CoV-induced complement activation is not well understood. It is also unknown whether a similar pathogenesis occurs in SARS-CoV-2 infection.

Previously, we demonstrated that the N protein interacts with a number of host proteins, including MAP19 (22), an alternative splicing product of MBL-associated serine protease-2 (MASP-2). Thus, in this study, the interactions of the SARS-CoV, MERS-CoV and SARS-CoV-2 N proteins with MASP-2 were intensively investigated, and the pathological effects of these interactions on host immunity and inflammation were also elucidated, which provide a mechanism support for immunomodulation-based therapy against current COVID-19 epidemic.

Results

N Proteins of SARS-CoV. SARS-CoV-2 and MERS-CoV Interact with MASP-2

To investigate the binding between the N protein of SARS-CoV and MASP-2, and to delineate the interacting domains of the two proteins, lysates of human 293T cells expressing Flag-tagged full-length MASP-2, the N-terminal CUB1-EGF-CUB2 region, or the C-terminal CCP1-CCP1-SP region (FIG. 7A) were subjected to anti-Flag immunoprecipitation using anti-Flag antibody-conjugated agarose beads. The immunoprecipitates were next incubated with 293T cell lysates expressing GFP-tagged SARS-CoV N protein (GFP-SARS N) or truncated mutants in the presence of 2 mM $CaCl_2$) or 1 mM EDTA. The adsorbates were probed with anti-Flag or anti-GFP antibodies by immunoblotting. Associations between Flag-MASP-2 and GFP-SARS N were observed only in the presence of $CaCl_2$) (FIG. 1A), in agreement with the requirement of $Ca^{2+}$ for MASP-2-MBL binding and MASP-2 auto-activation. The CCP1-CCP2-SP region of MASP-2 (FIG. 1A) and the N-terminal domain (residues 1-175) of the N protein (FIG. 7A and FIG. 7B) were crucial for the association, whereas negative controls, or other truncated regions did not bind, and GFP-tagged full-length or truncated N protein did not co-immunoprecipitate with mouse IgG conjugated beads (FIG. 1A and FIG. 7B).

SARS-CoV N protein can be detected in patient serum as early as 1 day after the onset of symptoms (24). To simulate the SARS-CoV N protein associations in serum, Flag-tagged N protein (1 ng/ml) was added to human or mouse serum and precipitated with anti-Flag antibody conjugated agarose beads. The SARS-CoV N protein interacted with MASP-2 derived from both human and mouse serum (FIG. 1B). Further truncation and deletion analysis showed that amino acid residues 116-124, which are located in a coil motif of the SARS-CoV N protein (residues 115-130), were indispensable for the interaction with MASP-2 (FIG. 1C). However, the association of MASP-2 with SARS-CoV NΔ321-323, a mutant that fails to form the N protein dimer (FIG. 7C), was not greatly affected (FIG. 1C).

The crucial motif in SARS-CoV N protein for MASP2 interaction (residues 116-124) share a high identity with the corresponding motif in SARS-CoV-2 N (115-123) and MERS-CoV N (104-112) (FIG. 7D), suggesting that the N protein of SARS-CoV2 and MERS CoV will also interact with MASP2. As expected, exogenously expressed MERS-CoV N and SARS-CoV-2 N both associated with MASP-2 (FIGS. 1D and 1E), and the Δ104-112 deletion mutant of MERS-CoV N exhibited the predicted reduced association (FIG. 1D). Therefore a common motif across coronavirus N proteins is important for MASP-2 binding.

N Proteins of SARS-CoV, MERS-CoV and SARS-CoV-2 Potentiate MASP-2-Dependent Complement Activation The CCP1-CCP2-SP domains of MASP-2 are responsible for self-activation and substrate binding activity, which in turn mediates complement lectin pathway activation (25). The MASP-2: SARS-CoV N protein association demonstrated above suggests that N protein may regulate MASP-2 activation and cleavage requiring dimerization. To demonstrate MASP-2: MASP-2 binding, Flag-tagged-MASP-2-conjugated beads were incubated with lysates of 293T cells expressing Myc-tagged MASP-2 in the presence/absence of N protein and MBL. Binding of MASP-2-Myc to MASP-2-Flag was potentiated by the SARS-CoV N protein, at an approximately equal molar stoichiometry (FIG. 2A). Next, purified MASP-2-Flag was incubated with mannan and MBL with or without SARS-CoV N protein. Higher levels of the cleaved MASP-2 fragments (residues 445-686) resulting from MASP-2 auto-activation were produced in the presence of SARS-CoV N protein (FIG. 2B).

To investigate the effect of SARS-CoV N protein on the MBL-binding capability of MASP-2, purified MBL and MASP-2 (26) were incubated in mannan-coated microplate wells at 4° C. to avoid MASP2 activation, and the dynamics of MASP-2: MBL binding were assessed using an anti-MASP2 antibody. Compared with human serum albumin (HSA), a high-concentration component in binding buffer used as a negative control for N protein, the binding of MASP-2 to MBL was significantly enhanced in the presence of SARS-CoV N protein at relatively low concentration (1%~0.1% of MASP2) and $Ca^{2+}$, and the potentiation was effectively reversed by anti-N protein antibody (FIG. 2C). Moreover, SARS-CoV N protein bearing the 4116-124 or Δ321-323 deletion or N protein from the less pathogenic human coronavirus 229E-CoV showed little or no effect on MASP-2: MBL binding compared with the full-length SARS-CoV N protein (FIG. 2C). These results indicated that SARS-CoV N protein-potentiated MASP-2 activation is dependent not only on MASP-2 association but also on N protein dimerization.

Figure 8:
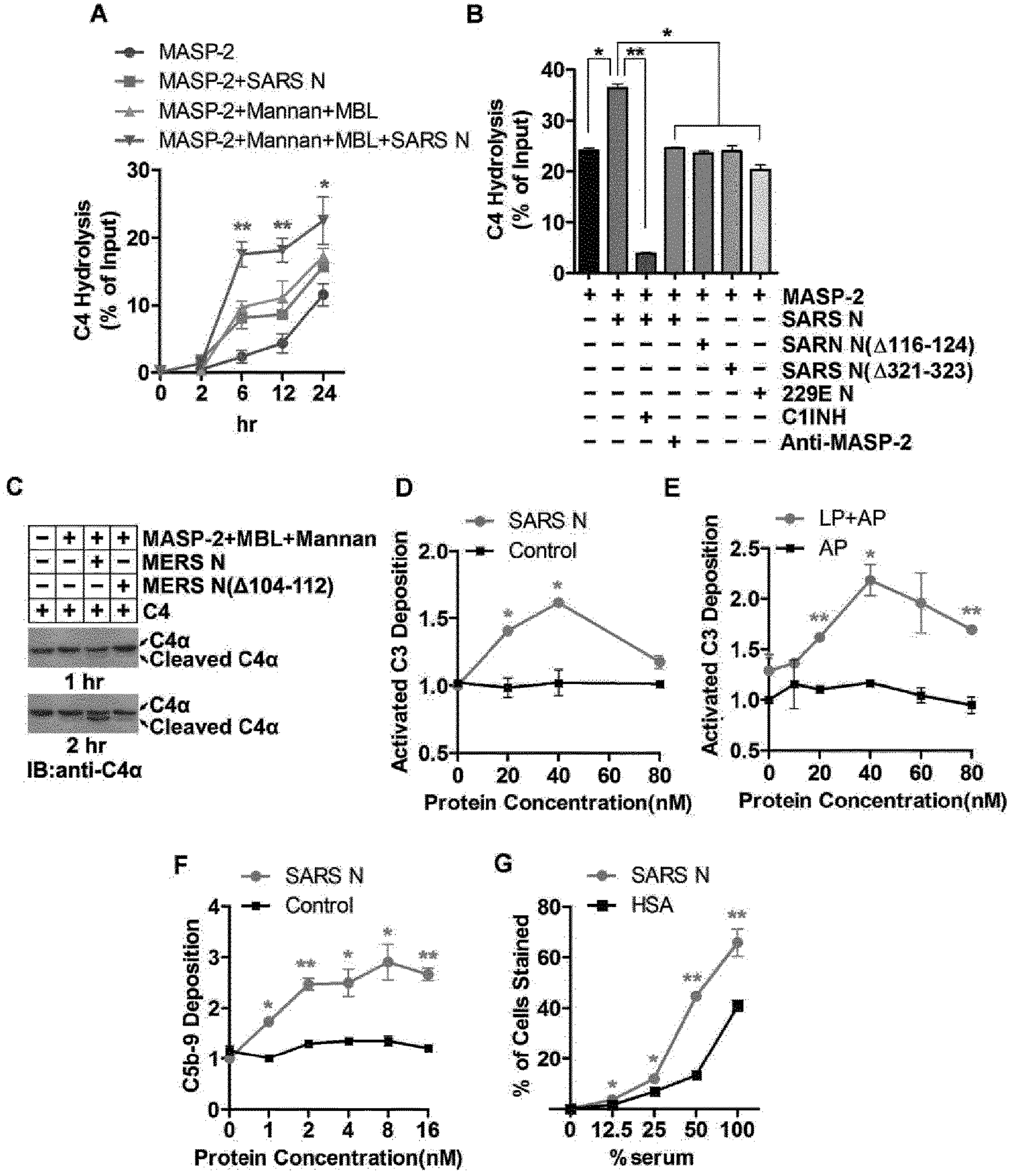

MASP2 cleaves complement components C2 and C4 to generate C3 convertase in the lectin pathway of the complement system upon activation. Next, the effect of the SARS-CoV N protein on LP complement activation was assessed by C4 cleavage. Purified C4 was incubated with MASP-2, Mannan, MBL in the presence/absence of equal molar N protein, and C4 cleavage was observed to be significantly potentiated by the SARS-CoV N protein in the presence of mannan and MBL (FIG. 2D and FIG. 8A). Accordingly, mutants of SARS-CoV N protein (Δ116-124 and Δ321-323) as well as N protein from H229E-CoV failed to promote MASP-2-mediated C4 hydrolysis (FIG. 2E and FIG. 8B). Notably, an anti-MASP-2 monoclonal antibody or C1INH, an inhibitor of MASP-2 (27), blocked SARS-CoV-potentiated C4 hydrolysis, suggested that N protein-potentiated C4 cleavage was dependent on MASP-2 activation (FIG. 2E and FIG. 8B). Moreover MERS-CoV N also found potentiate the C4 cleavage (FIG. 8C). These results indicated that N protein prompts C4 cleavage and therefore complement activation by MASP-2 association and activation.

The impact of SARS-CoV N protein on complement activation via the lectin pathway was further investigated by complement deposition assays. Purified C4 was incubated with immobilized MBL MASP-2 complex in the presence of indicated N protein. The N protein of SARS-CoV, MERS-CoV and SARS-CoV2 but not the H229E-CoV N potentiated C4b deposition, which was dependent on the activity of MASP 2, in a dose dependent manner (FIG. 2F, FIG. 2G and FIG. 2H). Then, immobilized mannan was incubated with C1q depleted serum (to eliminate the classical pathway) (28) in the presence/absence of SARS-CoV N protein, and the deposited C3 fragments (C3b, iC3b and C3dg) were detected by an anti activated C3 antibody. In concert with C4b deposition, the deposition of activated C3 was evidently increased along with the increase in SARS-CoV N protein levels up to ~40 nM (FIG. 8D), suggesting enhanced activity of the C3 convertase. C3b deposition was decreased in the presence of a high concentration of N protein (FIGS. 8D and 8E), possibly due to further cleavage of C3b by soluble inhibitors in serum (such as factor H and factor I) when the surface is coated with high densities of C3b (29, 30). In addition, SARS CoV N protein had little or no effect on activated C3 deposition in calcium free buffer containing EGTA, which suggests that SARS CoV N protein potentiated C3 activation occurs through the lectin pathway (LP) but not the alternative pathway (AP), in which C3 activation is $Ca^{2+}$ independent (FIG. 8E). We further tested the deposition of the C5b 9 complex. As a result of amplified complement cascades, significantly increased deposition of the complex was induced by SARS-CoV N protein at a much lower concentration similar to that observed in patient sera (FIG. 8F) (24).

Activated complement plays a crucial role in the efficient phagocytosis of pathogens and cellular debris by C3b or C5b-mediated opsonization (31). To study complement-dependent phagocytosis, *E. coli* and mouse peritoneal macrophages were incubated together in diluted C1q-depleted serum with or without SARS-CoV N protein. Bound C3 or its large fragment C3b, the product after C3 cleavage, was stained with FITC-labeled anti-C3c antibody, and the FITC-positive macrophages containing C3-conjugated *E. coli* were counted under a microscope. In concert with complement activation, complement-dependent phagocytosis by mice peritoneal macrophage in the presence of mouse serum containing complement component including MASP-2 was enhanced by SARS-CoV N protein compared with the HSA control (FIG. 8F). These findings indicated that SARS-CoV N protein effectively prompted the activation and opsonic effect of the complement system through a non-classical pathway.

N Proteins of SARS-CoV and MERS-CoV Aggravates LPS Induced Pneumonia by MASP-2 Involved Complement Activation Persistent activation of complement leads to uncontrolled inflammation. To investigate the effect of N protein-potentiated MASP-2 activation on inflammation, mice were pre-infected with adenovirus ($1\times10^9$ PFU) expressing SARS-CoV N (Ad-SARS N) or its mutant or adenovirus vehicle only (Ad-null). The mice were then challenged with LPS, which contains MBL-binding motifs, to activate LP and induce inflammation (32). 8 of 10 mice pre-exposed to adenovirus vehicle survived when challenged with 5 mg/kg LPS (FIG. 3A), while all 10 mice pre-exposed to Ad-SARS N died within 12 h after LPS administration at the same dosage (FIG. 3A). Severe lung damage and massive inflammatory cell infiltration were also observed in dead mice (FIG. 3B). In concert with previous findings, the pre-infection of Ad-229E N and Ad-SARS N bearing the Δ116-124 or Δ321-323 deletion in the N protein, respectively, had significantly reduced effects on mouse mortality. Importantly, when anti-MASP-2 antibody or C1INH was administered simultaneously with LPS administration in the Ad-SARS N pre-infected mice, the death rate induced by LPS was significantly decreased (FIG. 3A). Severe lung damage and massive inflammatory cell infiltration were also observed in these mice (FIG. 3B). These results collectively demonstrate that the SARS-CoV N protein greatly potentiated LPS-induced inflammation via MASP-2 activation which thereby initiates LP-involved complement cascade reaction.

To investigate the complement activation in mice induced by LPS and N protein, mice pre-infected with Ad-SARS N ($1\times10^8$ PFU) were challenged with LPS (5 mg/kg). At 6 hr post LPS administration, the mice were sacrificed, and the paraformaldehyde-fixed lung tissue was subjected to immunohistochemical staining with anti-C4b antibody (FIG. 3C) or immunofluorescence analysis with FITC-labeled anti-C3c antibody (FIG. 3D). The C4b and activated C3 deposition in the lung were significantly increased in mice expressing SARS-CoV N protein compared with the weak staining in the lungs of mice treated with LPS and Ad-null (FIGS. 3 C and D).

The in vivo association of MASP-2 with the N protein was further assessed by in situ proximity ligation assay (PLA) with anti-N and anti-MASP-2 antibodies (FIG. 3D, FIG. 9A), and red spots, which were only detectable when SARS-CoV N and MASP-2 bind to each other, were abundantly observed in pulmonary cells from mice expressing SARS-CoV N but not negative control animals. These results confirmed an in situ direct binding and activation of MASP-2 by SARS-CoV N in mice lung tissue.

Similarly, mice challenged with LPS suffered serious pneumonia and 100% die within 24 h when pre-infected with adenovirus expressing MERS-CoV N protein (Ad-MERS N) but not its Δ104-112 mutant (Ad-MERS NΔ104-112) for 7 days, which was partially rescued by CHINH and anti-MASP-2 antibody (FIG. 3E). These results indicate that the N protein is employed by both SARS-CoV and MERS-CoV to promote complement activation through the MASP-2-mediated lectin pathway.

Figure 9:
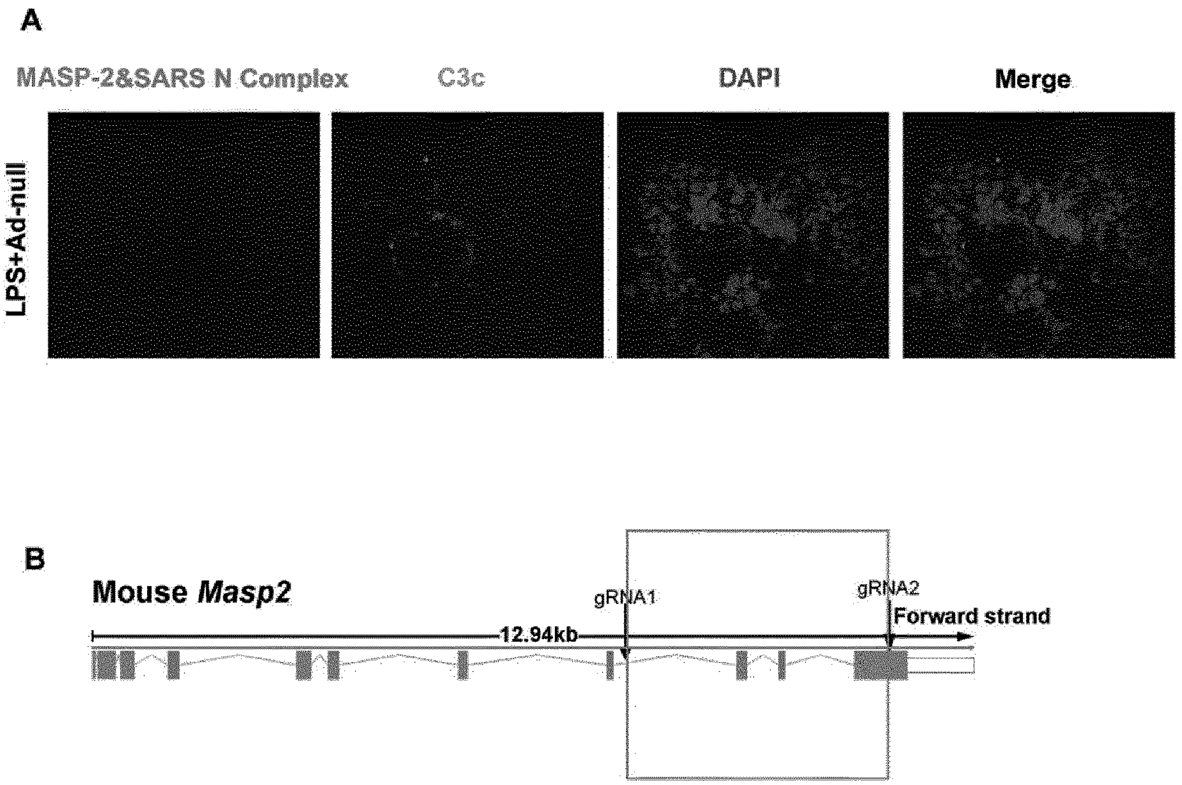

The pathogenicity of N protein was further investigated using masp2 knockout mice with MASP-2 protease activity deficiency by the same way (FIG. 9*b*). Mice were pre-infected with Ad-SARS N or Ad-MERS N ($1\times10^8$ PFU) for 5 days, and then challenged with LPS. Compared with wild-type mice, masp2 knockout mice survived longer and had a higher survival rates (FIG. 3F), which may be attributed to a compromised complement activation because of MASP-2 deficiency.

Complements Cascade is Overactivated in Lungs of COVID-19 Patients

Because the SARS-CoV and SARS-CoV-2 induce only mild lung damage in mice, and investigation with live SARS-CoV including mouse adapted SARS-CoV is not allowed by the regulation, clinical evidence that the over-activation of complement LP pathway occurred in COVID-19 patients was obtained. The paraformaldehyde-fixed lung tissue of patients who died of COVID-19 were collected and subjected to immunohistochemical staining with MBL, MASP-2, C4α, C3 or C5b-9 antibodies. The MBL, MASP-2, C4, C3 and C5b-9 in the patient lung tissue were strongly positive staining (FIG. 4), which suggests that the complement components were deposited in type I and type II alveolar epithelia cells, as well as inflammatory cells, some hyperplastic pneumocytes, and exudates in alveolar spaces with necrotic cell debris. Further, significantly increased serum C5a level was also observed in COVID-19 patient, particularly in critical patients. These results indicate that complement pathways were aggressively activated in the lungs of COVID-19 patients.

Complement-Targeted Therapy Shows a Promising Curative Effect Against COVID-19

The excessive inflammatory and cytokine storm may contribute to the severity and lethality of COVID-19, which may be attributed to the unrestrained activation of complement pathway. Therefore, downregulation of MASP-2 as well as its downstream signal molecules, such as the potent anaphylatoxin C5a, may provide a new approach to control the pneumonia induced by the SARS-CoV-2.

Based on our finding and its potential and application in COVID-19 therapy, a recombinant C5a antibody comprising the variable heavy chain sequence of SEQ ID NO: 34 and the variable light chain sequence of SEQ ID NO: 35 (an IgG antibody with these variable regions grown from the same cell line is called interchangeably IFX-1 or BDB-001), which was in phase II clinical trial for hidradenitis suppurativa, was rapidly approved by National Medical Product Administration (NMDA) for phase II clinical trial for the treatment of COVID-19 (2020L0003). "A multicenter, randomized double blind placebo-controlled trial in mild COVID-19 patients" and an open label "two cohort clinical trial in patients with severe and critical COVID-19" were carried out simultaneously under approval from ethic committee of Huoshensan Hospital with the informed consent from the patients. While the larger dataset from more patients in the COVID-19 cohort will be reported elsewhere when the trial was finished, here we report the first 2 patients administrated with anti-C5a therapy in the open label trial.

Figure 10:
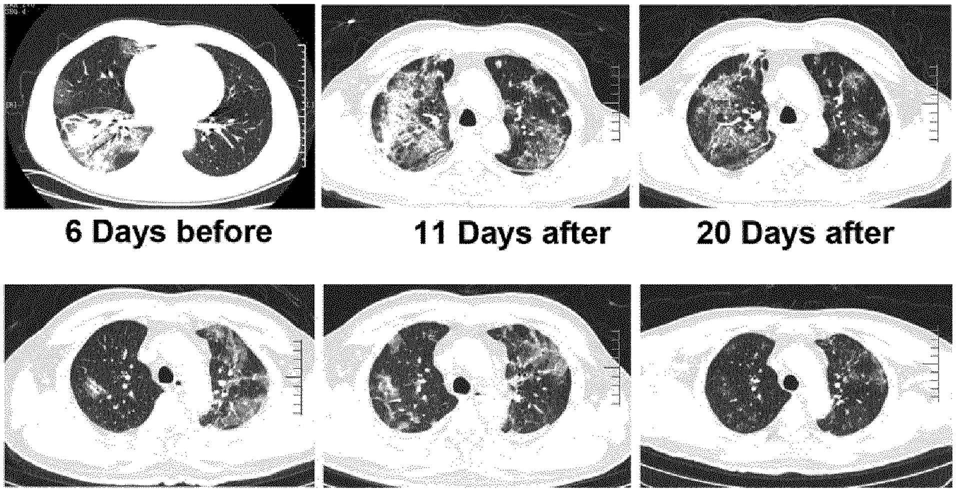

Patient #1, a 54 years old male resident in the city of Wuhan, was admitted to Dongxihu Hospital on the 4th day after the onset of symptoms (5th day of illness) with fever. Infection of SARS-CoV-2 was confirmed by rRT-PCR for SARS-CoV-2, and chest CT scan showed bilateral opacities. The disease was getting worse from day 9 of illness, with high fever (38.7° C.~39.8° C.), $SpO_2$<93% on room air, pneumonia progression on CT scan, and severe hepatic damage. Prednisone (40 mg/day for 4 days) was administrated on day 10 through 13 of illness but the condition deteriorated, so the patient was transferred to Wuhan Huoshenshan Hospital, a new hospital established urgently for severe COVID-19 patients, on the day 14 of illness (FIG. 5A), and was considered as severe case in critical condition with moderate ARDS (oxygenation index <150), respiratory rate 30/min and the Percutaneous oxygen saturation ($SpO_2$) drop to 77% when exposed to room air for 1 minute. Supportive care was provided including high-flow nasal oxygen (HFNO) to target $SpO_2$>95% (FIG. 5B, left). He was also administrated with the antibiotics (moxifloxacin) and human serum albumin, while prednisone was discontinued. Treatment with anti-C5a monoclonal antibody (BDB001) was initiated on the morning of day 15 of illness. The antibody was given intravenous in 250 ml saline, at a dosage of 300 mg/d, on day 1, 2, 3, 5, 7, 9, 11 and 13. No adverse event was observed and the clinical condition improved in the next days, with normal body temperature in the evening of the same day (FIG. 5C, left), increased oxygenation index ($PaO_2/FiO_2$) (FIG. 5B, left) and lymphocyte cell number (FIG. 5C, left), decreased C reactive protein (CRP) concentration (FIG. 5C, left), and significantly improved hepatic function (shown by decreased ALT, AST, and increased total serum protein and serum albumin concentration, FIG. 5D, left). The fraction of inspiration $O_2$ and the gas flow rate of high—flow nasal oxygen (HFNO) was eventually decreased from the highest (80%, 40 L/min to 30%, 20 L/min) to target a $SpO_2$>95% (FIG. 5B, left). Because of the high risk taking the patient in critical condition to CT scan in the temporarily established hospital (distance and the raining weather), no CT scan just before anti-C5a administration was available for evaluation. Nevertheless, the pneumonia had significantly improved 20 days after $1^{st}$ dose in comparison to 10 days after the $1^{st}$ dose (FIG. 10).

Patient #2 was a 67 years old male who was admitted to the sixth hospital on the 5th day after the onset of symptoms (6 day of illness) with fever and cough. CT scan showed opacity on the superior lobe of left lung (FIG. 10). Infection of SARS-CoV-2 was also confirmed by rRT-PCR at day 11 of illness. Anti-viral (Arbidol) and antibiotics (moxifloxacin) was administrated together with other supportive treatment. Condition was worsening by day 8 with severe cough and high fever (39.7° C., FIG. 5C, right). Methylprednisolone (40 mg/day, for 7 days from the 8th day after illness) showed little if any improvement of symptoms. The patient was transferred to Wuhan Huoshenshan Hospital on day 10 (FIG. 5A) and the illness continued getting worse as shown by $SpO_2$ (<90% on room air on day 14), high fever (>39° C. on day 10-13, FIG. 5C right) and pneumonia on chest CT on day 11 of illness (FIG. 10). The patients reported severe cough, chest tightness and dyspnea. HFNO has to be given to maintain $SpO_2$>95%. Anti-C5a was administrated on the morning of illness day 14, and continued as in the patient #1. Subsequently, a normal temperature was observed on the same day (FIG. 5C right). Cough, dyspnea and oppression in chest were reported to be getting better the next day (Day 15 of illness). A significant decreased C reactive protein (CRP) level, significantly increased white blood cell and lymphocyte number were also observed in the next days (FIG. 5C, right). Hepatic function was gradually improved (FIG. 5D right, data on day 15 are not available). Flow rate and Fraction of inspiration $O_2$ necessary to maintain $SpO_2$>95% gradually decreased, with the increasing $SpO_2/FiO_2$ (FIG. 5B right). Chest CT on day 26 (12 days after $1^{st}$ dose) also showed reduced pneumonia (FIG. 5B).

These data suggested that 2 patients significantly benefited from anti-C5a monoclonal antibody therapy.

Discussion

In the past 17 years, successively emerged SARS-CoV, MERS-CoV and SARS-CoV-2 broke through the species barrier and brought new infectious diseases and social panic to human. All these highly pathogenic coronavirus cause acute lung injury and acute respiratory distress syndrome (ARDS), therefore resulting in an increased severity and lethality. Patients infected with the virus may develop atypical pneumonia resulting from severe immune injury. The excessive human immune responses that were characterized by the extensive release of pro-inflammatory cytokines and chemokines, called a "cytokine storm" (5), is thought to be the major initiator of the severe pneumonia caused by highly pathogenic coronavirus, including the latest SARS-CoV-2 (4). Although immunopathogenesis has been partially implicated in SARS or MERS, the mechanism responsible for virus-induced hyperactivation of host immune system remains poorly understood.

Figure 1:
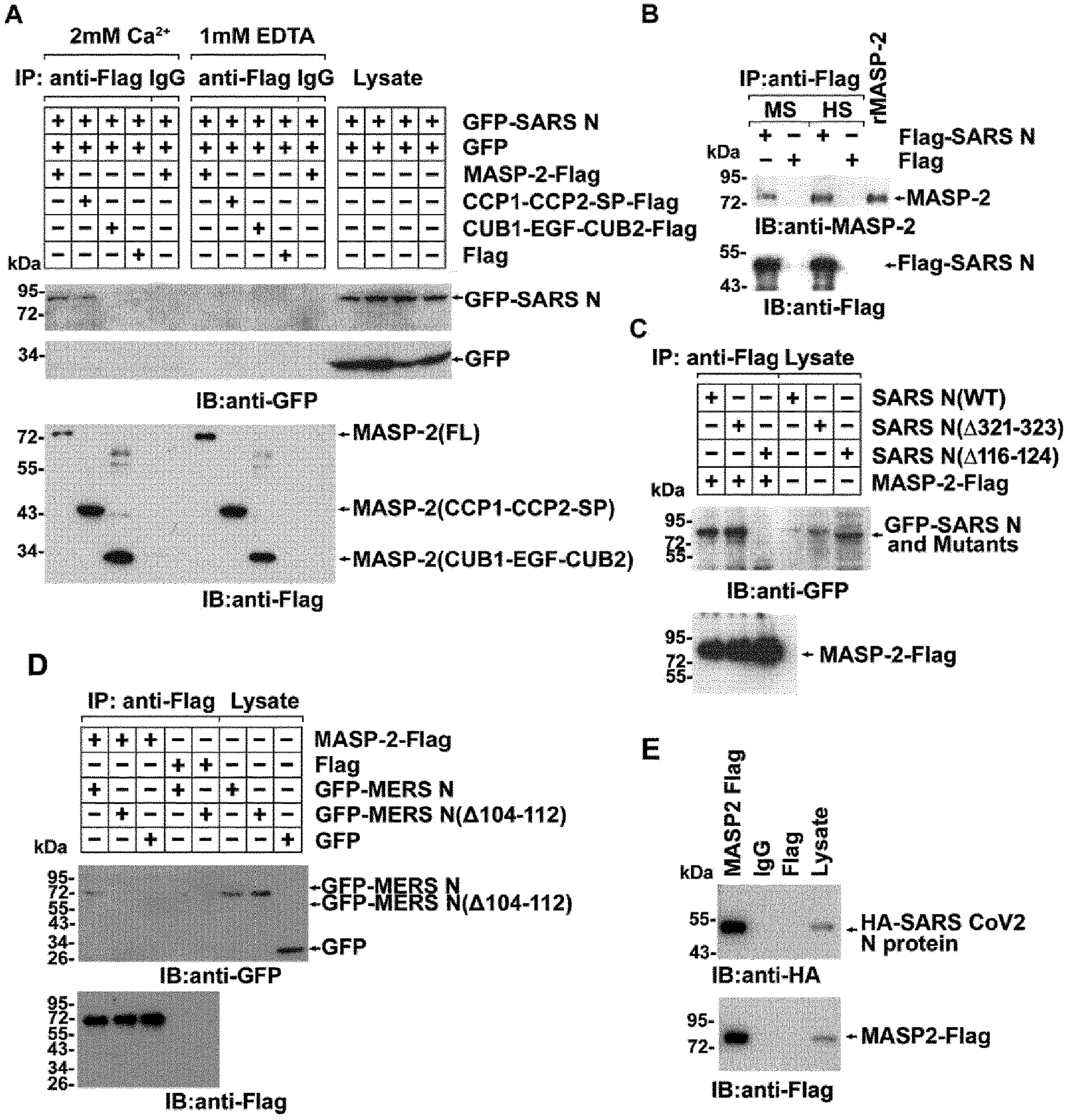
FIG. 1. The nucleocapsid proteins of SARS-CoV, MERS-CoV and SARS-CoV 2 bind to MASP-2.

Here the inventors disclose that SARS-CoV, MERS-CoV and SARS-CoV-2 share a common mechanism connecting the viral N proteins to binding and potentiation of an MBL, $Ca^{2+}$-dependent auto-activation of MASP-2, leading to the uncontrolled activation of complement cascade, complement deposition, and enhanced cleavage of C4 (FIGS. 1-2, and 6). The binding of N protein to MASP-2 amplifies the effects of MASP-2-mediated-lectin pathway activation. N protein mutants either fail to interact with MASP-2 or fail to form an N dimer and have little or no effect on MASP-2-mediated lectin pathway activation (FIGS. 1C and D), suggesting that the effects of N protein are dependent on binding and dimerization.

As a "double-edged sword", complement is critical for innate immunity against pathogens. Anaphylatoxins, such as C3a and C5a, can activate immune cells, and therefore induce the release of various cytokines. Activated complement cascade produces the cytolytic terminal complement complex C5b-9 and the $C_3b$ and C5b fragments (31, 33). These peptides induce the synthesis of arachidonic acid metabolites, including prostaglandin (PG) E2, thromboxane B2 and leukotrienes (32, 34), which further induce the recruitment and activation of neutrophils, monocytes and eosinophils, and stimulate the production of a number of pro-inflammatory cytokines and mediators (35). These cytokines trigger and maintain inflammatory processes and help the innate immunity to fight the virus. Nevertheless, complement-involved innate immunity activation must be fine-tuned because unrestrained complement activation always contributes to disseminated intravascular coagulation (DIC), inflammation, cell death, and immune paralysis and ultimately leads to multiple organ failure and death. The surprising finding that the coronavirus N protein potentiates complement activation provides a new insight into the causation of pneumonia induced by SARS-CoV, MERS-CoV and SARS-CoV-2 infection. Additionally, we also discovered that the pre-infection of Ad-SARS N or Ad-MERS N evidently increased the fatality of LPS-induced pneumonia (FIG. 3), It possibly also aggravates tissue damage caused by the massive LPS released from secondary bacterial infections (37, 38).

The involvement of N protein-mediated MASP-2 and therefore the complement cascade over-activation in the pathogenesis of coronavirus provides a strategy to use known inhibitors of the C5a/C5aR pathway and, thus to new ways to treat SARS, MERS or the latest COVID-19. Firstly, neutralization of N protein in the serum by antibody effectively alleviated lung injury and reduced the fatality in LPS/Ad-SARS N or LPS/Ad-MERS N challenged mice. Coincidentally, SARS patients who produce higher levels of N protein specific but not Spike specific antibodies tend to recover more easily, suggesting that levels of N antibodies correlated with outcome of SARS (39). According to our findings, similar mechanisms may be present in MERS-CoV or SARS-CoV-2 infection.

Secondly, Masp2 knockout mice showed significantly mild symptoms and a shorter course of disease in LPS induced, N protein boosted mice pneumonia model, confirmed the harmful role of MASP-2 in this severe pneumonia. Accordingly, administration of anti-MASP-2 antibody or the MASP-2 inhibitor CHINH showed a promising treatment effect (FIG. 3). Improved MASP-2 antibodies that have higher affinity and neutralization activity, such as OMS721 (40) (which showed promising effects on thrombotic microangiopathy), or an injectable C1INH medicine, such as HAEGARDA, may provide effective protection. Further clinically evaluation is of value to be carried out for the treatment of SARS-CoV 2 induced pneumonia treatment.

Thirdly, we've observed an excessive activation of complement cascade in lung tissue of dead patient, which is coincident with the observation in Ad-SARS N pre-infected and LPS-primed mice model. High-level C5a was accumulated in the serum of severe but not mild COVID-19 patients. So, it will make sense that complement cascade products-targeted immunomodulation may be effective for inflammation-control in pathogenic coronavirus-related diseases. In this pathway, C5a is the most potent complement protein triggering inflammation. Based on our observation and the safety record in phase II trial in other disease by Staidson (BDB001) and inflaRx GmbH (IFX-1, produced by the same engineered cell line), recombinant anti-C5a antibody BDB001 was approved by NMDA for the clinical trial for treatment of severe and critical COVID-19 patients. At least in the first two patient that were both in deteriorating condition, the anti-C5a antibody showed rapid and promising effect exceeding the expectation of clinical physicians. Although the final efficacy will be released until the clinical trial is finished, it is worth to expect that anti-C5a antibody would provide a new approach for the treatment of COVID-19.

Material and Methods

Cell Culture and Transfections

The 293T cell line was obtained from the Cell Resource Center of Peking Union Medical College. Cells were grown in Dulbecco's modified Eagle's medium (DMEM) (Invitrogen) supplemented with 10% heatinactivated fetal bovine serum (FBS) (HyClone), 2 mM L-glutamine, 100 units/ml penicillin, and 100 μg/ml streptomycin. Cells were transfected with plasmid DNA using Lipofectamine 2000 (Invitrogen) according to the manufacturer's protocol.

Vectors and Epitope Tagging of Proteins

The N gene of SARS-CoV (GenBank Accession #AY274119) was amplified by RT-PCR from the SARS-CoV RNA of patient serum samples (Upstream 5'-primer: CGGAATTCCATATGTCTGATAATGGACCCCAA-3', SEQ ID NO: 38; downstream primer: 5'-CGGGATCCT-TATGCCTGAGTTGAATCAGC-3', SEQ ID NO: 39) and cloned into the pcDNA3-based Flag vector (Invitrogen), pCMV-Myc (Clontech), pGEX-4T-2 (GE Health care), and the BglII and EcoRI sites of pEGFPC1 (Clontech). The N gene of MERS-CoV was chemically synthesized (Huaxinrcomm Technology Co., Ltd) and cloned into the pcDNA3-based Flag vector at the BamHI and EcoRI sites. The N gene of SARSCoV-2 was chemically synthesized (General Biosystems (Anhui) Co. Ltd) and cloned into the pcDNA3.1-based HA vector at the KpnI and XbaI sites.

Immunoprecipitation and Immunoblotting.

Cell lysates were prepared in lysis buffer (50 mM Tris-HCl, pH 7.5, 1 mM phenylmethylsulfonyl fluoride, 1 mM dithiothreitol, 10 mM sodium fluoride, 10 μg/ml aprotinin, 10 μg/ml leupeptin, and 10 μg/ml pepstatin A) containing 1% Nonidet P-40. Soluble proteins were subjected to immunoprecipitation with anti-Flag M2 agarose (Sigma). The adsorbates were then separated by SDS-PAGE and transferred onto an Immobilon-P transfer membrane (Millipore) by semi-dry transblot (Biorad). The membrane was blocked by 5% Western-Blocker (Biorad). Immunoblot analysis was performed with horseradish peroxidase (HRP)-conjugated anti-Flag (Sigma), anti-β-actin (Sigma), anti-green fluorescent protein (GFP) (Clontech), anti-MASP-2 (Santa Cruz), anti-C4α (Santa Cruz), HRP-conjugated anti-Myc (Santa Cruz), and goat anti-mouse immunoglobulin G (IgG) (Amersham/Pharmacia) antibodies. The antigen-antibody complexes were visualized by chemiluminescence (GE Health Care).

Purification of SARS-CoV and MERS-CoV N Protein.

As described previously (1), pET22b-SARS/MERS-CoV N was transformed into the expression strain BL21 (DE3). After induction with 1 mM IPTG for 8 h, the bacteria were harvested by centrifugation and resuspended in buffer A (25 mM $Na_2HPO_4/NaH_2PO_4$ (pH 8.0), 1 mM EDTA, and 1 mM DTT) before sonication. Soluble N protein in the lysate was purified with ion-exchange chromatography with SP-Sepharose Fast Flow (25 mM $Na_2HPO_4/NaH_2PO_4$ (pH 8.0), 1 mM EDTA, 1 mM DTT, and 0.35-0.5 M NaCl), followed by Superdex 200 gel filtration (GE Healthcare) and elution with buffer A. *E. coli* transformed with the vector pET22b was lysed as described above, and the eluate was used as a negative control for the purified N protein. Purified SARS-CoV-2 N-His was obtained from General Biosystems (Anhui) Co. Ltd.

Purification and Renaturation of MASP-2.

Recombinant protein expression and renaturation were performed as described (2, 3). In brief, pET22b-MASP-2 was transformed into the expression host strain BL21 (DE3). After induction with 1 mM IPTG, cells were harvested and sonicated. The inclusion bodies were solubilized in 6 M GuHCl, 0.1 M Tris-HCl (pH 8.3), and 100 mM DTT at room temperature; the solubilized proteins were then diluted into refolding buffers containing 50 mM Tris-HCl, 3 mM reduced glutathione (Sigma), 1 mM oxidized glutathione (Sigma), 5 mM EDTA, and 0.5 M arginine. The protein samples were then cooled to 4° C. The renatured protein was dialyzed against 20 mM Tris, 140 mM NaCl, pH 7.4 at 4° C., concentrated with PEG8000, aliquoted, and stored at −70° C. To obtain high-activity MASP-2, Flag-tagged MASP-2 was expressed in 293T cells, precipitated with anti-FLAG magnetic beads, and eluted with Flag peptide (Sigma). The concentration of MASP-2 was assessed using a BCA kit and immunoblot analysis, with the purified prokaryotic-expressed MASP-2 as a standard control.

MASP-2 Auto-Activation and C4 Cleavage Assay.

Purified MASP-2 (8 nM) was incubated at 37° C. in 20 mM Tris-HCl (pH 7.4), 150 mM NaCl, and 2 mM CaCl2 with purified C4 (Calbiochem), recombined MBL (Calbiochem), mannan (Sigma), and SARS-CoV N protein at concentrations of 50 nM, 30 nM, 15 ng/ml, and 10 nM, respectively. The cleavage was followed by SDS-PAGE under reducing conditions, and the C4 fragments and MASP-2 were detected by immunoblot analysis with anti-C4α chain antibody (Santa Cruz) or anti-Flag antibody (Sigma).

Complement Deposition Assay.

The C4b deposition assay was performed using a human MBL/MASP-2 assay kit (Hycult biotech) (4). In brief, diluted serum was incubated in mannan-coated plates with high salt binding buffer overnight at 4° C. and removed by washing, and the MBL-MASP-2 complex was captured. Purified C4 and N protein were added and incubated for 1.5 hr, and the deposited C4b was detected following standard protocols. The functional activity of LP and AP was assessed by ELISA as previously described (5). Nunc Maxisorb plates were coated with 10 μg mannan per well in 100 mM $Na_2CO_3/NaHCO_3$ (pH 9.6) at room temperature overnight. After each step, plates were washed three times with PBST (300 μl/well). Residual binding sites were blocked by incubation with 10 mM Tris-HCl (pH 7.4), 150 mM NaCl, and 2% HSA for 2-3 hr at room temperature. Serum samples were diluted 1:80 in 10 mM Tris-HCl (pH 7.4) containing 150 mM NaCl, 0.5 mM $MgCl_2$, 0.05% Tween-20, and 0.1% gelatin with or without 2 mM $CaCl_2$) and N protein. All samples and buffers were prepared on ice. The plates were then sequentially incubated for 1 hr at 4° C. and for 1.5 hr at 37° C. followed by washing. All incubation volumes were 100 μl. Complement binding was detected using antibodies followed by washing. Detection of C4, activated C3, and C5b-9 was performed using anti-C4α chain antibody (Santa Cruz), anti-activated C3 antibody (Santa Cruz), and anti-C5b-9 antibody (Calbiochem), respectively. Antibody binding was detected using HRP-conjugated sheep anti-mouse antibody or donkey anti-rabbit antibody (R&D). Enzyme activity of HRP was detected using TMB incubation for 30-60 min RT, and the reaction was stopped with 2 M $H_2SO_4$. The OD was measured at 450 nm using a microplate reader.

MASP-2: MBL Binding Assay.

Binding of MASP-2 to MBL was assessed by ELISA. As mentioned above, Nunc Maxisorb plates were coated with 10 μg mannan per well in 100 mM $Na_2CO_3/NaHCO_3$ (pH 9.6) at room temperature overnight and blocked with 2% HSA. MBL protein (1 μg/ml) was incubated in 10 mM Tris-HCl (pH 7.4), 150 mM NaCl, 5 mM $CaCl_2$), 100 μg/ml HSA, and 0.5% TritonX-100 at 4° C. for 2 hr. Purified MASP-2 and N (or control) proteins were added to the wells at different times to obtain final concentrations of 0.2 mg/ml and 200 ng/ml, respectively. The plates were washed after 32 hr of incubation at 4° C., and the binding of MASP-2 was detected with anti-MASP-2 antibody followed by HRP-conjugated rabbit anti-goat antibody. The enzyme activity of HRP was detected using TMB incubation for 30-60 min at RT, and the reaction was stopped with 2 M $H_2SO_4$. The OD was measured at 450 nm using a microplate reader.

Opsonocytophagic Assay.

Mouse cells isolated from peritoneal cavity were washed and inoculated with RPMI 1640 Media (10% FBS) in 96-well plates for 2 hr at 37° C. Serum was diluted by 0.781%, 1.562%, 3.125%, 6.25%, 12.5%, 25%, 50% and 100% with 1×PBS, 1 mM $CaCl_2$), and 2 mM $MgCl_2$. Diluted serum, SARS-CoV N protein (100 ng/ml) and *E. coli* (the ratio to cells was 10:1) were added to each well and incubated for 30 minutes at 37° C. The elute from pET22b-transformed *E. coli* was used as a negative control for purified N protein to exclude effects due to bacterial components that may active complement. The reaction was stop and cells were fixed with 10% neutral formalin. Complement C3c depositon was detected with FITC-C3c antibody, and the stained cells were counted. The points represent the mean values from two repeated wells. Error bars, mean±S.D. *$P<0.05$ and **$P<0.01$ by unpaired two-tailed Student's t-test. Mice.

Generation of Masp Null Mice and LPS Challenge

Groups of BALB/c mice were provided from the experimental animal center of the Academy of Military Medical Sciences. MASP-2−/− (KO) mice and negative control wild type (WT) mice were provided from Cyagen Biosciences Inc. All mice were maintained in the experimental animal center of the Academy of Military Medical Sciences (China). Mice (8-10/group) were infected three times (day 1, 2, 3) with $1\times10^{8-9}$ PFU Ad-N/Ad-null (Beijing BAC Biological Technologies) or a saline control via the tail vein, and LPS (5 mg/kg) was given via the tail vein on the 5-6th day. Anti-MASP-2 monoclonal antibody (200 μg/kg, HBT), anti-N monoclonal antibody (200 μg/kg, Sino Biolgical) or C1INH (4 mg/kg, Calbiochem) was injected via the tail vein 30 min before LPS injection.

Immunohistochemistry

Postmortem autopsy from the 4 patients died in Huoshenshan hospital was carried out by Dr. Xiuwu Bian under the approval of the hospital ethic committee and the family member of the death. The detailed results will be published elsewhere. Paraformaldehyde-fixed lung tissues was used for paraffin tissue sections and immunohistochemical staining with MBL (Santa Cruz), MASP-2 (Santa Cruz), C4α chain (Santa Cruz), C3 (Santa Cruz) or C5b-9 (Calbiochem) antibodies were carried as described before.

Detection of C5a in COVID-19 Patients.

Sera from mild or severe COVID-19 patients were collected under the approval of hospital ethic committee. Server patients were defined as fever or suspected respiratory infection, plus one of respiratory rate >30 breaths/min, severe respiratory distress, or $SpO_2$<90% on room air. Patient with pneumonia and no signs of severe pneumonia are defined as mild cases. Sera from 10 mild patients (5 male, 5 female), with an average of 56±12.1 years and an average 26.3±9.1 days of illness, were assayed. Sera from healthy people for physical were collected from the clinical laboratory. Serum C5a level was detected by double antibody sandwich ELISA (R&D).

C5a Antibody Therapy.

Mice-Human (IgG4) antibody against human C5a (Bdb-001 injection) was provided by Staidson Biopharmaceutical Co., Ltd, which was manufactured in accordance with the Good Manufacture Protocol. The injection was approved by National Medical Product Administration (NMDA) of China for phase I clinical trial in healthy subjects in 2019. After the SARS-CoV-2 coronavirus induced pneumonia (COVID-19) outbreak, the antibody was approved by NMDA for phase II clinical trial for the treatment of COVID-19 on Feb. 7, 2020 (2020L00003). Administration of the antibody to human was also approved by the Ethics Committee in Wuhan Huoshenshan Hospital. 300 mg anti-C5a antibody in 250 ml saline was administrated i.v. on day 1, 2, 3, 5, 7, 9 and 11. Arterial blood gas (ABG) test, C reaction protein (CRP), blood routine (blood RT) and Hepatic function were regularly determined. $SaO_2$, blood pressure, heart beat were monitored as required.

REFERENCES

1. World Health Organization Multicentre Collaborative Network for Severe Acute Respiratory Syndrome Diagnosis, Lancet 361, 1730 (May 17, 2003).
2. N. Lee et al., N. Engl. J. Med. 348, 1986 (2003).
3. J. F. Chan et al., Clin Microbiol Rev 28, 465 (April 2015).
4. C. Huang et al., The Lancet, (2020).
5. R. L. Graham, E. F. Donaldson, R. S. Baric, Nat. Rev. Microbiol. 11, 836 (December 2013).
6. P. A. Rota et al., Science 300, 1394 (May 30, 2003).
7. J. F. Chan et al., Clin. Microbiol. Rev. 28, 465 (April 2015).
8. P. Zhou et al., Nature, (2020).
9. M. Surjit et al., Journal of virology 79, 11476 (September 2005).
10. F. Yasui et al., J. Immunol. 181, 6337 (Nov. 1, 2008).
11. D. Deming et al., PLOS Med. 3, e525 (December 2006).
12. S. Sun et al., Am. J. Respir. Cell Mol. Biol. 49, 221 (August 2013).
13. J. Zhou et al., J. Infect. Dis. 209, 1331 (May 1, 2014).
14. M. Wills-Karp, Proc. Am. Thorac. Soc. 4, 247 (July 2007).
15. K. Takahashi, W. E. Ip, I. C. Michelow, R. A. Ezekowitz, Curr. Opin. Immunol. 18, 16 (February 2006).
16. R. Wallis, Immunobiology 212, 289 (2007).
17. W. K. Ip et al., J. Infect. Dis. 191, 1697 (May 15, 2005).
18. Y. Zhou et al., Journal of virology 84, 8753 (September 2010).
19. J. H. Chen et al., Proc. Natl. Acad. Sci. USA 101, 17039 (2004).
20. R. T. Pang et al., Clin. Chem. 52, 421 (March 2006).
21. R. Wang, H. Xiao, R. Guo, Y. Li, B. Shen, Emerg. Microbes Infect. 4, e28 (May 2015).
22. J. L. Liu, C. Cao, Q. J. Ma, Xi Bao Yu Fen Zi Mian Yi Xue Za Zhi 25, 777 (September 2009).
23. S. V. Petersen, S. Thiel, L. Jensen, R. Steffensen, J. C. Jensenius, J. Immunol. Methods 257, 107 (Nov. 1, 2001).
24. X. Y. Che et al., Emerg Infect Dis 10, 1947 (November 2004).
25. P. Gal et al., J Biol Chem 280, 33435 (Sep. 30, 2005).
26. T. Gao, H. Zhao, X. Liu, C. Cao, Letters in Biotechnology 22, 806 (2011).
27. L. Beinrohr, J. Dobo, P. Zavodszky, P. Gal, Trends Mol. Med. 14, 511 (December 2008).
28. S. V. Petersen, S. Thiel, L. Jensen, R. Steffensen, J. C. Jensenius, J Immunol Methods 257, 107 (Nov. 1, 2001).
29. N. Rawal, R. Rajagopalan, V. P. Salvi, J. Biol. Chem. 283, 7853 (Mar. 21, 2008).
30. M. Okroj, E. Holmquist, B. C. King, A. M. Blom, PLOS One 7, e47245 (2012).
31. D. S. Cole, B. P. Morgan, Clin. Sci. (Lond) 104, 455 (May 2003).
32. M. Devyatyarova-Johnson et al., Infect. Immun. 68, 3894 (July 2000).
33. J. R. Dunkelberger, W. C. Song, Cell Res. 20, 34 (January 2010).
34. D. K. Imagawa, N. E. Osifchin, W. A. Paznekas, M. L. Shin, M. M. Mayer, Proc. Natl. Acad. Sci. USA 80, 6647 (November 1983).
35. E. Sanchez-Galan et al., Cardiovasc. Res. 81, 216 (Jan. 1, 2009).
36. Y. Ren et al., Proteomics 4, 3477 (November 2004).
37. C. Drosten et al., N. Engl. J. Med. 348, 1967 (May 15, 2003).
38. Y. Ami et al., Microbiol. Immunol. 52, 118 (February 2008).
39. L. Zhang et al., J Med Virol 78, 1 (January 2006).
40. W. J. Schwaeble et al., Proc. Natl. Acad. Sci. USA 108, 7523 (May 3, 2011).

The invention claimed is:

1. A method of treating a subject having a medical condition caused by or associated with infection with a corona virus, the method comprising;

administering to a subject in need thereof an effective amount of an inhibitor of C5a activity, wherein the medical condition caused by or associated with infection with a corona virus is pneumonia, fever, or a combination thereof; wherein the inhibitor of C5a activity is a protein ligand that specifically binds to C5, or to C5a, or to a C5a receptor and wherein the corona virus is severe acute respiratory syndrome coronavirus 2 (SARS-CoV-2).

2. The method of claim 1, wherein the subject suffers from COVID-19.

3. The method of claim 1, wherein administering the inhibitor of C5a to the subject results in one or more of the following:

reduction of C-reactive protein;
reduction of fever;
increase of lymphocyte counts in blood;
reducing ALT/AST; and/or
increase of oxygen index ($PaO_2/FiO_2$).

4. The method of claim 1, wherein administering the inhibitor of C5a activity to the subject:

lowers the concentration of C5;
inhibits cleavage of C5 into C5a and C5b;
lowers the concentration of C5a;
inhibits binding between C5a and a C5a receptor;
lowers the concentration of a C5a receptor; and/or
inhibits the activity of a C5a receptor.

5. The method of claim 1, wherein the protein ligand comprises an antibody or an antigen-binding fragment thereof.

6. The method of claim 1, wherein the inhibitor of C5a activity reduces expression of C5 protein or a C5a receptor protein.

7. The method of claim 4, wherein the C5a receptor is C5aR and/or C5L2.

8. The method of claim 1, wherein the inhibitor of C5a activity is selected from the group consisting of:

(a) MEDI-7814, ALXN-1007, or NOX-D21, or an antigen-binding fragment thereof;
(b) an antibody or an antigen-binding fragment thereof, wherein said antibody or antigen-binding fragment thereof competes with one of the antibodies indicated under (a) for binding to C5a;
(c) Eculizumab, ALXN1210, ALXN5500, or LFG316, or an antigen-binding fragment thereof;
(d) an antibody or an antigen-binding fragment thereof, wherein said antibody or antigen-binding fragment thereof competes with one of the antibodies indicated under (c) for binding to C5;
(e) Nomacopan or RA101495;
(f) an antibody or an antigen-binding fragment thereof or a protein or a macrocyclic peptide wherein said antibody or antigen-binding fragment thereof or protein or macrocyclic peptide competes with one of the proteins or peptides indicated under (e) for binding to C5;
(g) Avacincaptad pegol;
(h) an antibody or an antigen-binding fragment thereof or an aptamer, wherein said antibody or antigen-binding fragment thereof or aptamer competes with Avacincaptad pegol for binding to C5;
(i) AMY-201 or Mirococept;
(j) an antibody or an antigen-binding fragment thereof or a protein wherein said antibody or antigen-binding fragment thereof or protein competes with one of the proteins indicated under (i) for binding to C3b;
(k) Bikaciomab;
(l) an antibody or an antigen-binding fragment thereof, wherein said antibody or antigen-binding fragment thereof competes with Bikaciomab for binding to Factor B;
(m) Lampalizumab;
(n) an antibody or an antigen-binding fragment thereof, wherein said antibody or antigen-binding fragment thereof competes with Lampalizumab for binding to Factor D;
(o) ALN-CC5;
(p) Avacopan or a compound according to formula II or formula III; or PMX-53 or a compound according to formula IV;
(q) an antibody or an antigen-binding fragment thereof, wherein said antibody or antigen-binding fragment thereof competes with avacopan or PMX-53 for binding to C5aR;
(r) clone S5/1 or clone 7H110, or an antigen-binding fragment thereof; and
(s) an antibody or an antigen-binding fragment thereof, wherein said antibody or antigen-binding fragment thereof competes with one of the antibodies indicated under (r) for binding to C5aR.

9. The method of claim 1, wherein the inhibitor of C5a activity specifically binds to a conformational epitope formed by amino acid sequences NDETCEQRA (SEQ ID NO: 2) and SHKDMQL (SEQ ID NO: 3) of human C5a, and wherein the inhibitor of C5a binds to at least one amino acid within the amino acid sequence according to SEQ ID NO: 2 and to at least one amino acid within the amino acid sequence according to SEQ ID NO: 3.

10. The method of claim 1, wherein the inhibitor of C5a activity is an antibody or an antigen-binding fragment thereof, comprising (i) a variable heavy chain with an amino acid sequence having at least 90% sequence identity to the amino acid sequence of SEQ ID NO: 34 and a variable light chain sequence with an amino acid sequence having at least 90% sequence identity to the amino acid sequence of SEQ ID NO: 35, wherein the variable heavy chain and the variable light chain comprise the amino acid sequences set forth in SEQ ID NOs: 6, 8, 10, 12, 14 and 16 of the light and heavy chain CDR1 to CDR3; or
(ii) a variable heavy chain sequence with an amino acid sequence having at least 90% sequence identity to the amino acid sequence of SEQ ID NO: 36 and the variable light chain sequence with an amino acid sequence having at least 90% sequence identity to the amino acid sequence of SEQ ID NO: 37, wherein the variable heavy chain and the variable light chain comprise the amino acid sequences set forth in SEQ ID NO: 7, 9, 11, 13, 15 and 17 of the light and heavy chain CDR1 to CDR3.

11. A method of reducing an inflammatory response in a subject suffering from a corona virus infection, the method comprising:

administering to the subject an effective amount of an inhibitor of C5a activity to reduce the inflammatory response in the subject suffering from a corona virus infection; wherein the inhibitor of C5a activity is a protein ligand that specifically binds to C5, or to C5a, or to a C5a receptor and wherein the corona virus is severe acute respiratory syndrome coronavirus 2 (SARS-CoV-2).

12. A method of improving organ function in a subject suffering from a corona virus infection, the method comprising:

administering to the subject an effective amount of an inhibitor of C5a activity to improve organ function in the subject suffering from a corona virus infection; wherein lung and/or hepatic organ function is improved in the subject; wherein the inhibitor of C5a activity is a protein ligand that specifically binds to C5, or to C5a, or to a C5a receptor and wherein the corona virus is severe acute respiratory syndrome coronavirus 2 (SARS-CoV-2).

* * * * *

SEQUENCE LISTING

```
<160> NUMBER OF SEQ ID NOS: 44

<210> SEQ ID NO 1
<211> LENGTH: 74
<212> TYPE: PRT
<213> ORGANISM: Homo sapiens

<400> SEQUENCE: 1

Thr Leu Gln Lys Lys Ile Glu Glu Ile Ala Ala Lys Tyr Lys His Ser
```

-continued 1               5                   10                  15

Val Val Lys Lys Cys Cys Tyr Asp Gly Ala Cys Val Asn Asn Asp Glu
            20                  25                  30

Thr Cys Glu Gln Arg Ala Ala Arg Ile Ser Leu Gly Pro Arg Cys Ile
        35                  40                  45

Lys Ala Phe Thr Glu Cys Cys Val Val Ala Ser Gln Leu Arg Ala Asn
    50                  55                  60

Ile Ser His Lys Asp Met Gln Leu Gly Arg
65                  70

<210> SEQ ID NO 2
<211> LENGTH: 9
<212> TYPE: PRT
<213> ORGANISM: Homo sapiens

<400> SEQUENCE: 2

Asn Asp Glu Thr Cys Glu Gln Arg Ala
1               5

<210> SEQ ID NO 3
<211> LENGTH: 7
<212> TYPE: PRT
<213> ORGANISM: Homo sapiens

<400> SEQUENCE: 3

Ser His Lys Asp Met Gln Leu
1               5

<210> SEQ ID NO 4
<211> LENGTH: 7
<212> TYPE: PRT
<213> ORGANISM: Homo sapiens

<400> SEQUENCE: 4

Asp Glu Thr Cys Glu Gln Arg
1               5

<210> SEQ ID NO 5
<211> LENGTH: 5
<212> TYPE: PRT
<213> ORGANISM: Homo sapiens

<400> SEQUENCE: 5

His Lys Asp Met Gln
1               5

<210> SEQ ID NO 6
<211> LENGTH: 13
<212> TYPE: PRT
<213> ORGANISM: Artificial Sequence
<220> FEATURE:
<223> OTHER INFORMATION: IFX-1 CDR3 heavy chain

<400> SEQUENCE: 6

Cys Ala Arg Gly Asn Asp Gly Tyr Tyr Gly Phe Ala Tyr
1               5                   10

<210> SEQ ID NO 7
<211> LENGTH: 15
<212> TYPE: PRT
<213> ORGANISM: Artificial Sequence
<220> FEATURE:
<223> OTHER INFORMATION: INab708 CDR3 heavy chain -continued

<400> SEQUENCE: 7

Cys Thr Arg Arg Gly Leu Tyr Asp Gly Ser Ser Tyr Phe Ala Tyr
1 5 10 15

<210> SEQ ID NO 8
<211> LENGTH: 10
<212> TYPE: PRT
<213> ORGANISM: Artificial Sequence
<220> FEATURE:
<223> OTHER INFORMATION: IFX-1 CDR3 light chain

<400> SEQUENCE: 8

Cys Gln Gln Ser Asn Glu Asp Pro Tyr Thr
1 5 10

<210> SEQ ID NO 9
<211> LENGTH: 10
<212> TYPE: PRT
<213> ORGANISM: Artificial Sequence
<220> FEATURE:
<223> OTHER INFORMATION: INab708 CDR3 light chain

<400> SEQUENCE: 9

Cys Gln Gln Asn Asn Glu Asp Pro Leu Thr
1 5 10

<210> SEQ ID NO 10
<211> LENGTH: 12
<212> TYPE: PRT
<213> ORGANISM: Artificial Sequence
<220> FEATURE:
<223> OTHER INFORMATION: IFX-1 CDR2 heavy chain

<400> SEQUENCE: 10

Ile Asp Pro Ser Asp Ser Glu Ser Arg Leu Asp Gln
1 5 10

<210> SEQ ID NO 11
<211> LENGTH: 12
<212> TYPE: PRT
<213> ORGANISM: Artificial Sequence
<220> FEATURE:
<223> OTHER INFORMATION: INab708 CDR2 heavy chain

<400> SEQUENCE: 11

Ile Leu Pro Gly Ser Gly Ser Thr Asn Tyr Asn Glu
1 5 10

<210> SEQ ID NO 12
<211> LENGTH: 7
<212> TYPE: PRT
<213> ORGANISM: Artificial Sequence
<220> FEATURE:
<223> OTHER INFORMATION: IFX-1 CDR2 light chain

<400> SEQUENCE: 12

Ile Tyr Ala Ala Ser Asn Leu
1 5

<210> SEQ ID NO 13
<211> LENGTH: 7
<212> TYPE: PRT
<213> ORGANISM: Artificial Sequence
<220> FEATURE:
<223> OTHER INFORMATION: INab708 CDR2 light chain

<400> SEQUENCE: 13

Ile Tyr Ala Ala Ser Asn Leu
1 5

<210> SEQ ID NO 14
<211> LENGTH: 14
<212> TYPE: PRT
<213> ORGANISM: Artificial Sequence
<220> FEATURE:
<223> OTHER INFORMATION: IFX-1 CDR1 heavy chain

<400> SEQUENCE: 14

Cys Lys Ala Ser Gly Tyr Ser Phe Thr Thr Phe Trp Met Asp
1 5 10

<210> SEQ ID NO 15
<211> LENGTH: 14
<212> TYPE: PRT
<213> ORGANISM: Artificial Sequence
<220> FEATURE:
<223> OTHER INFORMATION: INab708 CDR1 heavy chain

<400> SEQUENCE: 15

Cys Lys Ala Thr Gly Asn Thr Phe Ser Gly Tyr Trp Ile Glu
1 5 10

<210> SEQ ID NO 16
<211> LENGTH: 16
<212> TYPE: PRT
<213> ORGANISM: Artificial Sequence
<220> FEATURE:
<223> OTHER INFORMATION: IFX-1 CDR1 light chain

<400> SEQUENCE: 16

Cys Lys Ala Ser Gln Ser Val Asp Tyr Asp Gly Asp Ser Tyr Met Lys
1 5 10 15

<210> SEQ ID NO 17
<211> LENGTH: 16
<212> TYPE: PRT
<213> ORGANISM: Artificial Sequence
<220> FEATURE:
<223> OTHER INFORMATION: INab708 CDR1 light chain

<400> SEQUENCE: 17

Cys Lys Ala Ser Gln Ser Val Asp Tyr Asp Gly Asp Ser Tyr Met Asn
1 5 10 15

<210> SEQ ID NO 18
<211> LENGTH: 21
<212> TYPE: PRT
<213> ORGANISM: Artificial Sequence
<220> FEATURE:
<223> OTHER INFORMATION: IFX-1 FR1 heavy chain

<400> SEQUENCE: 18

Gln Val Gln Leu Gln Gln Ser Gly Pro Gln Leu Val Arg Pro Gly Thr
1 5 10 15

Ser Val Lys Ile Ser
20

<210> SEQ ID NO 19
<211> LENGTH: 15
<212> TYPE: PRT
<213> ORGANISM: Artificial Sequence
<220> FEATURE:
<223> OTHER INFORMATION: IFX-1 FR2 heavy chain

<400> SEQUENCE: 19

Trp Val Lys Gln Arg Pro Gly Gln Gly Leu Glu Trp Ile Gly Arg
1 5 10 15

<210> SEQ ID NO 20
<211> LENGTH: 33
<212> TYPE: PRT
<213> ORGANISM: Artificial Sequence
<220> FEATURE:
<223> OTHER INFORMATION: IFX-1 FR3 heavy chain

<400> SEQUENCE: 20

Arg Phe Lys Asp Arg Ala Thr Leu Thr Val Asp Lys Ser Ser Ser Thr
1 5 10 15

Val Tyr Met Gln Leu Ser Ser Pro Thr Ser Glu Asp Ser Ala Val Tyr
20 25 30

Tyr

<210> SEQ ID NO 21
<211> LENGTH: 11
<212> TYPE: PRT
<213> ORGANISM: Artificial Sequence
<220> FEATURE:
<223> OTHER INFORMATION: IFX-1 FR4 heavy chain

<400> SEQUENCE: 21

Trp Gly Gln Gly Thr Leu Val Thr Val Ser Ser
1 5 10

<210> SEQ ID NO 22
<211> LENGTH: 22
<212> TYPE: PRT
<213> ORGANISM: Artificial Sequence
<220> FEATURE:
<223> OTHER INFORMATION: IFX-1 FR1 light chain

<400> SEQUENCE: 22

Asp Ile Val Leu Thr Gln Ser Pro Ala Ser Leu Ala Val Ser Leu Gly
1 5 10 15

Gln Arg Ala Thr Ile Ser
20

<210> SEQ ID NO 23
<211> LENGTH: 13
<212> TYPE: PRT
<213> ORGANISM: Artificial Sequence
<220> FEATURE:
<223> OTHER INFORMATION: IFX-1 FR2 light chain

<400> SEQUENCE: 23

Trp Tyr Gln Gln Lys Pro Gly Gln Pro Pro Lys Leu Leu
1 5 10

<210> SEQ ID NO 24
<211> LENGTH: 33
<212> TYPE: PRT
<213> ORGANISM: Artificial Sequence
<220> FEATURE:
<223> OTHER INFORMATION: IFX-1 FR3 light chain

<400> SEQUENCE: 24

Gln Ser Gly Ile Pro Ala Arg Phe Ser Gly Ser Gly Ser Gly Thr Asp
1 5 10 15

-continued

```
Phe Thr Leu Asn Ile His Pro Val Glu Glu Glu Asp Ala Ala Thr Tyr
            20                  25                  30

Tyr


<210> SEQ ID NO 25
<211> LENGTH: 10
<212> TYPE: PRT
<213> ORGANISM: Artificial Sequence
<220> FEATURE:
<223> OTHER INFORMATION: IFX-1 FR4 light chain

<400> SEQUENCE: 25

Phe Gly Gly Gly Thr Lys Leu Glu Ile Lys
1               5                   10


<210> SEQ ID NO 26
<211> LENGTH: 20
<212> TYPE: PRT
<213> ORGANISM: Artificial Sequence
<220> FEATURE:
<223> OTHER INFORMATION: INab708 FR1 heavy chain

<400> SEQUENCE: 26

Val Gln Leu Leu Glu Ser Gly Ala Glu Leu Met Lys Pro Gly Ala Ser
1               5                   10                  15

Val Lys Ile Ser
            20


<210> SEQ ID NO 27
<211> LENGTH: 15
<212> TYPE: PRT
<213> ORGANISM: Artificial Sequence
<220> FEATURE:
<223> OTHER INFORMATION: INab708 FR2 heavy chain

<400> SEQUENCE: 27

Trp Val Lys Gln Arg Pro Gly His Gly Leu Glu Trp Ile Gly Glu
1               5                   10                  15


<210> SEQ ID NO 28
<211> LENGTH: 33
<212> TYPE: PRT
<213> ORGANISM: Artificial Sequence
<220> FEATURE:
<223> OTHER INFORMATION: INab708 FR3 heavy chain

<400> SEQUENCE: 28

Lys Phe Lys Gly Lys Ala Thr Leu Thr Ala Asp Thr Ser Ser Asn Thr
1               5                   10                  15

Ala Tyr Met Gln Leu Ser Ser Leu Thr Ser Glu Asp Ser Ala Val Tyr
            20                  25                  30

Tyr


<210> SEQ ID NO 29
<211> LENGTH: 11
<212> TYPE: PRT
<213> ORGANISM: Artificial Sequence
<220> FEATURE:
<223> OTHER INFORMATION: INab708 FR4 heavy chain

<400> SEQUENCE: 29

Trp Gly Gln Gly Thr Leu Val Thr Val Ser Ala
1               5                   10
```

-continued

<210> SEQ ID NO 30
<211> LENGTH: 22
<212> TYPE: PRT
<213> ORGANISM: Artificial Sequence
<220> FEATURE:
<223> OTHER INFORMATION: INab708 FR1 light chain

<400> SEQUENCE: 30

Asp Ile Val Leu Thr Gln Ser Pro Ala Ser Leu Ala Val Ser Leu Gly
1 5 10 15

Gln Arg Ala Thr Ile Ser
20

<210> SEQ ID NO 31
<211> LENGTH: 13
<212> TYPE: PRT
<213> ORGANISM: Artificial Sequence
<220> FEATURE:
<223> OTHER INFORMATION: INab708 FR2 light chain

<400> SEQUENCE: 31

Trp Tyr Gln Gln Lys Pro Gly Gln Pro Pro Lys Leu Leu
1 5 10

<210> SEQ ID NO 32
<211> LENGTH: 33
<212> TYPE: PRT
<213> ORGANISM: Artificial Sequence
<220> FEATURE:
<223> OTHER INFORMATION: INab708 FR3 light chain

<400> SEQUENCE: 32

Gly Ser Gly Ile Pro Ala Arg Phe Ser Gly Ser Gly Ser Gly Thr Asp
1 5 10 15

Phe Thr Leu Asn Ile His Pro Val Glu Glu Glu Val Ala Ala Thr Tyr
20 25 30

Tyr

<210> SEQ ID NO 33
<211> LENGTH: 10
<212> TYPE: PRT
<213> ORGANISM: Artificial Sequence
<220> FEATURE:
<223> OTHER INFORMATION: INab708 FR4 light chain

<400> SEQUENCE: 33

Phe Gly Ala Gly Thr Leu Leu Glu Leu Lys
1 5 10

<210> SEQ ID NO 34
<211> LENGTH: 120
<212> TYPE: PRT
<213> ORGANISM: Mus musculus

<400> SEQUENCE: 34

Gln Val Gln Leu Gln Gln Ser Gly Pro Gln Leu Val Arg Pro Gly Thr
1 5 10 15

Ser Val Lys Ile Ser Cys Lys Ala Ser Gly Tyr Ser Phe Thr Thr Phe
20 25 30

Trp Met Asp Trp Val Lys Gln Arg Pro Gly Gln Gly Leu Glu Trp Ile
35 40 45

Gly Arg Ile Asp Pro Ser Asp Ser Glu Ser Arg Leu Asp Gln Arg Phe
50 55 60

```
Lys Asp Arg Ala Thr Leu Thr Val Asp Lys Ser Ser Ser Thr Val Tyr
65                  70                  75                  80

Met Gln Leu Ser Ser Pro Thr Ser Glu Asp Ser Ala Val Tyr Tyr Cys
                85                  90                  95

Ala Arg Gly Asn Asp Gly Tyr Tyr Gly Phe Ala Tyr Trp Gly Gln Gly
            100                 105                 110

Thr Leu Val Thr Val Ser Ser Ala
        115                 120


<210> SEQ ID NO 35
<211> LENGTH: 111
<212> TYPE: PRT
<213> ORGANISM: Mus musculus

<400> SEQUENCE: 35

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Lys Trp Tyr Gln Gln Lys Pro Gly Gln Pro Pro
        35                  40                  45

Lys Leu Leu Ile Tyr Ala Ala Ser Asn Leu Gln Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110


<210> SEQ ID NO 36
<211> LENGTH: 120
<212> TYPE: PRT
<213> ORGANISM: Mus musculus

<400> SEQUENCE: 36

Val Gln Leu Leu Glu Ser Gly Ala Glu Leu Met Lys Pro Gly Ala Ser
1               5                   10                  15

Val Lys Ile Ser Cys Lys Ala Thr Gly Asn Thr Phe Ser Gly Tyr Trp
            20                  25                  30

Ile Glu Trp Val Lys Gln Arg Pro Gly His Gly Leu Glu Trp Ile Gly
        35                  40                  45

Glu Ile Leu Pro Gly Ser Gly Ser Thr Asn Tyr Asn Glu Lys Phe Lys
    50                  55                  60

Gly Lys Ala Thr Leu Thr Ala Asp Thr Ser Ser Asn Thr Ala Tyr Met
65                  70                  75                  80

Gln Leu Ser Ser Leu Thr Ser Glu Asp Ser Ala Val Tyr Tyr Cys Thr
                85                  90                  95

Arg Arg Gly Leu Tyr Asp Gly Ser Ser Tyr Phe Ala Tyr Trp Gly Gln
            100                 105                 110

Gly Thr Leu Val Thr Val Ser Ala
        115                 120


<210> SEQ ID NO 37
<211> LENGTH: 111
<212> TYPE: PRT
<213> ORGANISM: Mus musculus
```

<400> SEQUENCE: 37

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Gly Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Val Ala Ala Thr Tyr Tyr Cys Gln Gln Asn Asn
                85                  90                  95

Glu Asp Pro Leu Thr Phe Gly Ala Gly Thr Leu Leu Glu Leu Lys
            100                 105                 110
```

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic polypeptide

<400> SEQUENCE: 38

```
cggaattcca tatgtctgat aatggacccc aa                                32
```

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic polypeptide

<400> SEQUENCE: 39

```
cgggatcctt atgcctgagt tgaatcagc                                   29
```

<210> SEQ ID NO 40
<211> LENGTH: 38
<212> TYPE: PRT
<213> ORGANISM: Artificial Sequence
<220> FEATURE:
<223> OTHER INFORMATION: Consensus sequence Fig 7D

<400> SEQUENCE: 40

```
Met Lys Gln Leu Ser Pro Arg Trp Tyr Phe Tyr Tyr Leu Gly Thr Gly
1               5                   10                  15

Pro Glu Ala Gly Leu Pro Tyr Gly Ala Asn Lys Asp Gly Ile Ile Trp
            20                  25                  30

Val Ala Thr Glu Gly Ala
        35
```

<210> SEQ ID NO 41
<211> LENGTH: 38
<212> TYPE: PRT
<213> ORGANISM: Artificial Sequence
<220> FEATURE:
<223> OTHER INFORMATION: SARS-CoV sequence Fig 7D

<400> SEQUENCE: 41

```
Met Lys Glu Leu Ser Pro Arg Trp Tyr Phe Tyr Tyr Leu Gly Thr Gly
```

-continued

```
1               5                   10                  15

Pro Glu Ala Ser Leu Pro Tyr Gly Ala Asn Lys Glu Gly Ile Val Trp
            20                  25                  30

Val Ala Thr Glu Gly Ala
        35


<210> SEQ ID NO 42
<211> LENGTH: 38
<212> TYPE: PRT
<213> ORGANISM: Artificial Sequence
<220> FEATURE:
<223> OTHER INFORMATION: MERS-CoV sequence Fig 7D

<400> SEQUENCE: 42

Ile Lys Gln Leu Ala Pro Arg Gln Tyr Phe Tyr Tyr Thr Gly Thr Gly
1               5                   10                  15

Pro Glu Ala Ala Leu Pro Phe Arg Ala Val Lys Asp Gly Ile Val Trp
            20                  25                  30

Val His Glu Asp Gly Ala
        35


<210> SEQ ID NO 43
<211> LENGTH: 38
<212> TYPE: PRT
<213> ORGANISM: Artificial Sequence
<220> FEATURE:
<223> OTHER INFORMATION: HKU5 sequence Fig 7D

<400> SEQUENCE: 43

Thr Lys Pro Leu Ala Pro Arg Trp Tyr Phe Tyr Tyr Thr Gly Thr Gly
1               5                   10                  15

Pro Glu Ala Asn Leu Pro Phe Arg Ser Val Lys Asp Gly Ile Ile Trp
            20                  25                  30

Val His Glu Asn Gly Ala
        35


<210> SEQ ID NO 44
<211> LENGTH: 38
<212> TYPE: PRT
<213> ORGANISM: Artificial Sequence
<220> FEATURE:
<223> OTHER INFORMATION: SARS-CoV-2 sequence Fig 7D

<400> SEQUENCE: 44

Met Lys Asp Leu Ser Pro Arg Trp Tyr Phe Tyr Tyr Leu Gly Thr Gly
1               5                   10                  15

Pro Glu Ala Gly Leu Pro Tyr Gly Ala Asn Lys Asp Gly Ile Ile Trp
            20                  25                  30

Val Ala Thr Glu Gly Ala
        35
```